United States Patent
Devasthale et al.

(10) Patent No.: US 8,415,386 B2
(45) Date of Patent: Apr. 9, 2013

(54) AZOLOPYRROLONE MELANIN CONCENTRATING HORMONE RECEPTOR-1 ANTAGONISTS

(75) Inventors: Pratik Devasthale, Plainsboro, NJ (US); William N. Washburn, Titusville, NJ (US); Wei Wang, Princeton, NJ (US); Andres Hernandez, Lawrenceville, NJ (US); Saleem Ahmad, Wall, NJ (US); Guohua Zhao, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/122,995

(22) PCT Filed: Oct. 8, 2009

(86) PCT No.: PCT/US2009/059924
§ 371 (c)(1),
(2), (4) Date: Apr. 7, 2011

(87) PCT Pub. No.: WO2010/047956
PCT Pub. Date: Apr. 29, 2010

(65) Prior Publication Data
US 2011/0195934 A1 Aug. 11, 2011

Related U.S. Application Data

(60) Provisional application No. 61/103,660, filed on Oct. 8, 2008.

(51) Int. Cl.
*A61K 31/506* (2006.01)
*A61K 31/444* (2006.01)
*A61K 31/4439* (2006.01)
*A61K 31/4192* (2006.01)
*A61K 31/4162* (2006.01)
*C07D 487/04* (2006.01)

(52) U.S. Cl.
USPC ...... 514/406; 514/338; 514/210.21; 514/359; 514/275; 514/333; 546/275.7; 546/256; 548/360.5; 548/259; 544/331

(58) Field of Classification Search .................. 514/338, 514/210.21, 406, 359, 275, 333; 546/275.7, 546/256; 548/360.5, 259; 544/331
See application file for complete search history.

(56) References Cited

U.S. PATENT DOCUMENTS
2007/0093509 A1   4/2007   Washburn et al.

FOREIGN PATENT DOCUMENTS
WO   WO2004/094429 A1   11/2004
WO   WO2007/050726 A2   5/2007
WO   WO2007/092416 A2   8/2007

OTHER PUBLICATIONS

Jeon et al. Diabetes 2006, 55, 428-434.*
Luthin, D.R. Life Sciences 2007, 81, 423-440.*
The Mayo Clinic, Type 1 diabetes, Treatment and drugs, http://www.mayoclinic.com/health/type-1-diabetes/DS00329/DSECTION=treatments-and-drugs, accessed Oct. 10, 2012.*
Borowsky, B. et al., "Antidepressant, anxiolytic and anorectic effects of a melanin-concentrating hormone-1 receptor antagonist", Nature Medicine, vol. 8(8), pp. 825-830 (2002).
Gehlert, D. et al., "Preclinical Evaluation of Melanin-Concentrating Hormone Receptor 1 Antagonism for the Treatment of Obesity and Depression", The J. of Pharmacology & Experimental Therapeutics, vol. 329(2), pp. 429-438 (2009).
Handlon, A. et al., "Melanin-Concentrating Hormone-1 Receptor Antagonists for the Treatment of Obesity", J. Med. Chem., vol. 49, pp. 4017-4022 (2006).
Kokkotou, E. et al., "Melanin-concentrating hormone as a mediator of intestinal inflammation", PNAS, vol. 105(30), pp. 10613-10618 (2008).
Kowalski, T. et al., "Therapeutic potential of melanin-concentrating hormone-1 receptor antagonists for the treatment of obesity", Expert Opinion Investig. Drugs, vol. 13(9), pp. 1113-1122 (2004).
Kowalski, T. et al., "Melanin-concentrating hormone-1 receptor antagonism decreases feeding by reducing meal size", European Journal of Pharmacology, vol. 497, pp. 41-47 (2004).
Rivera, G. et al., "Melanin-Concentrating Hormone Receptor 1 Antagonists: A New Perspective for the Pharmacologic Treatment of Obesity", Current medicinal Chemistry, vol. 15, pp. 1025-1043 (2008).
Takekawa, S. et al., "T-226296: a novel, orally active and selective melanin-concentrating hormone receptor antagonist", European Journal of Pharmacology, vol. 438, pp. 129-135 (2002).
Ulven, T. et al., "6-Acylamino-2aminoquinolines as Potent Melanin-Concentrating Hormone 1 Receptor Antagonists. Identification, Structure-Activity Relationship, and Investigation of Binding Mode", J. Medical Chemistry, vol. 48, pp. 5684-5697 (2005).

* cited by examiner

*Primary Examiner* — Joseph Kosack
*Assistant Examiner* — Matthew Coughlin
(74) *Attorney, Agent, or Firm* — Maureen S. Gibbons; Jing G. Sun

(57) ABSTRACT

The present application provides compounds, including all stereoisomers, solvates, prodrugs and pharmaceutically acceptable forms thereof according to Formula I

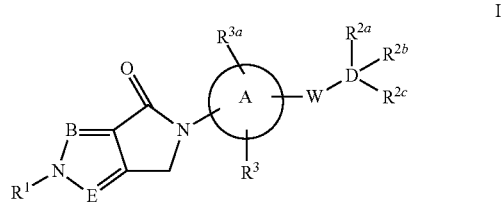

wherein all of the variables are defined herein.

20 Claims, No Drawings

AZOLOPYRROLONE MELANIN CONCENTRATING HORMONE RECEPTOR-1 ANTAGONISTS

CROSS-REFERENCE TO RELATED APPLICATIONS

The present application is a 371 application of PCT/US2009/059924 filed Oct. 8, 2009, which claims priority benefit of U.S. provisional application Ser. No. 61/103,660, filed Oct. 8, 2008, each of which is incorporated by reference herein.

FIELD OF THE INVENTION

The present invention relates to azolopyrrolone melanin concentrating hormone receptor-1 (MCHR1) antagonists, pharmaceutical compositions containing azolopyrrolone MCHR1 antagonists and methods of treating diabetes, obesity and related diseases employing such MCHR1 antagonists.

RELATED APPLICATIONS

This application claims priority to U.S. Ser. No. 61/103,660, filed Oct. 8, 2008, the disclosure of which is hereby incorporated by reference in its entirety.

BACKGROUND

Several lines of pharmacological and genetic evidence support the role of Melanin Concentrating Hormone Receptor-1 (hereafter "MCHR1") as a modulator of food intake and body weight. Central administration of MCH increases food intake and body weight in both rats and mice. Chronic ICV infusion of MCH causes increased food intake and ultimately obesity in mice, while infusion of an MCH peptide antagonist blocks MCH-induced food intake and results in weight loss and decreased feeding in diet-induced obese mice.

The expression of both the MCH peptide and receptor are modulated by nutritional status. MCH mRNA is upregulated both in hyperphagic obese mice (ob/ob), and fasted animals. Targeted disruption of the gene for MCH peptide results in hypophagia and leanness. Disruption of the MCHR1 gene causes leanness, altered metabolism, and hyperlocomotion accompanied by mild hyperphagia. Conversely, over-expression of MCH peptide results in hyperphagia, obesity and diabetes. Small molecule MCHR1 antagonists have been shown to cause weight loss in rodent weight and feeding models after both oral and intraperitoneal administration; *Eur. J. Pharmacol.*, 438:129-135 (2002), Nat. Med., 8:825-830 (2002), *Eur. J. Pharmacol.*, 497:41-47 (2004).

MCHR1 has also been reported to play a key role in the pathogenesis of acute experimental colitis and possibly human IBD (inflammatory bowel disease). It has been shown that immunoneutralization is an effective treatment for TNBS-induced colitis. Kokkotou, E. et al., "Melanin-concentrating hormone as a mediator of intestinal inflammation", *Proc. Natl. Acad. Sci.*, 105(30):10613-10618 (Jul. 29, 2008).

In addition, MCH and MCHR1 has also been reported to play a role in the endocrine and behavioral responses to stress. Treatment of rats and mice with MCHR antagonists produce a robust anti-depressant and anti-anxiolytic effect. (JPET DOI:10.1124/jpet.108.143362).

Numerous non-peptide MCHR1 antagonists have been disclosed. The scope of the genus for each reflects a common perception regarding the criteria required for ligand recognition as MCHR1 agonists. A recent review of MCHR1 patent disclosures emphasized the commonality of these structures by the following description; "Ubiquitous throughout the MCH patent literature are molecules consisting of a central scaffold to which linkers to an aryl or heteroaryl group and a basic amino functionality are attached" (Kowalski, Ti. et al., *Exp. Opin. Invest. Drugs*, 13:1113-1122 (2004)). Pharmacophore models of these geni consistently envision a presumed prerequisite electrostatic interaction between a basic amine center of the antagonist ligand and aspartic acid 123 of the receptor which presumably is envisaged to emulate the mandatory interaction between arginine 14 of MCH peptide agonists with aspartic acid 123 of the MCHR1 receptor. (Ulven, T. et al., *J. Med. Chem.*, 48:5684-5697 (2005)). However, incorporation of this basic amine in a MCHR1 antagonist increases substantially the probability of binding to off-target ion-channels and biogenic amine receptors.

U.S. Publication No. 2007/0093509 A1 published Apr. 26, 2007 discloses a series of novel high affinity selective MCHR1 antagonists of formula A:

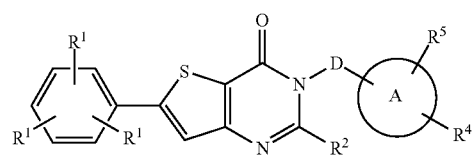

wherein,

A is phenyl or a monocyclic heteroaryl;

D is $CH_2$ or a direct bond;

$R^1$ is independently selected from hydrogen, halogen, lower alkyl, lower cycloalkyl, $CF_3$, $OR^6$ or $SR^6$;

$R^2$ is hydrogen or lower alkyl;

$R^4$ is hydroxyl or $G$-$D^2$-$Z_n$;

n is an integer from 1 to 3;

$R^5$ is hydrogen, halogen, lower alkyl, lower cycloalkyl, $CF_3$, $SR^6$, lower alkoxy, lower cycloalkoxy, CN, $CONR^7R^7$, $SOR^6$, $SO_2R^6$, $NR^7COR^7$, $NR^7CO_2R^7$, $CO_2R^6$, heteroaryl, $NR^7SO_2R^6$ or $COR^6$;

G is O, S or $CR^7R^7$, $D^2$ is a direct bond, lower alkyl, lower cycloalkyl or a 4 to 6-membered non-basic heterocycle;

Z is hydrogen, hydroxyl, lower alkoxy, lower cycloalkoxy, $OCONR^7R^7$, CN, $CONR^7R^7$, $SOR^6$, $SO_2R^6$, $NR^7COR^7$, $NR^7CO_2R^7$, $CO_2R^6$, heteroaryl, $NR^6SO_2R^6$ or $COR^6$;

$R^6$ is independently selected from lower alkyl or lower cycloalkyl; and $R^7$ is independently selected from hydrogen, lower alkyl or lower cycloalkyl, wherein two $R^7$ and the atom to which they are attached may optionally form a ring of 4 to 7 atoms.

There is currently a need in the art for additional small molecule antagonists of MCHR1.

SUMMARY OF THE INVENTION

The present invention is directed to compounds that are useful as MCHR1 antagonists, having the following formula I:

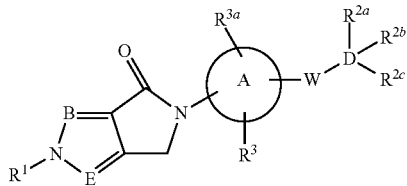
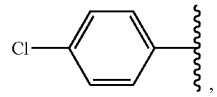

including all pharmaceutically acceptable salts and stereoisomers thereof:
wherein

is a monocyclic aryl, preferably phenyl, or monocyclic heteroaryl, preferably pyridyl or pyrimidinyl;

W is a direct bond, —O—, or —N($R^6$)—;

D is a direct bond, substituted or unsubstituted $C_1$ to $C_4$ alkyl, substituted or unsubstituted $C_3$ to $C_7$ cycloalkyl, cycloalkylalkyl, or a 4 to 6 membered cyclic amine;

B and E are independently N or CH provided that both are not CH;

$R^1$ is substituted or unsubstituted phenyl, wherein the substituent is preferably chloro, or substituted or unsubstituted pyridyl, wherein the substituent is preferably chloro;

$R^{2a}$, $R^{2b}$, and $R^{2c}$ are independently selected from the group consisting of hydrogen, halo, cyano, hydroxyl, —$NR^5R^{5a}$, —$OSO_2R^{34}$, —$NR^5CO_2R^{21}$, —$NR^5COR^{21}$, —$CO_2R^{35}$, substituted or unsubstituted $C_1$ to $C_4$ alkyl, substituted or unsubstituted $C_3$ to $C_7$ cycloalkyl, a substituted or unsubstituted 4 to 6 membered cyclic amine wherein the cyclic amine is optionally substituted with —OH; carbonylamino, alkoxycarbonylamino; a prodrug moiety selected from amino acid esters or phosphoric acid esters wherein said amino acid ester has the formula —OC(O)CH($NH_2$)$R^{31}$; or any two of $R^{2a}$, $R^b$, or $R^{2c}$, may be taken together to form a cycloalkyl or a cyclic amine; provided that if D is a direct bond $R^{2a}$, $R^{2b}$ and $R^{2c}$ are each independently H, alkyl, or cycloalkyl;

$R^3$ and $R^{3a}$ are each independently selected from the group consisting of hydrogen, hydroxyl, lower alkoxy, halo, CN, substituted or unsubstituted $C_1$ to $C_4$ alkyl, perfluoroalkyl, substituted or unsubstituted $C_3$ to $C_7$ cycloalkyl, and cycloalkoxy; or either $R^3$ and D or $R^{3a}$ and D may optionally be taken together with the atoms to which they are attached to form a 5- to 7-membered ring;

$R^5$ and $R^{5a}$ are the same or different and are independently selected from the group consisting of hydrogen, substituted or unsubstituted alkyl, hydroxyalkyl, hydroxyalkylcycloalkyl, substituted or unsubstituted heterocycloalkyl, acyl, alkoxycarbonyl, carboxyalkyl, substituted or unsubstituted cycloalkyl, substituted or unsubstituted cycloalkylalkyl, and substituted or unsubstituted cycloalkoxyalkyl; or the $R^5$ and $R^{5a}$ groups and the N atom to which they are attached may form a ring;

$R^{31}$ is H or $C_1$ to $C_4$ alkyl;

$R^{21}$ and $R^{34}$ are alkyl;

$R^{35}$ is H or alkyl; and $R^6$ is selected from the group consisting of H, $C_1$ to $C_4$ alkyl and $C_3$ to $C_7$ cycloalkyl, provided that
(1) when $R^1$ is

B is CH, E is N,

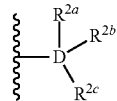

is

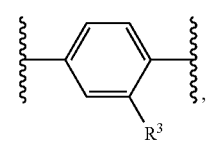

$R^3$ is $OCH_3$, and W is O, then

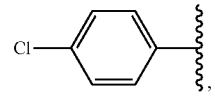

is other than $CH_3$;
(2) when $R^1$ is

B is N, E is CH,

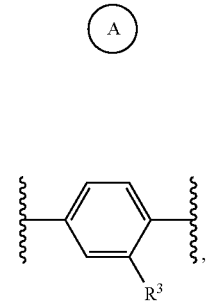

is $R^3$ is $OCH_3$, and W is O, then

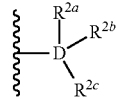

is other than —SO$_2$CH$_3$; or (3) when R$^1$ is

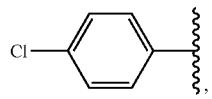

B is N, E is CH,

is

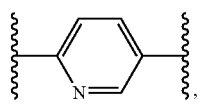

R$^3$ is H, and W is O, then

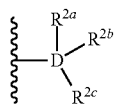

is other than

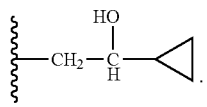 [SMILES: *CC(O)C1CC1]

According to one embodiment of the present invention, compounds have the Formula I, as described above, wherein:

W is a direct bond;

D is a cyclic amine selected from the group consisting of pyrrolidinyl, piperidinyl, and azetidinyl;

R$^{2a}$, R$^{2b}$, and R$^{2c}$ are each independently, H, —OH, halo, —N(R$^5$, R$^{5a}$), —NR$^5$CO$_2$R$^{21}$, —NR$^5$COR$^{21}$, halo, pyrrolidinyl, azetidinyl, or —OC(O)CH(NH$_2$)CH(CH$_3$)$_2$; or R$^{2a}$ and R$^{2b}$ are taken together to form a cyclic amine optionally substituted with F, hydroxyalkyl, —C(O)alkyl, or benzyl; and R$^5$ and R$^{5a}$ are independently selected from the group consisting of H, C$_1$ to C$_4$ alkyl, hydroxyalkyl, and cycloalkoxyalkyl.

According to one embodiment of the invention, compounds have the Formula I, as described above, wherein:

W is O and D is a direct bond, methyl, ethyl, or propyl and R$^{2a}$, R$^{2b}$, and R$^{2c}$ are, independently, H, —OH, —OC(O)C(NH$_2$)R$^{31}$, hydroxyalkyl, cyclopropyl, pyrrolidinyl, —OSO$_2$R$^{34}$, —CO$_2$H, —OP(O)(OH)(OH), or R$^{2a}$ and R$^{2b}$ are joined together to form a cycloalkyl substituted with halo or hydroxyl.

According to one embodiment of the present invention, compounds have the Formula I as described above, wherein

is phenyl, pyridinyl, or pyrimidinyl; R$^1$ is phenyl or pyridyl substituted with Cl; R$^3$ and R$^{3a}$ are H, C$_1$ to C$_4$ alkyl, or methoxy; W is O or a bond; D a bond, C$_1$ to C$_4$ alkyl, pyrrolidinyl, piperidinyl, or azetidinyl; and R$^2$, R$^{2b}$, and R$^{2c}$ are independently H, OH, alkyl, cycloalkyl, —OSO$_2$R$^{34}$; —OC(O)CH(NH$_2$)R$^{31}$; —NR$^5$R$^{5a}$; NR$^5$CO$_2$R$^{21}$; —NR$^5$COR$^{21}$; halo; —OP(O)(OH)$_2$, or any two of R$^{2a}$, R$^{2b}$, and R$^c$ join together to form a cyclic amine or a cycloalkyl; R$^{34}$ is C$_1$ to C$_4$ alkyl; R$^5$ and R$^{5a}$ are H or alkyl, and R$^{21}$ is alkyl.

DETAILED DESCRIPTION OF THE INVENTION

The present application provides compounds, including all stereoisomers, solvates, prodrugs and pharmaceutically acceptable forms thereof according to Formula I. Additionally, the present application provides pharmaceutical compositions containing at least one compound according to Formula I and optionally at least one additional therapeutic agent. Finally, the present invention provides methods for treating a patient suffering from an MCHR-1 modulated disease or disorder such as, for example, obesity, diabetes, inflammatory bowel disease, depression or anxiety by administration of a therapeutically effective dose of a compound according to Formula I.

Thus, in accordance with the present invention a compound is provided having the formula I, including all stereoisomers and pharmaceutically acceptable salts thereof:

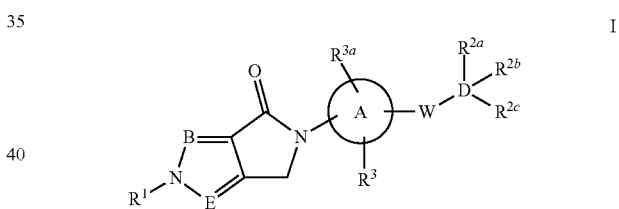

wherein

is selected from monocyclic aryl, monocyclic heteroaryl, and bicyclic heteroaryl;

W is selected from a direct bond, —O—, —N(R$^6$)—, —S—, —S(O)—, —S(O$_2$)—, and —C(R$^7$)(R$^8$)—, and is preferably a direct bond, —O— or —N(R$^6$)—; W is a direct bond, —O—, or —N(R$^6$)—, provided that if W is a direct bond, D must be a cyclic amine that is attached to A via the nitrogen atom of said cyclic amine;

D is selected from a direct bond, lower alkyl, cycloalkyl, and heterocyclyl, S(O$_2$)—, and

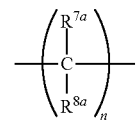

where n is 1 to 3, D is preferably a direct bond, substituted or unsubstituted C$_1$ to C$_4$ alkyl, substituted or unsubstituted C$_3$ to $C_7$ cycloalkyl, cycloalkylalkyl, or a 4 to 6 membered cyclic amine, such as pyrrolidinyl, piperidinyl, or azetidinyl, wherein the cyclic amine can be substituted with any of the substituents defined for amines, and are preferably substituted with H, —OH, halo, —N($R^5$, $R^{5a}$), —$NR^5CO_2R^{21}$, —$NR^5COR^{21}$, halo, pyrrolidinyl, azetidinyl, or —OC(O)CH($NH_2$)$R^{31}$; or $R^{2a}$ and $R^{2b}$ are taken together to form a cyclic amine optionally substituted with F, hydroxyalkyl, —C(O)alkyl, or benzyl;

B is selected from CH or N, and E is selected from CH or N, with the proviso that B and E are not both CH;

$R^1$ is selected from aryl or heteroaryl and is preferably phenyl or pyridyl which is preferably substituted with a halo, such as —Cl;

$R^{2a}$, $R^{2b}$, and $R^{2c}$ are independently selected from hydrogen, halo, cyano, acylamino, hydroxyl, hydroxyalkyl, lower alkyl, cycloalkyl, lower alkoxy, cycloalkoxy, heterocyclyl, heteroaryl, cycloalkylalkyl, heterocycloalkyl, alkylsulfonyloxy, oxo(=O), alkoxycarbonylamino, hydroxyalkoxycarbonylamino, dialkylaminoheterocyclyl, monoalkylaminoheterocyclyl, hydroxy(cycloalkyl)alkyl, or $NR^5R^{5a}$; or is absent; preferably, $R^{2a}$, $R^{2b}$, and $R^{2c}$ are independently hydrogen, halo, cyano, hydroxyl, —$NR^5R^{5a}$, —$OSO_2R^{34}$, —$NR^5CO_2R^{21}$, —$NR^5COR^{21}$, —$CO_2R^{35}$, substituted or unsubstituted $C_1$ to $C_4$ alkyl, substituted or unsubstituted $C_3$ to $C_7$ cycloalkyl, a substituted or unsubstituted 4 to 6 membered cyclic amine wherein the cyclic amine is optionally substituted with —OH; carbonylamino, alkoxycarbonylamino; a prodrug moiety selected from amino acid esters or phosphoric acid esters wherein said amino acid ester has the formula —OC(O)CH($NH_2$)$R^{31}$; or any two of $R^{2a}$, $R^b$, or $R^{2c}$, may be taken together to form a cycloalkyl or a cyclic amine; provided that if D is a direct bond $R^{2a}$, $R^{2b}$ and $R^{2c}$ are each independently H, alkyl, or cycloalkyl;

$R^3$ and $R^{3a}$ are the same or different and are independently selected from hydrogen, hydroxyl, lower alkoxy, halo, CN, lower alkyl, perfluoroalkyl, cycloalkyl, cycloalkoxy, amino, alkylamino, dialkylamino, and aminoalkyl, or $R^3$ and/or $R^{3a}$ are absent, or $R^3$ or $R^{3a}$ and D may optionally be taken together with the atoms to which they are attached to form a 5- to 7-membered heterocyclyl ring; preferably, $R^3$ and $R^{3a}$ are each independently selected from the group consisting of hydrogen, hydroxyl, lower alkoxy, halo, CN, substituted or unsubstituted $C_1$ to $C_4$ alkyl, perfluoroalkyl, substituted or unsubstituted $C_3$ to $C_7$ cycloalkyl, and cycloalkoxy; or either $R^3$ or $R^{3a}$ and D may optionally be taken together with the atoms to which they are attached to form a 5- to 7-membered ring;

$R^5$ and $R^{5a}$ are the same or different and are independently selected from hydrogen, lower alkyl, hydroxyalkyl, hydroxyalkylcycloalkyl, heterocycloalkyl, acyl, alkoxycarbonyl, carboxyalkyl, cycloalkyl, and cycloalkylalkyl, wherein the $R^5$ and $R^{5a}$ groups and the N atom to which they are attached may optionally form a heterocyclyl ring of 4 to 7 atoms; this heterocyclyl ring can be optionally substituted with small polar groups such as OH, CN, $NR^5R^{5a}$, or $NR^5COOR^{21}$; $R^{5a}$ or $R^5$ can also be optionally fused to the heterocyclyl ring or form a spirocycle; or $R^{5a}$ and $R^5$ can optionally be taken together with the N atom to which they are attached to form a 4- to 7-membered ring;

$R^6$ is selected from H, lower alkyl and cycloalkyl; and $R^7$ and $R^8$ and $R^{7a}$ and $R^{8a}$ are the same or different and are independently selected from hydrogen and alkyl; and provided that
(1) when $R^1$ is

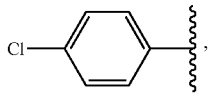

B is CH, E is N,

is

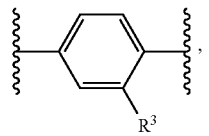

$R^3$ is $OCH_3$, and W is O, then

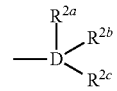

is other than $CH_3$;
(2) when $R^1$ is

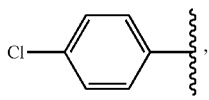

B is N, E is CH,

is

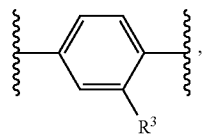

$R^3$ is $OCH_3$, and W is O, then

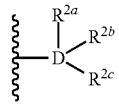

is other than —SO$_2$CH$_3$; or
(3) when R$^1$ is

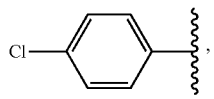

B is N, E is CH,

is

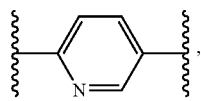

R$^3$ is H, and W is O, then

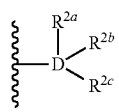

is other than

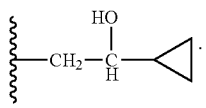

The bicyclic core ring

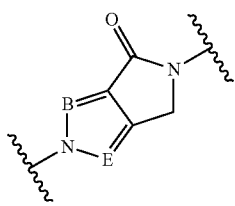

in the formula I compounds of the invention and formula ID compounds (set out below) of the invention will preferably include

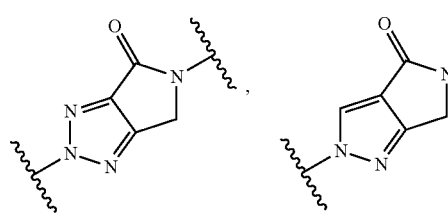

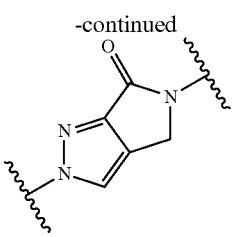

The R$^1$ group is preferably phenyl or heteroaryl preferably 2-pyridinyl, 3-pyridinyl or 2-pyrimidinyl, wherein the aryl or heteroaryl is preferably substituted with one to three R$^4$ substituents at the para-position, and/or meta-positions, and wherein each of the R$^4$ substituents are the same or different and are independently selected from H, lower alkyl, lower alkoxy, halo, cycloalkyl, and polyfluoroalkyl, such as 4-OCH$_3$, 4-Cl, 4-CF$_3$, 3-F and 5-cyclopropyl.

It will be appreciated that where D and/or W is a direct bond or other moiety as defined for D and/or W, the R$^{2a}$, R$^{2b}$ and/or R$^{2c}$ groups will be present, where possible, according to the number of available valences.

Thus, the compounds of formula I of the invention include the following subgenuses:

IA

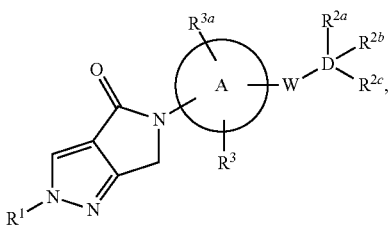

IB

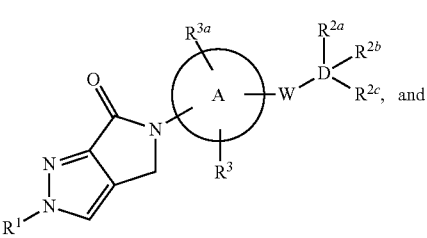

IC

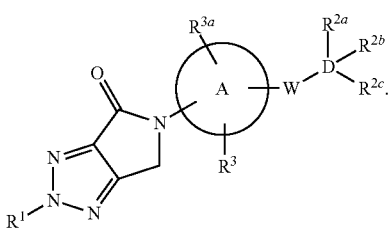

In one embodiment of formula I of the invention, compounds are provided having the structure ID

ID

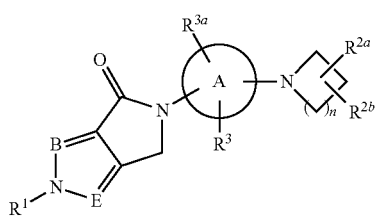

wherein
R¹, B, E,

R³ and R³ᵃ are as defined for formula I;
n is 1, 2 or 3;
R²ᵃ and R²ᵇ are the same or different and can be attached to separate carbons on the azo ring in which case R²ᵃ and R²ᵇ are the same or different and may be independently and are preferably selected from H, NR⁵R⁵ᵃ, OH, oxo(=O), halo, cyano, acylamino, alkoxycarbonylamino, or hydroxyalkyloxycarbonylamino, or R²ᵃ and R²ᵇ and the carbons to which they are linked optionally form a bicyclic heterocycle which can be optionally substituted with one to three substituents which can be the same or different and are independently and preferably selected from OH, CN, or oxo(=O), or
R²ᵃ and R²ᵇ are the same or different and can be attached to a single carbon atom, in which case R²ᵃ and R²ᵇ may optionally be connected via a ring to form a spirocycle which can optionally be substituted with one to three substituents which may be the same or different and are independently and preferably selected from OH, CN, or oxo(=O).

Examples of preferred

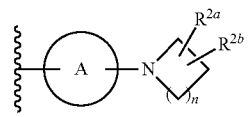

groups include

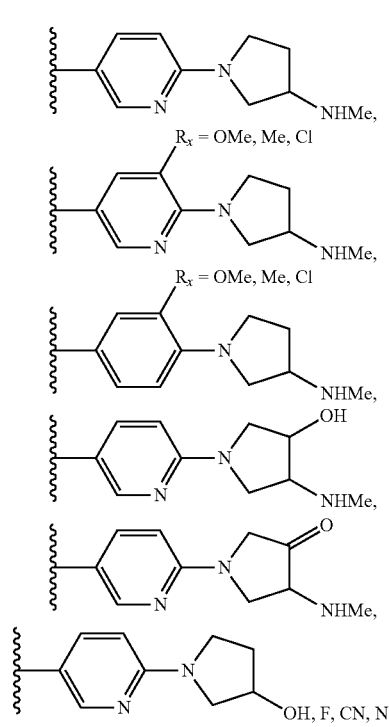

-continued

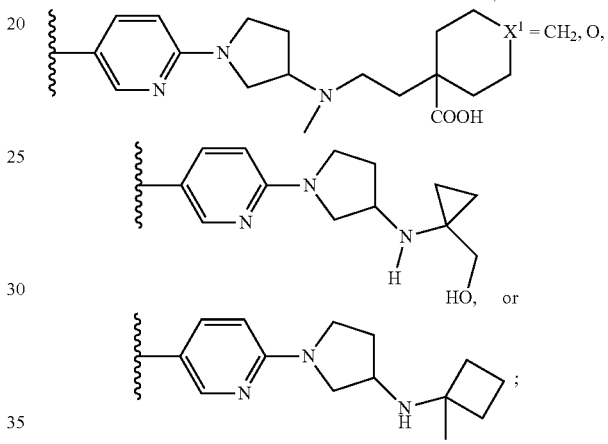

spirocyclics such as

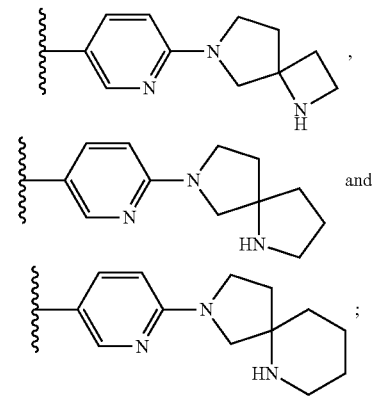

or
heterocyclic azocycles such as

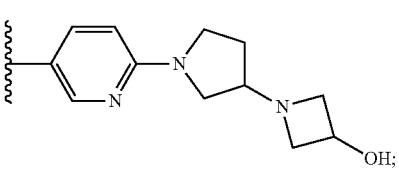 [SMILES: *c1ccc(N2CCC(N3CC(O)C3)C2)nc1]

or
  bicyclics such as or
  carbamates such as or
  amides such as or
  lactams such as or
  oxazolidinones such as In some embodiments of the compounds of formula I of the invention, R¹ is aryl, preferably phenyl, which may or may not be substituted, and is preferably substituted at the para-position with halogen such as Cl or polyfluoroalkyl such as $CF_3$, including or heteroaryl such as In some embodiments of the compounds of formula I of the invention, E is CH and B is N or E is N and B is CH or E is N and B is N.

In some embodiments of the compounds of formula I of the invention, is phenylene, preferably or heteroaryl which is In some embodiments of the compounds of formula I of the invention, $R^3$ is lower alkoxy, preferably —$OCH_3$, or H, halo, or alkyl, or is absent and $R^{3a}$ is H or is absent.

In some embodiments of the compounds of formula I of the invention, W is O or a direct bond.

In some embodiments of the compounds of formula I of the invention, D is a bond or

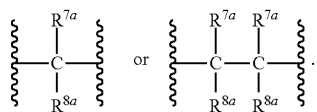

In some embodiments of the compounds of formula I of the invention, $R^{2a}$ is lower alkyl, such as $CH_3$, hydroxyalkyl such as

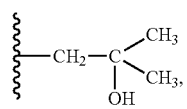

cycloalkyl such as

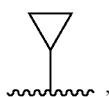 [SMILES: *C1CC1]

cycloalkylalkyl such as

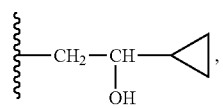 [SMILES: *CC(O)C1CC1]

or heterocycloalkyl such as

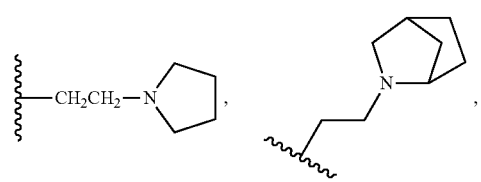

OH, heterocyclyl such as

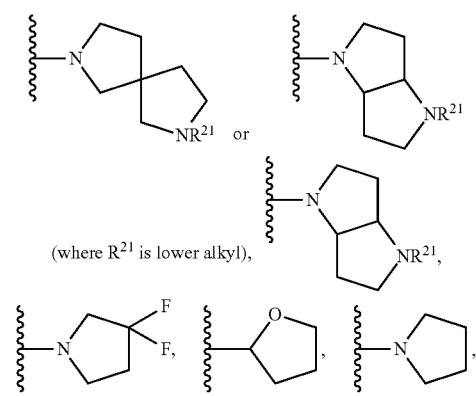

(where $R^{21}$ is lower alkyl),

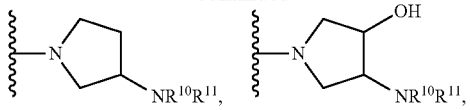

mono- or -dialkylaminoheterocyclyl such as

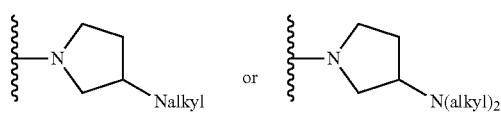

(where alkyl is preferably $CH_3$), $NR^5R^{5a}$ such as

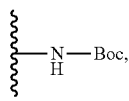

$NH_2$, $NHCH_3$ or $N(CH_3)_2$ or heteroaryl such as

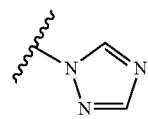

or $OSO_2CH_3$.

In some embodiments of the compounds of formula I of the invention, $R^{2b}$ and $R^{2c}$ are independently H, cycloalkyl such as

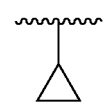 [SMILES: *C1CC1]

or lower alkyl such as $CH_3$, or are absent.

In some embodiments of the compounds of formula I of the invention,

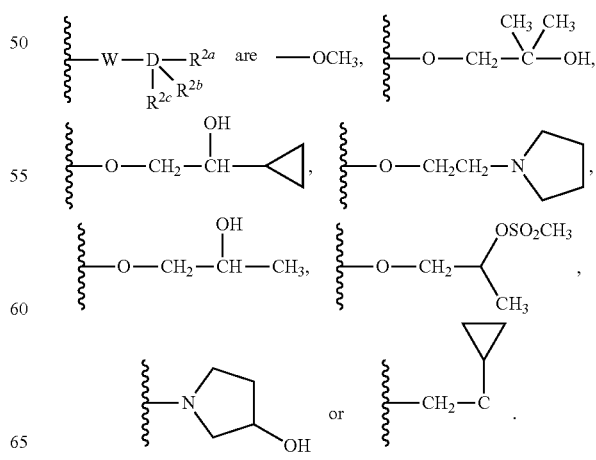

In some embodiments of the compounds of formula I of the invention,
$R^1$ is aryl such as
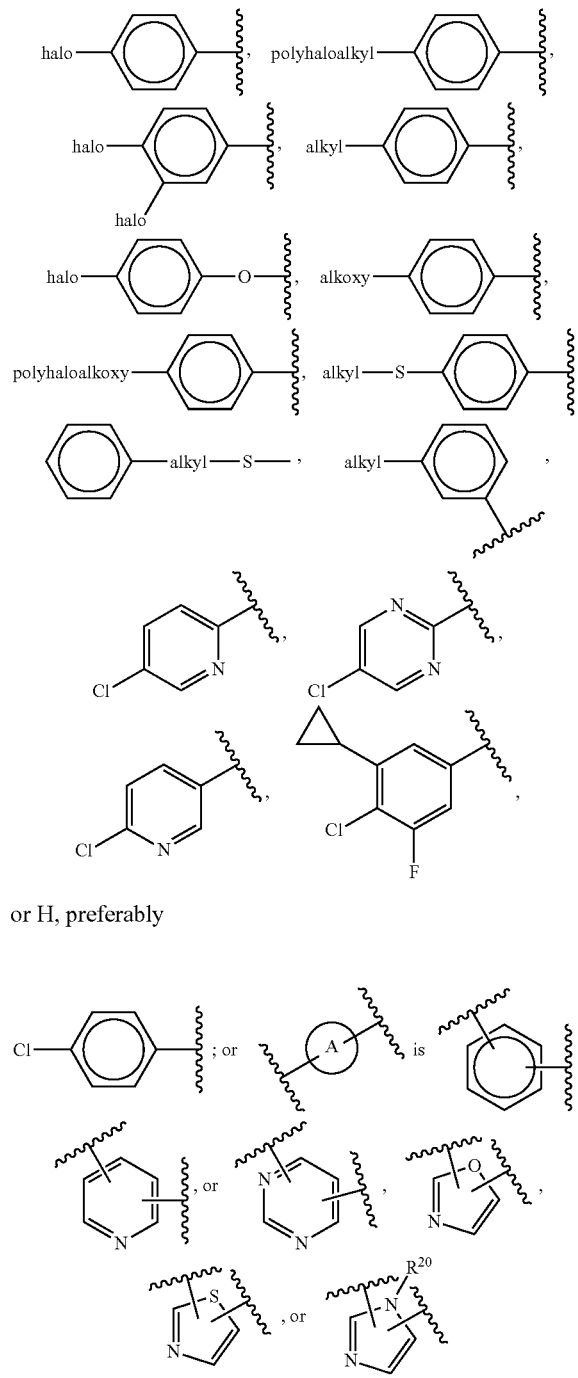
or H, preferably
where $R^{20}$ is lower alkyl;
is preferably
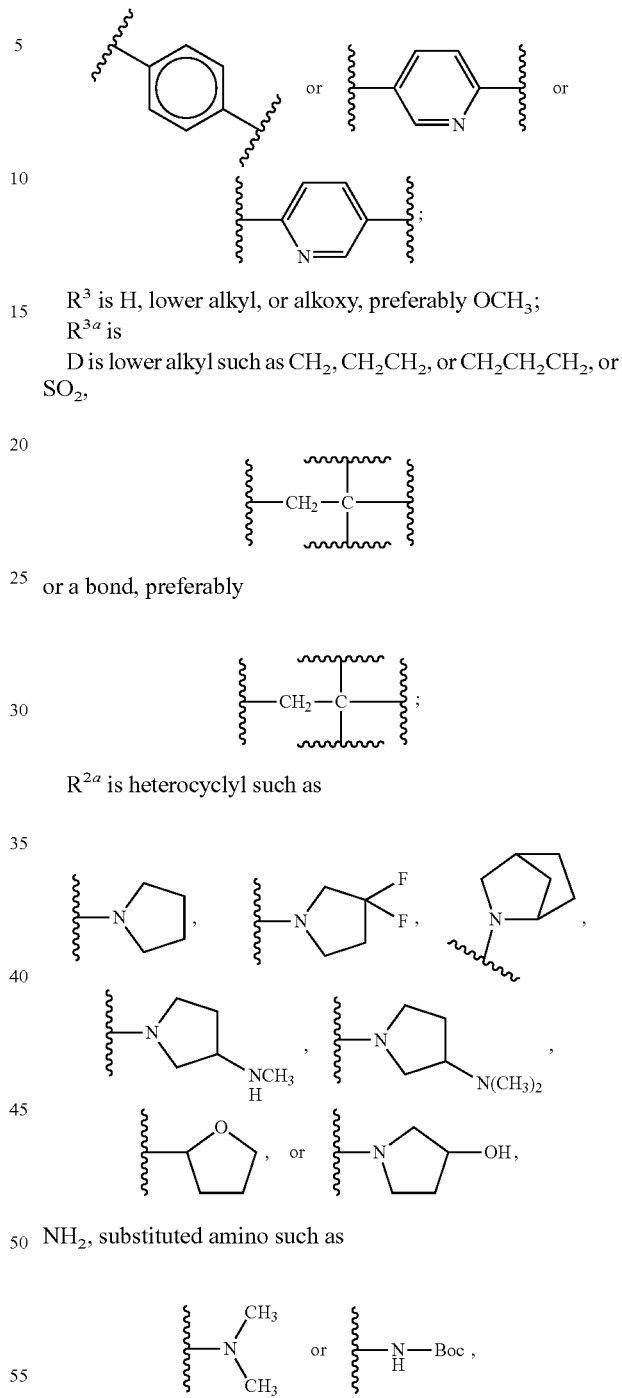
$R^3$ is H, lower alkyl, or alkoxy, preferably $OCH_3$;
$R^{3a}$ is
D is lower alkyl such as $CH_2$, $CH_2CH_2$, or $CH_2CH_2CH_2$, or $SO_2$,
or a bond, preferably
$R^{2a}$ is heterocyclyl such as
$NH_2$, substituted amino such as
$NHCH_3$, heteroaryl such as
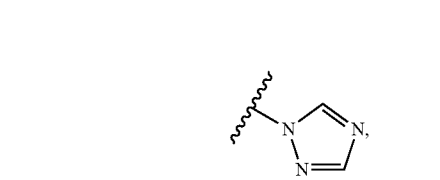 [SMILES: *n1cncn1]

cycloalkyl such as

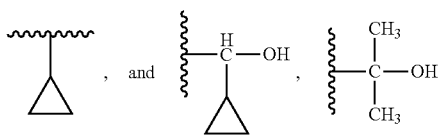

or OH;

$R^{2b}$ and $R^{2c}$ are each H;

W is O;

E is CH and B is N, or E is N and B is CH, or E is N and B is N.

In some embodiments of the present invention, pharmaceutical compositions are provided which include at least one compound having the Formula I, as described above, and at least one pharmaceutically acceptable diluent or carrier.

In some embodiments of the present invention, methods are provided for treating a patient suffering from an MCHR1 modulated disease or disorder such as, for example, obesity, diabetes, depression, anxiety or intestinal inflammation such as inflammatory bowel disease, colitis or Crohn's disease by administration of a therapeutically effective dose of a compound according to Formula I, optionally in combination with other therapeutic agents, such as those described below.

Definitions

Unless otherwise indicated, the term "lower alkyl" as employed herein alone or as part of another group includes both straight and branched chain hydrocarbons containing 1 to 8 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, trimethylpentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

The term "$C_1$ to $C_4$ alkyl" includes a straight chain alkyl having from 1 to 4 carbon atoms, which may optionally be substituted with groups selected from alkyl groups (to form branched chains) or other substituents such as F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" or "lower cycloalkyl" as employed herein alone or as part of another group includes saturated or partially unsaturated (containing 1 or 2 double bonds) cyclic hydrocarbon groups containing 1 to 3 rings, any one of which may optionally be a Spiro substituted cycloalkyl, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

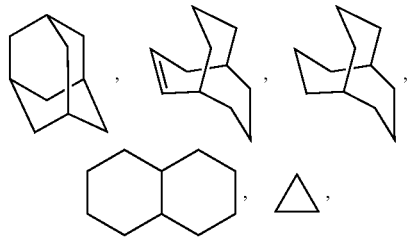

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, —$CO_2R$ wherein R is H or alkyl, nitro, cyano, thiol and/or alkylthio and/or any of the alkyl substituents.

Unless otherwise indicated, the term "cycloalkoxy" or "lower cycloalkoxy" as employed herein alone or as part of another group, represents a 4-, 5- or 6-membered saturated ring containing an oxygen in the ring and includes

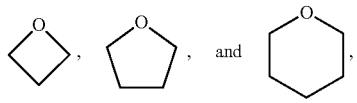

and which may be optionally substituted with 1 or 2 of any of the substituents as set out for cycloalkyl.

The terms "heterocyclo", "heterocyclyl" or "heterocyclic" as used herein, alone or as part of another group, represents an unsubstituted or substituted stable 4- to 7-membered monocyclic ring system which may be saturated or unsaturated, and which consists of carbon atoms, with one to four heteroatoms selected from nitrogen, oxygen or sulfur, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, or oxadiazolyl or other heterocycles described in Katritzky, A. R. et al., eds., *Comprehensive Heterocyclic Chemistry The Structure, Reactions, Synthesis and Uses of Heterocyclic Compounds*, Pergamon Press, New York, N.Y. (1984); and Katritzky, A. R. et al., eds., *Comprehensive Heterocyclic Chemistry II: A Review of the Literature* 1982-1995, Elsevier Science, hue., Tarrytown, N.Y. (1996); and references therein. The heterocycloalkyl may optionally be substituted with at least one of F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

The term "alkanoyl" as used herein alone or as part of another group refers to alkyl linked to a carbonyl group.

The term "halogen" or "halo" as used herein alone or as part of another group refers to chlorine, bromine, fluorine, and iodine, with chlorine or fluorine being preferred.

The term "metal ion" refers to alkali metal ions such as sodium, potassium or lithium and alkaline earth metal ions such as magnesium and calcium, as well as zinc and aluminum.

The term "aryl" herein alone or as part of another group refers to monocyclic or bicyclic aromatic rings, e.g., phenyl, substituted phenyl and the like, as well as groups which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, alkyl, alkenyl, cycloalkyl, heterocycloalkyl, alkoxy, haloalkoxy, haloalkyl, hydroxy, carboxy, carbamoyl, alkyloxycarbonyl, nitro, alkenyloxy, trifluoromethyl, amino, cycloalkyl, aryl, heteroaryl, cyano, alkyl $S(O)_m$ (m=0, 1, 2), or thiol and/or any of the alkyl substituents set out herein.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur. Such rings may be fused to an aryl, cycloalkyl, heteroaryl or heterocyclyl and include possible N-oxides as described in Katritzky, A. R. et al., eds. *Comprehensive Heterocyclic Chemistry: The Structure, Reactions, Synthesis and Uses of Heterocyclic Compounds*, Pergamon Press, New York, N.Y. (1984); and Katritzky, A. R. et al., eds., *Comprehensive Heterocyclic Chemistry II: A Review of the Literature* 1982-1995, Elsevier Science, Inc., Tarrytown, N.Y. (1996); and references therein. Further, "heteroaryl", as defined herein, may optionally be substituted with one or more substituents such as the substituents included above in the definition of "substituted alkyl" and "substituted aryl". Examples of heteroaryl groups include the following:

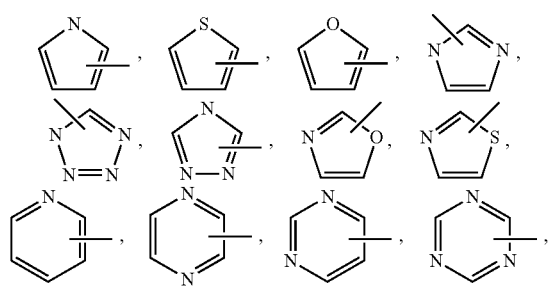

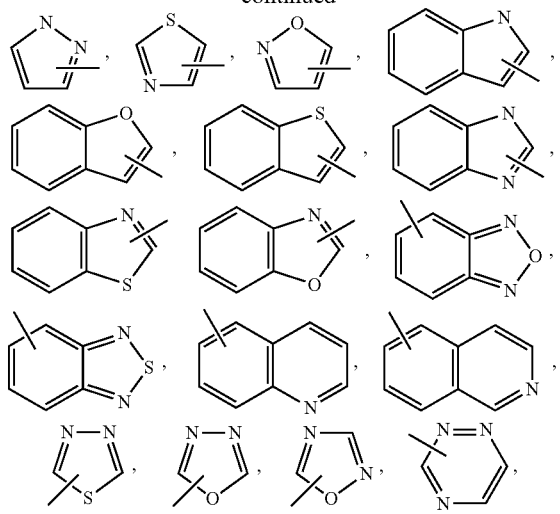

and the like.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "lower alkylthio", "alkylthio", "arylthio" or "aralkylthio" as employed herein alone or as part of another group includes any of the above alkyl, aralkyl or aryl groups linked to a sulfur atom.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "acyl" as used herein alone or as part of another group refers to a radical linked to a carbonyl (C=O) group which radical can be, for example, lower alkyl, aryl, heterocyclo, heteroaryl, cycloalkyl, lower alkoxy or amino.

Pharmaceutical Compositions

According to some embodiments of the present invention, pharmaceutical compositions are provided, comprising at least one compound having Formula I, as described herein, and at least one pharmaceutically acceptable diluent or carrier. The pharmaceutical compositions of the present invention, may optionally include at least one additional therapeutic agent selected from the group consisting of anti-obesity agents; anti-diabetic agents, appetite suppressants; cholesterol/lipid-lowering agents, and HDL-raising agents, as defined herein.

The present invention is also directed to pharmaceutical combinations, comprising at least one compound having the Formula I, and at least one additional therapeutic agent, selected from the group consisting of anti-obesity agents; anti-diabetic agents, appetite suppressants; cholesterol/lipid-lowering agents, and HDL-raising agents, as defined herein.

According to one embodiment of the present invention, the anti-diabetic agent is selected from the group consisting of insulin secretagogues, insulin sensitizers, glucokinase inhibitors, glucocorticoid antagonist, fructose 1,6-bis phosphatase inhibitors, AMP kinase activators, incretin modulators glucosidase inhibitors, aldose reductase inhibitors PPAR γ agonists, PPAR α agonists, PPAR δ antagonists or agonists, PPAR α/γ dual agonists, 11-β-HSD-1 inhibitors, dipeptidyl peptidase IV (DP4) inhibitors, SGLT2 inhibitors, insulin, glucagon-like peptide-1 (GLP-1), GLP-1 agonists, and PTP-1B inhibitors.

According to one embodiment of the present invention, the additional therapeutic agent is an antiobesity agent selected from group consisting of melanocortin receptor (MC4R) agonists, cannabinoid receptor modulators, growth hormone secretagogue receptor (GHSR) antagonists, galanin receptor modulators, orexin antagonists, CCK agonists, GLP-1 agonists, Pre-proglucagon-derived peptides; NPY1 or NPY5 antagonists; NPY2 and NPY4 modulators; orticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, thyroid receptor beta modulators, lipase inhibitors, serotonin receptor agonists, monoamine reuptake inhibitors or releasing agents, anorectic agents, CNTF, BDNF, DGAT inhibitors, leptin, leptin receptor modulators, and cannabinoid-1 receptor inverse agonists/neutral antagonists.

Methods of Use

According to one embodiment of the present invention, methods are provided for treating obesity in a patient in need of such treatment, which includes the step of administering a therapeutically effective amount of at least one compound according to Formula I alone or in combination with one or more additional antiobesity agents, wherein the obesity agent is selected from those described herein.

According to one embodiment of the present invention, methods are provided for treating diabetes, especially Type II diabetes, in a patient in need of such treatment, which includes the step of administering a therapeutically effective amount of at least one compound according to Formula I alone or in combination with one or more additional antidiabetic agents, wherein the diabetic agent is described herein.

According to one embodiment of the present invention, methods for treating depression in a patient are provided, which includes the step of administering a therapeutically effective amount of at least one compound according to Formula I.

According to one embodiment of the present invention, methods are provided for treating anxiety in a patient in need of such treatment, which includes the step of administering a therapeutically effective amount of a compound having Formula I.

According to another embodiment of the present invention, methods are provided for treating intestinal inflammatory conditions, such as inflammatory bowel disease (IBD), colitis and Crohn's disease (CD) in a patient in need of such treatment which includes the step of administering a therapeutically effective amount of a compound of Formula I.

The assessment of activity of the compounds of Formula I of the invention in treating intestinal inflammation such as caused by inflammatory bowel disease, colitis and/or Crohn's disease, as described above, may be carried out employing the various assays as disclosed in Kokkotou, E. et al., "Melanin-concentrating hormone as a mediator of intestinal inflammation", *Proc. Natl. Acad. Sci.,* 105(30):10613-10618 (Jul. 29, 2008).

Utility

The compounds of the present invention can be administered to mammals, preferably humans, for the treatment of a variety of conditions and disorders, including, but not limited to metabolic and eating disorders as well as conditions associated with metabolic disorders (e.g., obesity, diabetes, arteriosclerosis, hypertension, polycystic ovary disease, cardiovascular disease, osteoarthritis, dermatological disorders, impaired glucose hemostasis, insulin resistance, hypercholesterolemia, hypertriglyceridemia, choletithiasis, dislipidemic conditions, bulimia nervosa and compulsive eating disorders); sleep disorders; and psychiatric disorders, such as depression, anxiety, schizophrenia, substance abuse, cognition-enhancement and Parkinson's disease; and inflammatory diseases such as inflammatory bowel disease, colitis and/or Crohn's disease.

The compounds described in the present invention could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and neurotropic agents (e.g., piracetam, levetiracetam). Examples of suitable therapies for treatment of Alzheimer's disease and cognitive disorders for use in combination with the compounds of the present invention include donepezil, tacrine, revastigraine, 5HT6, gamma secretase inhibitors, beta secretase inhibitors, SK channel blockers, Maxi-K blockers, and KCNQs blockers.

The compounds described in the present invention could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transporter modulators, such as ropinirole, or pramipexole or neurotrophic factors such as glial derived neurotrophic factor (GDNF).

Dosage Forms

The compounds of the present invention can be administered in oral dosage form The dosage form for said pharmaceutical composition includes such oral dosage forms as granules, powders, tablets, capsules, syrups, emulsions, suspensions, etc. and such non-oral dosage forms as injections (e.g., subcutaneous, intravenous, intramuscular and intraperitoneal injections), drip infusions, external application forms (e.g., nasal spray preparations, transdermal preparations, ointments, etc.), and suppositories (e.g., rectal and vaginal suppositories).

These dosage forms can be manufactured by the per se known technique conventionally used in pharmaceutical procedures. The specific manufacturing procedures are as follows.

To manufacture an oral dosage form, an excipient (e.g., lactose, sucrose, starch, mannitol, etc.), a disintegrator (e.g., calcium carbonate, carboxymethylcellulose calcium, etc.), a binder (e.g., a-starch, gum arabic, carboxymethylcellulose, polyvinylpyrrolidone, hydroxypropylcellulose, etc.), and a lubricant (e.g., talc, magnesium stearate, polyethylene glycol 6000, etc.), for instance, are added to the active component or components and the resulting composition is compressed. Where necessary, the compressed product is coated, by the per se known technique, for masking the taste or for enteric dissolution or sustained release. The coating material that can be used includes, for instance, ethylcellulose, hydroxymethylcellulose, polyoxyethylene glycol, cellulose acetate phthalate, hydroxypropylmethylcellulose phthalate, and EUDRAGIT® (Rohm & Haas, Germany, methacrylic-acrylic copolymer).

Injections can be manufactured typically by the following procedure. The active component or components are dissolved, suspended or emulsified in an aqueous vehicle (e.g., distilled water, physiological saline, Ringer's solution, etc.) or an oily vehicle (e.g., vegetable oil such as olive oil, sesame oil, cottonseed oil, corn oil, etc. or propylene glycol) together with a dispersant, e.g., Tween 80 (Atlas Powder, U.S.A.), HCO 60 (Nikko Chemicals), polyethylene glycol, carboxymethylcellulose, sodium alginate, etc.), a preservative (e.g., methyl p-hydroxybenzoate, propyl p-hydroxybenzoate, benzyl alcohol, chlorobutanol, phenol, etc.), an isotonizing agent (e.g., sodium chloride, glycerol, sorbitol, glucose, inverted sugar, etc.) and other additives. If desired, a solubilizer (e.g., sodium salicylate, sodium acetate, etc.), a stabilizer (e.g., human serum albumin), a soothing agent (e.g., benzalkonium chloride, procaine hydrochloride, etc.) and other additives can also be added.

A dosage form for external application can be manufactured by processing the active component or components into a solid, semi-solid or liquid composition. To manufacture a solid composition, for instance, the active component or components, either as they are or in admixture with an excipient (e.g., lactose, mannitol, starch, microcrystalline cellulose, sucrose, etc.), a thickener (e.g., natural gums, cellulose derivatives, acrylic polymers, etc.), etc., are processed into powders. The liquid composition can be manufactured in substantially the same manner as the injections mentioned above. The semi-solid composition is preferably provided in a hydrous or oily gel form or an ointment form. These compositions may optionally contain a pH control agent (e.g., carbonic acid, phosphoric acid, citric acid, hydrochloric acid, sodium hydroxide, etc.), and a preservative (e.g., p-hydroxybenzoic acid esters, chlorobutanol, benzalkonium chloride, etc.), among other additives.

Suppositories can be manufactured by processing the active component or components into an oily or aqueous composition, whether solid, semi-solid or liquid. The oleaginous base that can be used includes, for instance, higher fatty acid glycerides [e.g., cacao butter, Witepsols (Dinamit-Nobel), etc.], medium-chain fatty acids [e.g., Migriols (Dinamit-Nobel), etc.], vegetable oils (e.g., sesame oil, soybean oil, cotton-seed oil, etc.), etc. The water-soluble base includes, for instance, polyethylene glycols propylene glycol, etc. The hydrophilic base includes, for instance, natural gums, cellulose derivatives, vinyl polymers, and acrylic polymers, etc.

Dosages

The dosage of the pharmaceutical composition of the present invention may be appropriately determined with reference to the dosages recommended for the respective active components and can be selected appropriately according to the recipient, the recipient's age and body weight, current clinical status, administration time, dosage form, method of administration, and combination of the active components, among other factors. For example, the dosage of the insulin sensitivity enhancer for an adult can be selected from the clinical oral dose range of 0.01 to 10 g/kg body weight (preferably 0.05 to 10 mg/kg body weight, more preferably 0.05 to 5 mg/kg body weight) or the clinical parenteral dose range of 0.005 to 10 mg/kg body weight (preferably 0.01 to 10 mg/kg body weight, more preferably 0.01 to 1 mg/kg body weight).

The other active component or components having different modes of action for use in combination can also be used in dose ranges selected by referring to the respective recommended clinical dose ranges.

The proportions of the active components in the pharmaceutical composition of the present invention can be appropriately selected according to the recipient, the recipient's age and body weight, current clinical status, administration time, dosage form, method of administration, and combination of active components, among other factors.

Pharmaceutical Combinations

The present invention includes within its scope phal maceutical compositions includes, as an active ingredient, a therapeutically effective amount of at least one of the compounds of Formula I of the invention, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

The pharmaceutical combinations of the present invention can be formulated in combination, or separately by mixing the respective active components either together or independently with a physiologically acceptable carrier, excipient, binder, diluent, etc. When the active components are formulated independently, the respective formulations can be extemporaneously admixed using a diluent or the like and administered or can be administered independently of each other, either concurrently or at staggered times to the same subject. So, such other therapeutic agent(s) may be administered prior to, simultaneously with, or following the administration of the melanin-concentrating hormone receptor (MCHR) antagonists in accordance with the invention.

Examples of suitable anti-obesity agents for use in combination with the compounds of the present invention include melanocortin receptor (MC4R) agonists, cannabinoid receptor modulators, growth hormone secretagogue receptor (GHSR) antagonists, galanin receptor modulators, orexin antagonists, CCK agonists, GLP-1 agonists, and other Preproglucagon-derived peptides; NPY1 or NPY5 antagonist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491, 134, 5,776,983 and 5,488,064, a thyroid receptor beta modulator, such as a thyroid receptor ligand as disclosed in WO 97/21993 (U. Cal SF), WO 99/00353 (KaroBio) and WO 00/039077 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/AXOKINE® (Regeneron), BDNF (brain-derived neurotrophic factor), leptin and leptin receptor modulators, or cannabinoid-1 receptor inverse agonists/neutral antagonists, such as SR-141716 (Sanofi) or SLV-319 (Solvay) and DGAT inhibitors such as those described in WO 2006/134317 (A1) (Astra Zeneca), WO 2006/044775 (A2) (Bayer), WO 2006/06019020 (A1) (Sankyo), WO 2006/082010 (A1) (Roche), WO 2004/047755 (A2) (Japan Tobacco, Tularik), and WO 2005/0727401 (A2) (Amgen, Japan Tobacco).

Examples of suitable anti-diabetic agents for use in combination with the compounds of the present invention include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors including saxagliptin, vildagliptin and sitagliptin, SGLT2 inhibitors including dapagliflozin and sergiflozin, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594,016), Glaxo-Wellcome's GL-262570, englitazone (CP-68722, Pfizer) or darglitazone (CP-86325, Pfizer, isaglitazone (MIT/J&J), ITT-501 (JPNT/P&U), L-895645 (Merck), R-119702 (Sankyo/WL), N,N-2344 (Dr. Reddy/NN), or YM-440 (Yamanouchi), preferably rosiglitazone and pioglitazone.

The compounds of the present invention may be employed with a PPARα/γ dual agonist such as MK-767/KRP-297 (Merck/Kyorin; as described in Yajima, K. et al., *Am. J. Physiol. Endocrinol. Metab.*, 284:E966-E971 (2003)), AZ-242 (tesaglitazar; Astra-Zeneca; as described in Ljung, B. et al., *J. Lipid Res.*, 43:1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054,3-carboxy-2-hydroxy-propane-phosphonic acid derivatives as disclosed in French Patent No. 2,596,393,2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al., *J. Med. Chem.*, 31:1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A. et al., *Current Pharmaceutical Design*, 2:1-40 (1996).

In addition, other squalene synthetase inhibitors suitable for use herein include the terpenoid pyrophosphates disclosed by Ortiz de Montellano, P. et al., *J. Med. Chem.*, 20:243-249 (1977), the farnesyl diphosphate analog A and presqualene pyrophosphate (PSQ-PP) analogs as disclosed by Corey et al., *J. Am. Chem. Soc.*, 98:1291-1293 (1976), phosphinylphosphonates reported by McClard, R. W. et al., *J. Am. Chem. Soc.*, 109:5544 (1987) and cyclopropanes reported by Capson, T. L., Ph.D. dissertation, June, 1987, Dept. Med. Chem., U. of Utah, Abstract, Table of Contents, pp. 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-SEPHADEX® (SECHOLEX®, Policexide) and cholestagel (Sankyo/Geltex), as well as LIPOSTABIL® (Rhone-Poulenc), MAI® E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, *Drugs of the Future,* 24:9-15 (1999) (Avasimibe); Nicolosi et al., "The ACAT inhibitor, Cl-1011 is effective in the prevention and regression of aortic fatty streak area in hamsters", Atherosclerosis (Shannon, Irel.), 137(1):77-85 (1998); Ghiselli, G., "The pharmacological profile of FCE 27677: a novel ACAT inhibitor with potent hypolipidemic activity mediated by selective suppression of the hepatic secretion of ApoB100-containing lipoprotein", *Cardiovasc. Drug Rev.,* 16(1):16-30 (1998); Smith, C. et al., "RP 73163: a bioavailable alkylsulfinyl-diphenylimidazole ACAT inhibitor", *Bioorg. Med. Chem. Lett.,* 6(1):47-50 (1996); Krause, B. R. et al., Chapter 6: "ACAT Inhibitors: Physiologic Mechanisms for Hypolipidemic and Anti-Atherosclerotic Activities in Experimental Animals", *Inflammation: Mediators and Pathways,* CRC Press, Inc., publ., Ruffolo, Jr., R. R. et al., eds., pp. 173-198 (1995); Sliskovic et al., "ACAT inhibitors: potential anti-atherosclerotic agents", *Curr. Med. Chem.,* 1(3):204-225 (1994); Stout et al., "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", *Chemtracts: Org. Chem.,* 8(6):359-362 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis,* 115:45-63 (1995) and *J. Med. Chem.,* 41:973 (1998).

The other lipid agent or lipid-modulating agent may be a cholesteryl transfer protein inhibitor (CETP) such as Pfizer's CP-529,414 as well as those disclosed in WO 00/38722 and in EP 818448 (Bayer) and EP 992496, and Pharmacia's SC-744 and SC-795, as well as CETi-1 and JTT-705.

The hypolipidemic agent may be an ileal $Na^+$/bile acid cotransporter inhibitor such as disclosed in *Drugs of the Future,* 24:425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-1 (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin, rosuvastatin, and ezetimibe as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and/or T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043, 265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

MCHR1 antagonists could be useful in treating other diseases associated with obesity, including sleep disorders. Therefore, the compounds described in accordance with the present invention could be used in combination with therapeutics for treating sleep disorders. Examples of suitable therapies for treatment of sleeping disorders for use in combination with the compounds of the present invention include melatonin analogs, melatonin receptor antagonists, ML 1 B agonists, GABA receptor modulators; NMDA receptor modulators, histamine-3 (H3) receptor modulators, dopamine agonists and orexin receptor modulators.

MCHR1 antagonists may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

MCHR1 antagonists may reduce anxiety or depression; therefore, the compounds described in accordance with the present invention may be used in combination with anti-anxiety agents or antidepressants. Examples of suitable anti-anxiety agents for use in combination with the compounds of the present invention include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present invention include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpha-adrenoreceptor antagonists, and atypical antidepressants (bupropion, lithium, nefazodone, trazodone and viloxazine).

The combination of a conventional antipsychotic drug with a MCHR1 antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present invention include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), diphenylbutylpiperidine (pimozide) and indolone (molindolone) classes of antipsychotic agents. Other antipsychotic agents with potential therapeutic value in combination with the compounds in the present invention include loxapine, sulpiride and risperidone.

Combination of the compounds in the present invention with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, schizoaffective disorder, delusional disorder, brief psychotic disorder and psychotic disorder not specified. Examples of suitable antipsychotic drugs for combination with the compounds in the present invention include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

Methods of Preparation

The compounds of the present invention can be prepared in a number of ways well known to one skilled in the art of organic synthesis using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

Azolopyrrolones of formula I of the invention can be prepared by following the schemes shown below.

5,6-Dihydropyrrolo[3,4-c]pyrazol-4(2H)-ones of formula IA of the invention can be prepared following Scheme 1. Pyrazole-diester is can be prepared by condensation of chlorohydrazone 3 (prepared from condensation of commercially available arylhydrazines and readily accessible 2-chloroacetoacetic acid esters) and commercially available aminoacrylate 4. Reduction of the $R^{14}$ ester (where $R^{14}$ is benzyl, ethyl or methyl) of the diester 5 followed by hydrolysis of the $R^{15}$ ester (where $R^{15}$ is ethyl, methyl or benzyl) affords acid 7. Acid 7 is coupled with amine 8 under standard coupling conditions and then the resulting primary alcohol is converted to a leaving group using MsCl or TsCl to yield intermediate 9. Cyclization of the intermediate 9 in the presence of a base can afford the desired 5,6-dihydropyrrolo[3,4-c]pyrazol-4(2H)-ones (IA).

Examples of preparation of primary amines 6 are shown in Schemes 8A and 8B. In the case where compound S is defined as 8a with M, Q=$CR^3$, compound 8a is prepared via reaction of appropriate phenol 43 with either an alkyl halide or an appropriately substituted epoxide to yield nitro derivatives 46. Alternatively, when M, Q=$CR^3$ or N, intermediate 46 can be prepared via SNAr displacement of an aryl halide such as 47 with an appropriate alcohol or amine 48 in the presence of base. Reduction of intermediate 46 using methods commonly used in the literature, such as $H_2$/Pd—C or Sn/HCl, can provide amines 8a.

In the case when amines 8 are defined as 8a, an appropriately substituted cyclic amine 50 is reacted with haloarene or haloheteroarene 49 to afford compounds 51, which after reduction as indicated above, can yield amines 52.

4,5-Dihydropyrrolo[3,4-c]pyrazol-6(2H)-ones (IB) can be prepared by following a sequence shown in Scheme 2. Hydrolysis of the $R^{14}$ ester of diester 5 to the acid 11 followed by amide bond formation by coupling with amine 8 yields amide 12. Reduction of the $R^{15}$ ester of amide 12 and then following a sequence similar to the one shown in Scheme 1 can afford the desired 4,5-dihydropyrrolo[3,4-c]pyrazol-6(2H)-ones (IB).

Scheme 3 describes an alternative method to access compounds of the invention type IB. Pyrazole aldehyde 17 can be prepared using procedures known in the literature (see for example, Sridhar, R., *Bioorg. Med. Chem. Lett.* (2004)). Reductive amination of ester 17 with either a protected amine, such as 4-methoxybenzylamine, or with an ammonia equivalent, followed by hydrolysis of the ester can yield amine-acid 19. Cyclization using standard coupling conditions followed by deprotection of the amine protecting group (P), if needed, affords free lactam 21. Lactam 21 can then be coupled with suitable bromides using Buchwald-type conditions or with boronic acids using Chart-Lam conditions to yield the desired compounds of the invention (IB).

A third alternative to access IB is shown in Scheme 4. Reductive amination of 17 with amine 8, followed by ester hydrolysis and cyclization as before yields the desired 4,5-dihydropyrrolo[3,4-c]pyrazol-6(2H)-ones (1B).

Scheme 5 describes a method to synthesize a sub-class of 5,6-dihydropyrrolo[3,4-d][1,2,3]triazol-4(2H)-ones of the type represented by IC. Commercially available 4-bromo-2-methoxy-bromophenol (26) can be reacted with benzyl bromide and reacted with commercially available 4-methoxy-1H-pyrrol-2(5H)-one (28) in the presence of CuI/base to yield aryllactam 29. Conversion of 29 to oxime 31 followed by reaction with suitable hydrazines yields intermediate 31, which on treatment with a dehydrating agent such as $PCl_5$ can afford 5,6-dihydropyrrolo[3,4-d][1,2,3]triazol-4(2H)-one 33. Removal of the benzyl group yields free phenol 34, which can be coupled with a suitable alkylating agent (35) to afford the desired 5,6-dihydropyrrolo[3,4-d][1,2,3]triazol-4(2H)-ones (36).

Compounds of the type IC in Scheme 6, where

is directly attached to a nitrogen substituent (for example, a substituted pyrrolidine), can be prepared by first assembling the corresponding bromide 40 in the usual manner (as described hereinbefore) followed by Buchwald-type couplings with appropriate amines.

Scheme 7 describes an alternative way of preparing compounds of the type IB. The acid-amine coupling can be executed on the acid-alcohol 41 and processed as in Scheme 2 to provide compounds IB.

Where $R^{2a}$ and/or $R^{2b}$ is a hydroxyl group, prodrug esters such as phosphates and amino acid esters can be prepared as exemplified in this application.

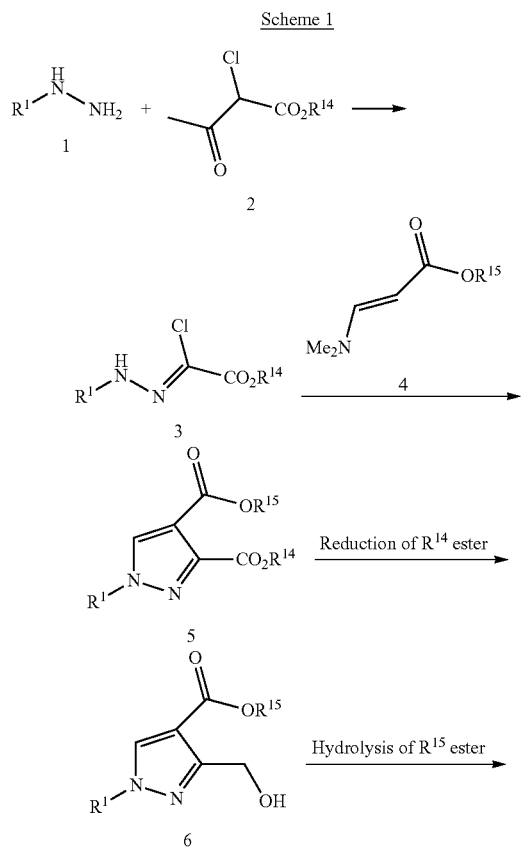

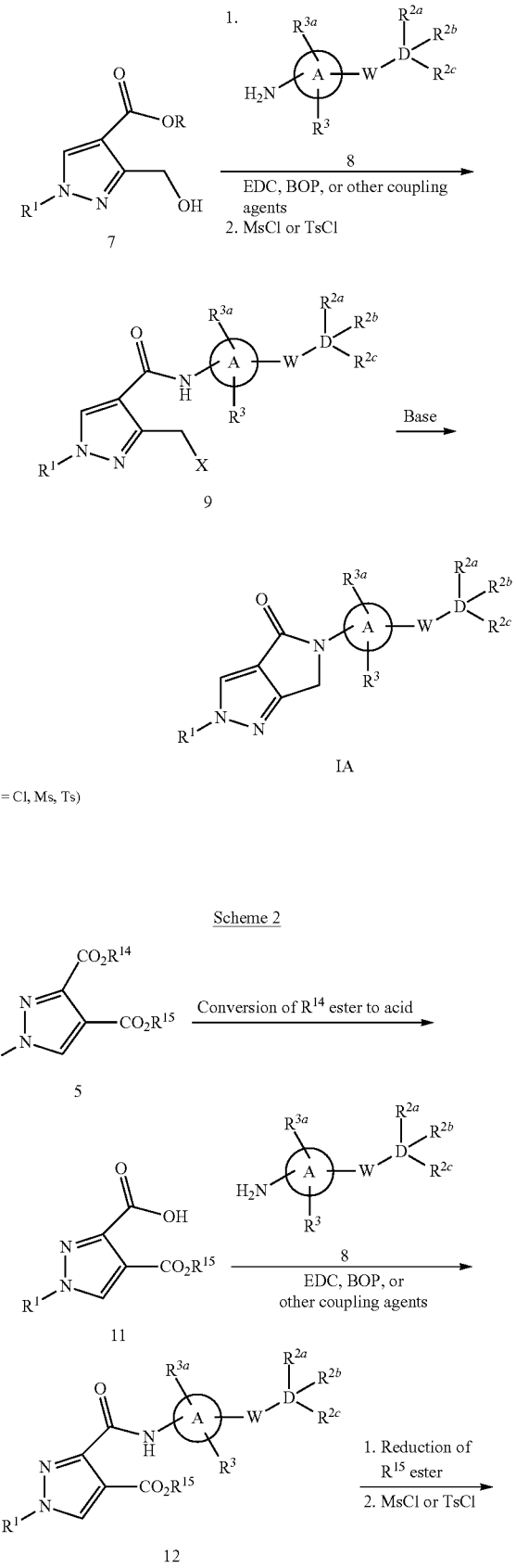

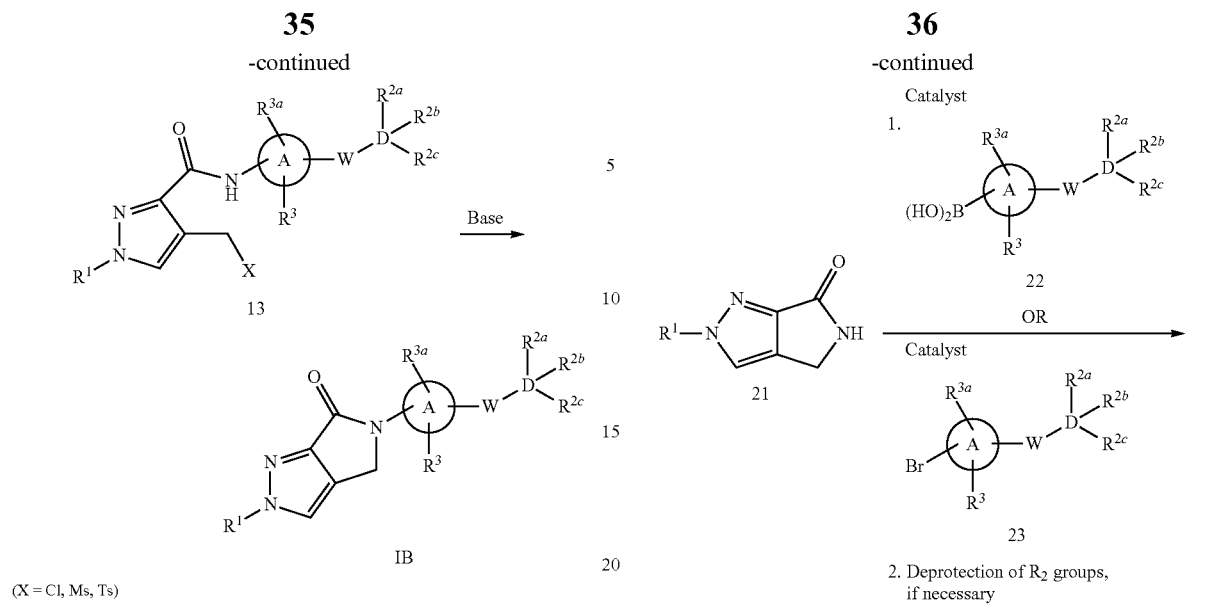
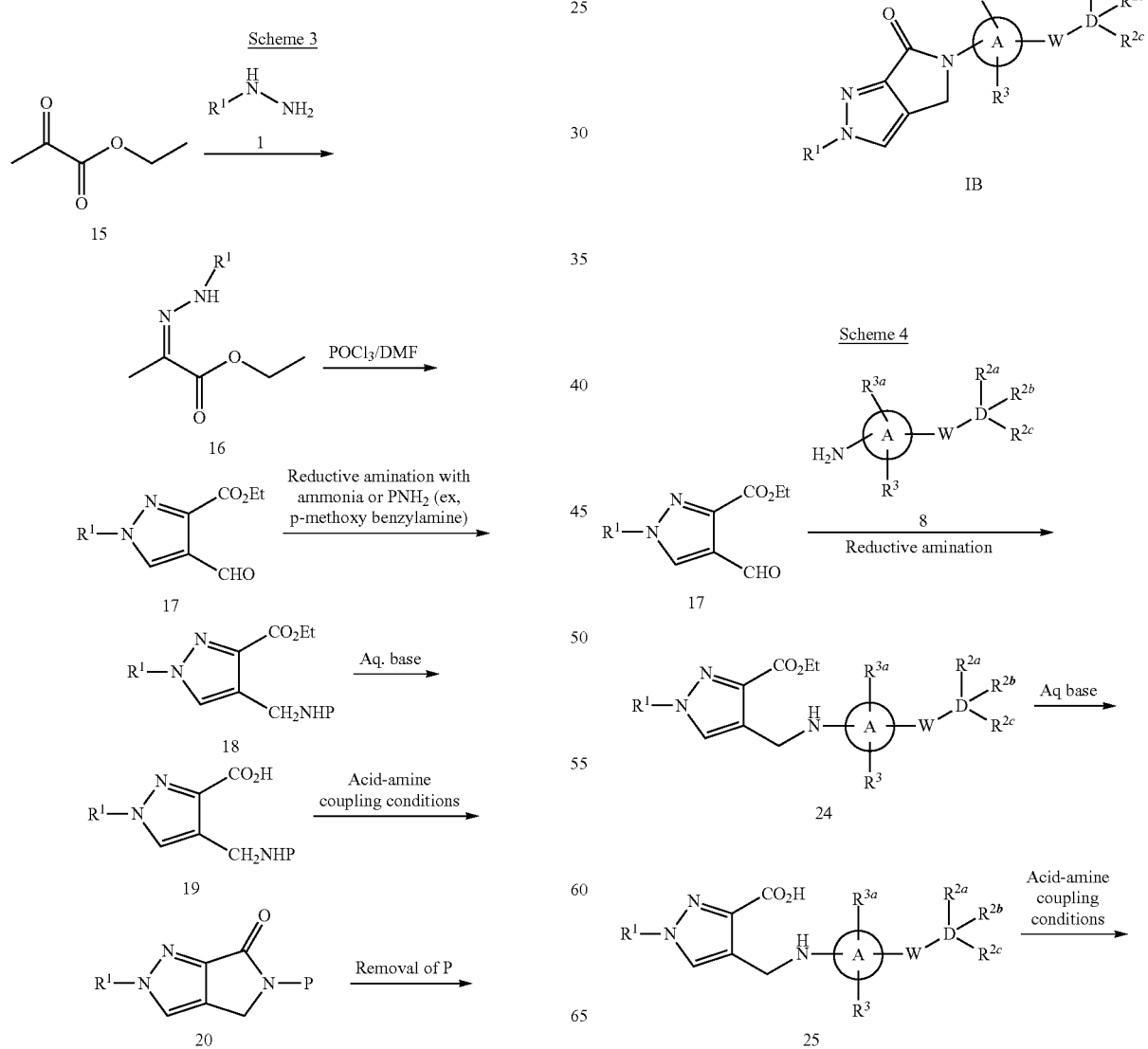

37
-continued
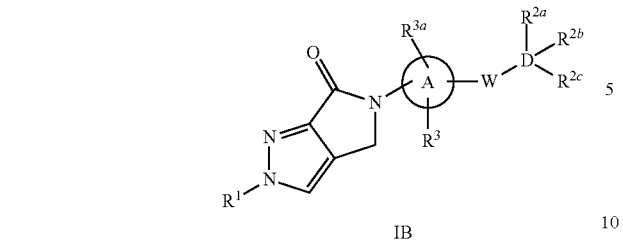
IB
Scheme 5
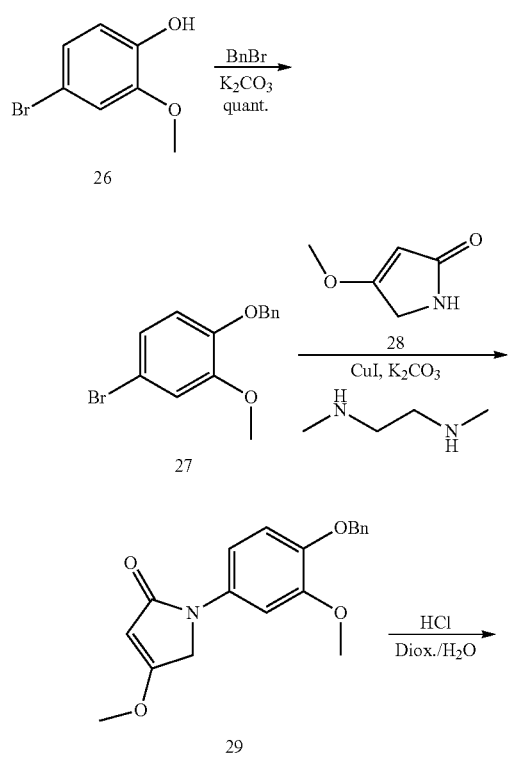
38
-continued
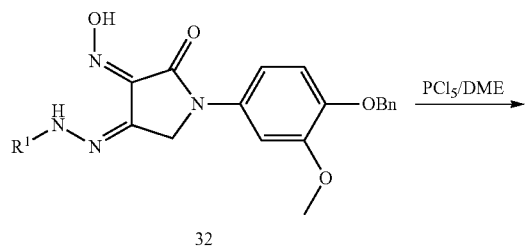
32
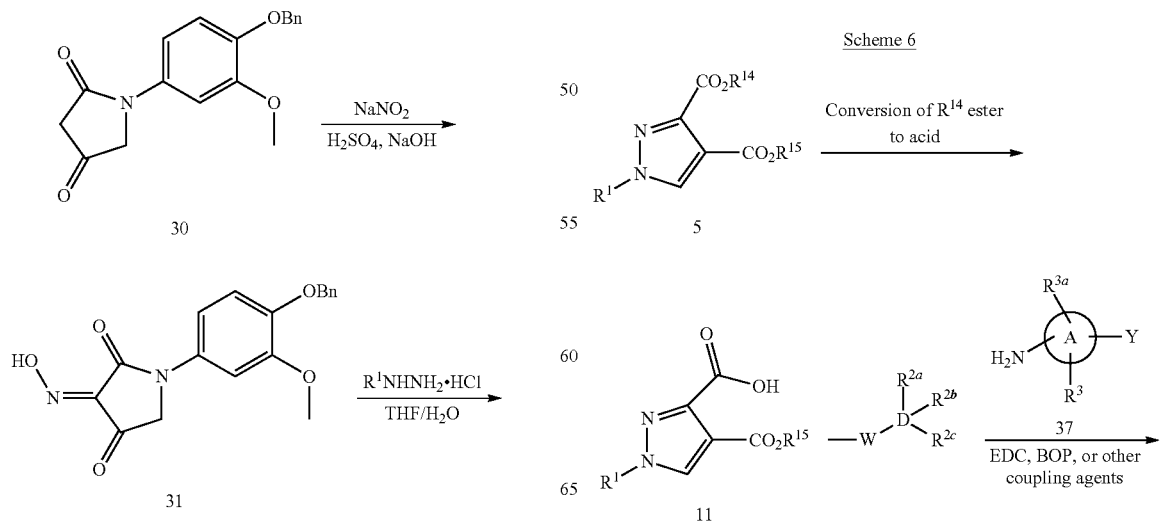

-continued
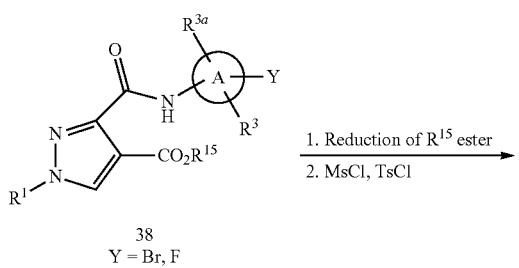
38
Y = Br, F
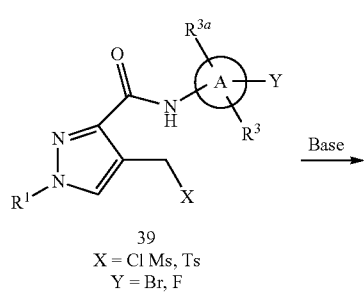
39
X = Cl Ms, Ts
Y = Br, F
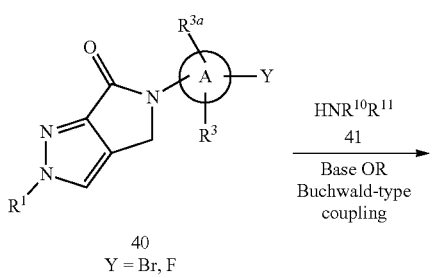
40
Y = Br, F
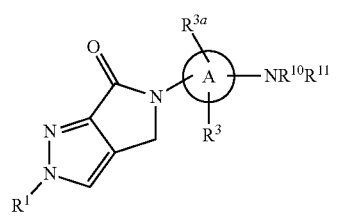
IC
Scheme 7
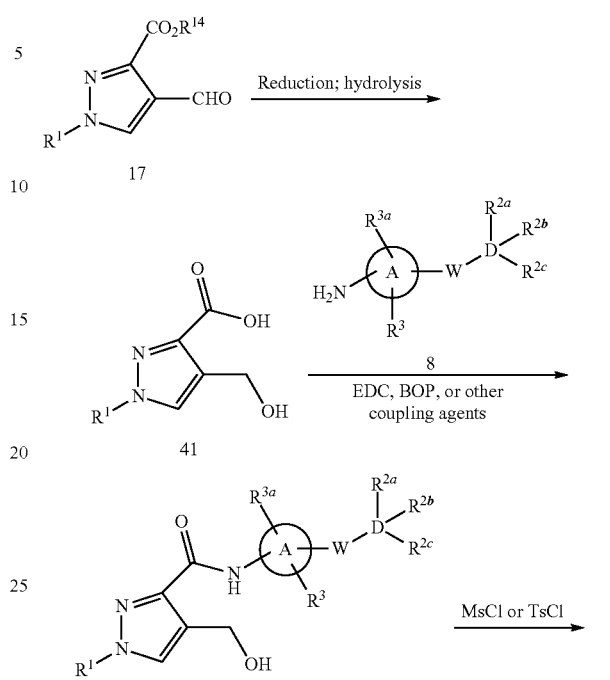
17
41
42
13
(X = Cl, Ms, Ts)
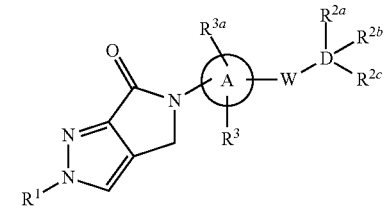
IB
Scheme 8A
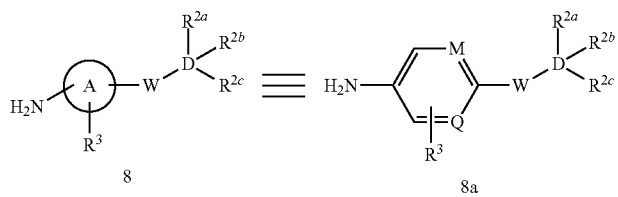

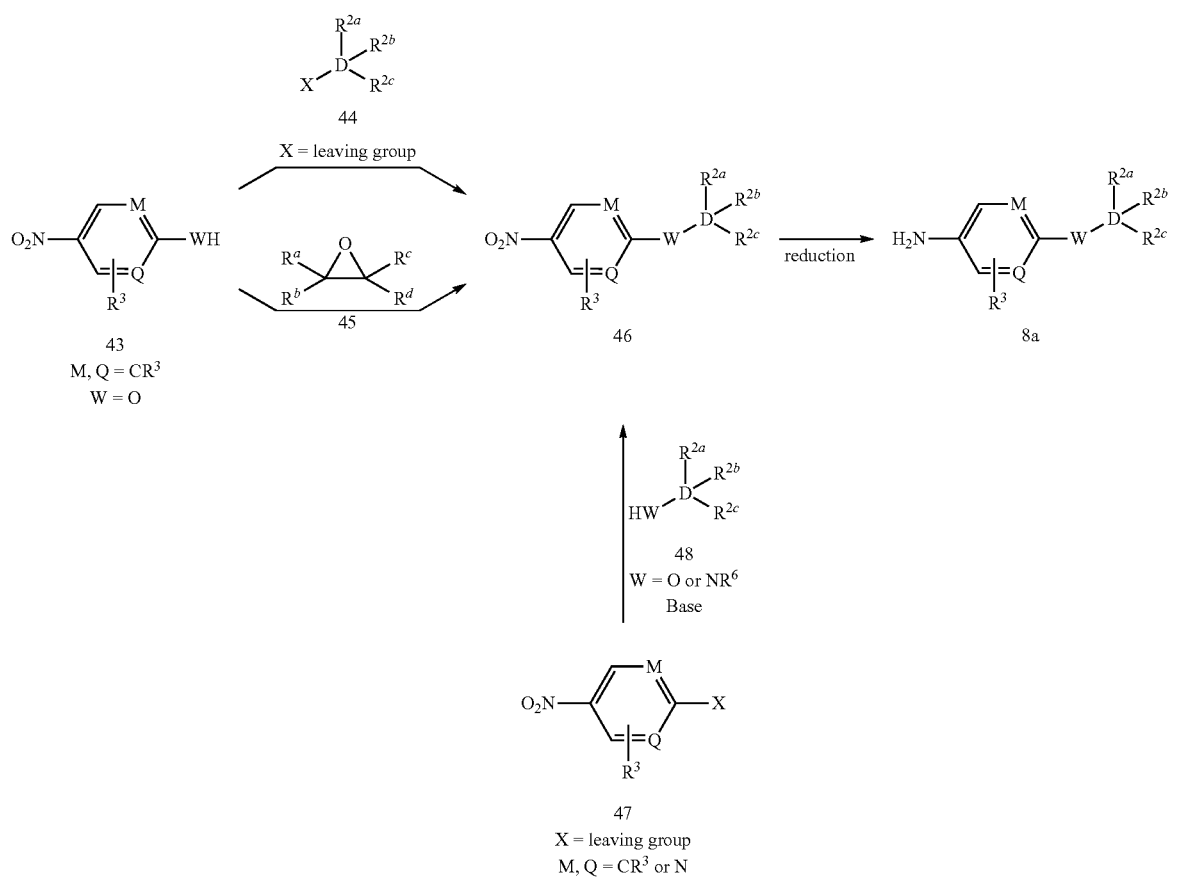

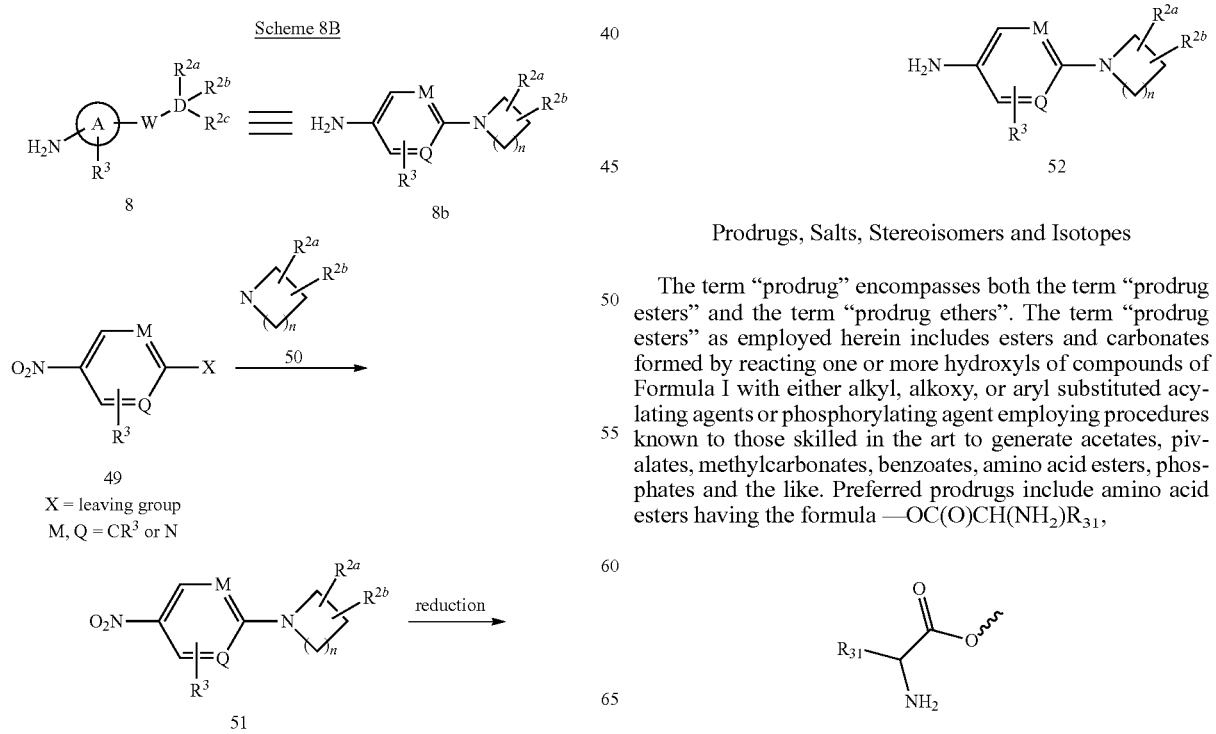

Prodrugs, Salts, Stereoisomers and Isotopes

The term "prodrug" encompasses both the term "prodrug esters" and the term "prodrug ethers". The term "prodrug esters" as employed herein includes esters and carbonates formed by reacting one or more hydroxyls of compounds of Formula I with either alkyl, alkoxy, or aryl substituted acylating agents or phosphorylating agent employing procedures known to those skilled in the art to generate acetates, pivalates, methylcarbonates, benzoates, amino acid esters, phosphates and the like. Preferred prodrugs include amino acid esters having the formula —OC(O)CH(NH$_2$)R$_{31}$, wherein $R_{31}$ is H or $C_1$ to $C_4$ alkyl, and phosphoric acid esters having the formula

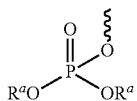

wherein Ra is H.

Additional examples of prodrug moieties of the present invention include

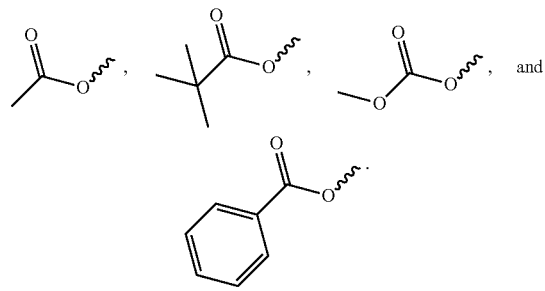

The term "prodrug ethers" include both phosphate acetals and O-glucosides. Representative examples of such prodrug ethers include

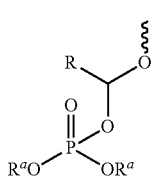 or 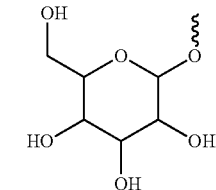

In the above formulae, R is alkyl or H and $R^a$ is H, alkyl, or benzyl.

Examples of specific prodrugs of the formula I compounds of the invention including prodrugs of compounds of formulae IA, IB and IC are set out below.

Example 10

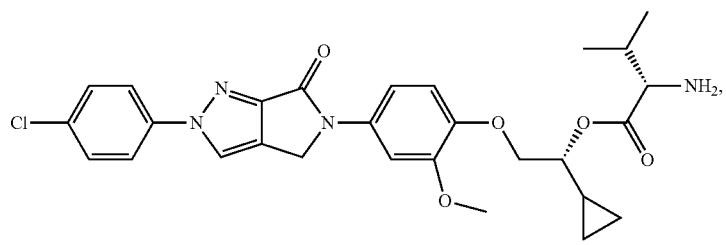

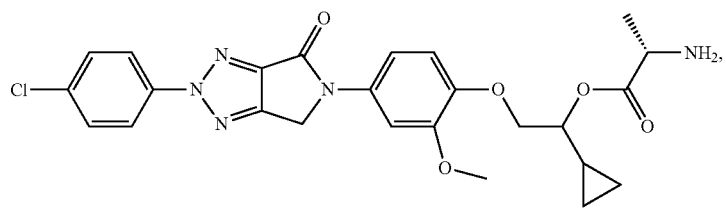

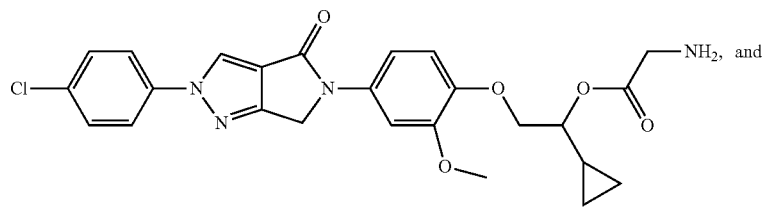

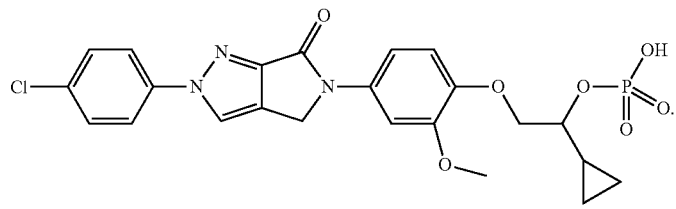

The compounds of Formula I can be present as salts, which are also within the scope of this invention. Pharmaceutically acceptable (i.e., non-toxic, physiologically acceptable) salts are preferred. If the compounds of Formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of Formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or trilower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula I or their pharmaceutically acceptable salts, are also included.

Preferred salts of the compounds of Formula I which contain a basic group include monohydrochloride, hydrogensulfate, methanesulfonate, phosphate, nitrate or acetate.

Preferred salts of the compounds of Formula I which contain an acid group include sodium, potassium and magnesium salts and pharmaceutically acceptable organic amines.

All stereoisomers of the compound of the instant application are contemplated, either in admixture or in pure or substantially pure form. The compound of the present application can have asymmetric centers at any of the carbon atoms including any one of the R substituents. Consequently, compound of Formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The present invention is intended to include all isotopes of atoms occurring in the present compounds of the invention. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Abbreviations

The following abbreviations are employed herein:

| | |
|---|---|
| Ph= | phenyl |
| Bn= | benzyl |
| t-Bu= | tertiary butyl |
| Me= | methyl |
| Et= | ethyl |
| TMS= | trimethylsilyl |
| TBS= | tert-butyldimethylsilyl |
| THF= | tetrahydrofuran |
| $Et_2O$= | diethyl ether |
| EtOAc= | ethyl acetate |
| DMF= | dimethyl formamide |
| MeOH= | methanol |
| BOP= | benzotriazol-1-yloxy-tris(dimethylamino)-phosphonium hexafluorophosphate |
| EDC= | 1-(3-dimethylaminopropyl)-3-ethylcarbodiimide HCl |
| MsCl= | methanesulfonyl chloride |
| TsCl= | toluenesulfonyl chloride |
| EtOH= | ethanol |
| i-PrOH= | isopropanol |
| HOAc or AcOH= | acetic acid |
| TFA= | trifluoroacetic acid |
| i-$Pr_2$NEt= | diisopropylethylamine |
| $Et_3$N= | triethylamine |
| DMAP= | 4-dimethylaminopyridine |
| $NaBH_4$= | sodium borohydride |
| n-BuLi= | n-butyllithium |
| Pd/C= | palladium on carbon |
| KOH= | potassium hydroxide |
| NaOH= | sodium hydroxide |
| LiOH= | lithium hydroxide |
| $K_2CO_3$= | potassium carbonate |
| $NaHCO_3$= | sodium bicarbonate |
| Ar= | argon |
| $N_2$= | nitrogen |
| min= | minute(s) |
| h or hr= | hour(s) |
| L= | liter |
| mL= | milliliter |
| μL= | microliter |
| g= | gram(s) |
| mg= | milligram(s) |
| mol= | moles |
| mmol= | millimole(s) |
| meq= | milliequivalent |
| RT= | room temperature |
| sat or sat'd= | saturated |
| aq.= | aqueous |
| TLC= | thin layer chromatography |
| HPLC= | high performance liquid chromatography |
| LC/MS= | high performance liquid chromatography/mass spectrometry |
| MS or Mass Spec= | mass spectrometry |
| NMR= | nuclear magnetic resonance |
| mp= | melting point |

HPLC-1: Sunfire C18 (4.6×150 mm) 3.5 micron, gradient 10 to 100% B:A for 12 min, then 3 min hold at 100% B.

Mobile phase A: 0.05% TFA in water:$CH_3CN$ (95:5)

Mobile phase B: 0.05% TFA in $CH_3CN$:water (95:5)

TFA Buffer pH=2.5; Flow rate:1 mL/min; Wavelength:254 nm, 220 nm.

HPLC-2: XBridge Phenyl (4.6×150 mm) 3.5 micron, gradient 10 to 100% B:A for 12 min, then 3 min hold at 100% B.

Mobile phase A: 0.05% TFA in water:$CH_3CN$ (95:5)

Mobile phase B: 0.05% TFA in $CH_3CN$:water (95:5)

EXAMPLES

The following Examples serve to better illustrate, but not limit, some of the preferred embodiments of the invention.

Example 1

(R)-2-(4-Chlorophenyl)-5-(4-(2-cyclopropyl-2-hydroxyethoxy)-3-methoxyphenyl)-5,6-dihydropyrrolo[3,4-c]pyrazol-4(2H)-one

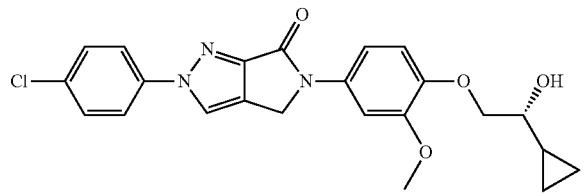 [SMILES: COc1cc(N2Cc3cn(-c4ccc(Cl)cc4)nc3C2=O)ccc1OC[C@H](O)C1CC1]

Example 1A

Benzyl 2-chloro-3-oxobutanoate

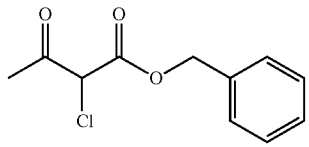

To a solution of benzyl 3-oxobutanoate (15 g, 78 mmol) in chloroform (150 mL) at 0° C. was added sulfuryl chloride (6.35 mL, 78 mmol) during a period of 20 min. The ice bath was removed and reaction mixture was allowed to warm to room temperature and stirred for 4 h. The solvent was evaporated and the crude product was diluted with EtOAc (250 mL). The organic layer was washed with $H_2O$ (100 mL), separated, dried over $MgSO_4$ and concentrated to give the desired product as a light yellow oil (17.6 g, 99% yield). $^1H$ NMR ($CDCl_3$) δ 2.31 (s, 3H), 4.80 (s, 1H), 5.25 (s, 2H), 7.30-7.42 (m, 5H). LCMS, $[M-H]^+=225.4$.

Example 1B (Z)-Benzyl 2-chloro-2-(2-(4-chlorophenyl)hydrazono)acetate)

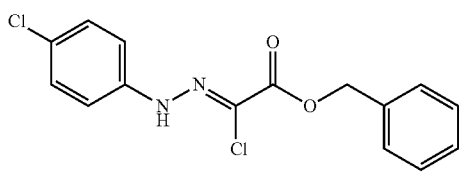 [SMILES: O=C(OCc1ccccc1)/C(Cl)=N/Nc1ccc(Cl)cc1]

To a mixture of 4-chloroaniline (9.28 g, 72.7 mmol) and 12 N hydrochloric acid (30.00 mL, 987 mmol), $H_2O$ (30 mL) at 0° C. was slowly added sodium nitrite (12.5 g, 181 mmol). The mixture was stirred at 0° C. for 30 min when it turned into a viscous solution (diazonium salt solution). To a solution of benzyl 2-chloro-3-oxobutanoate (17.5 g, 77 mmol) in MeOH/$H_2O$ (473 mL/203 mL) at room temperature was added sodium acetate (15 g, 183 mmol). The mixture was stirred at 0° C. for 5 min. The diazonium salt solution prepared above was added dropwise during a period of 5 min. After stirring at 0° C. for 10 min, the yellow-colored mixture was allowed to warm to room temperature and stirred over weekend. The mixture was filtered to give a solid which was further washed with $H_2O$ (100 mL), dried over vacuum to give the Example 1B as greenish powder (21.8 g, 87% yield). $^1H$ NMR ($CDCl_3$) δ 5.48 (s, 2H), 7.12-7.18 (m, 2H), 7.26-7.32 (m, 2H), 7.34-7.50 (m, 5H), 8.35 (s, 1H). LCMS, $[M-H]^+=321.6$.

Example 1C

3-Benzyl 4-ethyl 1-(4-chlorophenyl)-1H-pyrazole-3,4-dicarboxylate

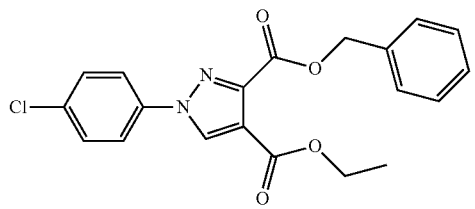 [SMILES: CCOC(=O)c1cn(-c2ccc(Cl)cc2)nc1C(=O)OCc1ccccc1]

A mixture of (Z)-benzyl 2-chloro-2-(2-(4-chlorophenyl)hydrazono)acetate (Example 1B, 21.8 g, 67.5 mmol), (E)-ethyl 3-(dimethylamino)acrylate (10.38 g, 72.5 mmol) in i-PrOH (388 mL), preheated to 55° C., was added triethylamine (10.11 mL, 72.5 mmol) dropwise. The mixture was then heated to 80° C. for 2 h. Solvent was evaporated and the crude product was diluted with $H_2O$ (150 mL) and extracted with EtOAc (300 mL). The organic layer was separated, dried over $MgSO_4$ and concentrated to give a crude product which was further purified by ISCO automated chromatography (330 g, Hexane/EtOAc, 100:0 to 70:30 gradient) to give Example 1C as a beige solid (11.9 g, 46% yield). $^1H$ NMR ($CDCl_3$) δ 1.28 (t, J=7.2 Hz, 3H), 4.29 (q, J=7.2 Hz, 2H), 5.43 (s, 2H), 7.12-7.18 (m, 2H), 7.30-7.50 (m, 5H), 7.65-7.70 (m, 2H), 8.34 (s, 1H). LCMS, $[M+H]^+=385.1$.

Example 1D

Ethyl 1-(4-chlorophenyl)-3-(hydroxymethyl)-1H-pyrazole-4-carboxylate

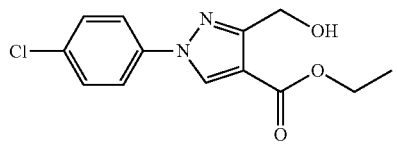 [SMILES: CCOC(=O)c1cn(-c2ccc(Cl)cc2)nc1CO]

To a solution of 3-benzyl 4-ethyl 1-(4-chlorophenyl)-1H-pyrazole-3,4-dicarboxylate (Example 1C, 3.57 g, 9.28 mmol) in THF (100 mL) was added $LiBH_4$ solution (7.89 mL, 15.77 mmol, 2M in THF). The reaction mixture was stirred at room temperature for 5 h. The resulting mixture was quenched with aqueous sat. NH₄Cl solution (10 mL). Solvent was evaporated and the crude product was diluted with H₂O (30 mL), extracted with EtOAc (150 mL). The organic layer was separated, dried over MgSO₄ and concentrated to give a crude product which was further purified by ISCO automated chromatography (42 g, Hexane/EtOAc, 100:0 to 60:40 gradient) to give the product as a white solid (1.5 g, 58% yield). ¹H NMR (CDCl₃) δ 1.40 (t, J=7.2 Hz, 3H), 4.38 (q, J=7.2 Hz, 2H), 3.98 (t, J=7.1 Hz, 1H). 4.88 (d, 7.1 Hz, 2H), 7.40-7.48 (m, 2H), 7.60-7.67 (m, 2H), 8.32 (s, 1H). LC-MS, [M+H]⁺= 281.0.

Example 1E 1-(4-Chlorophenyl)-3-(hydroxymethyl)-1H-pyrazole-4-carboxylic acid

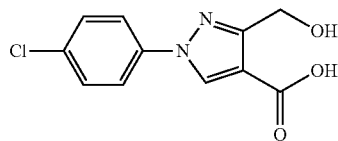 [SMILES: O=C(O)c1cn(-c2ccc(Cl)cc2)nc1CO]

A mixture of ethyl 1-(4-chlorophenyl)-3-(hydroxymethyl)-1H-pyrazole-4-carboxylate (Example 1D, 1.5 g, 5.34 mmol), sodium hydroxide (0.388 g, 9.70 mmol) and H₂O (50 mL) was heated at reflux for 2 h. After cooled down to room temperature, the reaction mixture was acidified with conc. HCl to pH about 5. The solid was collected via filtration, dried under vacuum to give the desired product as white solid (1.22 g, 90% yield). ¹H NMR (DMSO-d₆) δ 4.68 (s, 2H), 7.54-7.59 (m, 2H), 7.92-7.94 (m, 2H), 8.95 (s, 1H).

Example 1F (R)-tert-Butyl(1-cyclopropyl-2-(2-methoxy-4-nitrophenoxy)ethoxy)dimethylsilane

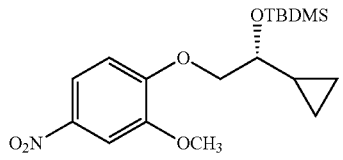 [SMILES: COc1cc([N+](=O)[O-])ccc1OC[C@H](O[Si](C)(C)C(C)(C)C)C1CC1]

To a solution of (R)-1-cyclopropyl-2-(2-methoxy-4-nitrophenoxy)ethanol (348 mg, 1.374 mmol) in CH₂Cl₂ (7.5 mL) at 0° C. was added tert-butyldimethylsilyl trifluoromethanesulfonate (545 mg, 2.061 mmol) and 2,6-lutidine (0.320 mL, 2.75 mmol). The resulting mixture was allowed to stir at 0° C. for 10 min, then stirred at room temperature for ½ h. Aq. NaHCO₃ solution (1 mL) was added. Organic solvent was evaporated and the crude product was diluted with H₂O (8 mL) and extracted with EtOAc (30 mL). The organic layer was separated, dried over MgSO₄ and concentrated to give a crude product which was further purified by silica gel chromatography (Hexane/EtOAc, 75:25) to give Example 1F as a light yellow solid (480 mg, 95% yield). ¹H NMR (CDCl₃) δ 0.00 (s, 3H), 0.08 (s, 3H), 0.28-0.35 (m, 2H), 0.40-0.50 (m, 2H), 0.81 (s, 9H), 0.85-0.99 (m, 1H), 3.58-3.62 (m, 1H), 3.86 (s, 3H), 4.00-4.10 (m, 2H) 6.88 (d, J=8.2 Hz, 1H), 7.69 (d, J=2.0 Hz, 1H), 7.83. (dd, J=8.2 Hz, 2.0 Hz, 1H).

Example 1G (R)-4-(2-(tert-Butyldimethylsilyloxy)-2-cyclopropylethoxy)-3-methoxyaniline

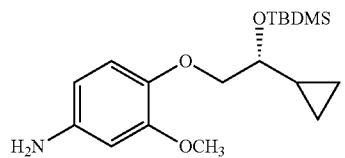

A mixture of (R)-tert-butyl (1-cyclopropyl-2-(2-methoxy-4-nitrophenoxy)ethoxy)dimethylsilane (Example 1F, 480 mg, 1.306 mmol), 10% palladium on active carbon (48 mg, 0.045 mmol) in EtOH (18 mL) was hydrogenated (1 atm) for 4 h. The catalyst was removed via filtration through a CELITE® pad. The filtrate was collected and concentrated to give Example 1G as light brown viscous oil (430 mg, 98% yield) which was used for next step without further purification. LC-MS, [M+H]⁺=338.2.

Example 1H (R)-4-(2-(tert-Butyldimethylsilyloxy)-2-cyclopropylethoxy)-3-methoxyaniline

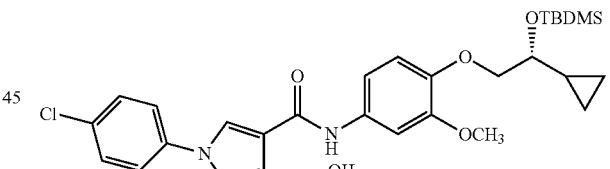

To a mixture of 1-(4-chlorophenyl)-3-(hydroxymethyl)-1H-pyrazole-4-carboxylic acid (Example 1E, 91 mg, 0.361 mmol) and Example 1G (122 mg, 0.361 mmol) in CH₂Cl₂ (10 mL) was added HOBt (66.4 mg, 0.434 mmol) and EDC (83 mg, 0.434 mmol). The resulting mixture was stirred at room temperature overnight. Solvent was evaporated and the crude product was dissolved in minimum amount CH₂Cl₂ and subjected to silica gel chromatography (Hexane/EtOAc, 75:25) to give Example 1H as a white solid (141 mg, 68% yield). ¹H NMR (CDCl₃) δ −0.05 (s, 3H), 0.00 (s, 3H), 0.25-0.28 (m, 2H), 0.34-0.40 (m, 2H), 0.78 (s, 9H), 0.85-0.92 (m, 1H), 3.5-3.60 (m, 1H), 3.75 (s, 3H), 3.79-3.90 (m, 3H) 4.84 (d, J=5.8 Hz), 2H), 6.70-6.74 (m, 1H), 6.82-6.88 (m, 1H), 7.30-7.50 (m, 5H), 8.30 (s, 1H), 9.45 (s, 1H). LC-MS, [M+H]⁺= 572.3.

Example 1I (R)-N-(4-(2-(tert-Butyldimethylsilyloxy)-2-cyclopropylethoxy)-3-methoxyphenyl)-3-(chloromethyl)-1-(4-chlorophenyl)-1H-pyrazole-4-carboxamide

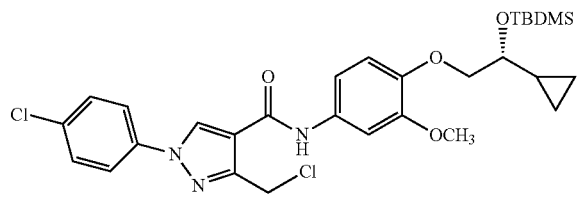 [SMILES: COc1cc(NC(=O)c2cn(-c3ccc(Cl)cc3)nc2CCl)ccc1OC[C@H](O[Si](C)(C)C(C)(C)C)C1CC1]

To a mixture of (R)-N-(4-(2-(tert-butyldimethylsilyloxy)-2-cyclopropylethoxy)-3-methoxyphenyl)-1-(4-chlorophenyl)-3-(hydroxymethyl)-1H-pyrazole-4-carboxamide (Example 1H, 141 mg, 0.246 mmol) in CH$_2$Cl$_2$ (8 mL) at room temperature under Ar was added methanesulfonyl chloride (0.029 mL, 0.370 mmol) and diisopropylethylamine (0.129 mL, 0.739 mmol). The resulting mixture was stirred at room temperature overnight. LC-MS indicated it is a mixture of chloride and mesylate. Solvent was evaporated and the residue diluted with EtOAc (20 mL) and washed with 0.5 N aq. HCl (3 mL). The organic layer was separated, dried over MgSO$_4$ and concentrated to give a crude product which was further purified by silica gel chromatography to give Example 1I as a white solid (122 mg, a mixture of chloride {LC-MS, [M+H]$^+$=590.1} and mesylate {LC-MS, [M+H]$^+$=650.1}.

Example 1J (R)-5-(4-(2-(tert-Butyldimethylsilyloxy)-2-cyclopropylethoxy)-3-methoxyphenyl)-2-(4-chlorophenyl)-5,6-dihydropyrrolo[3,4-c]pyrazol-4(2H)-one

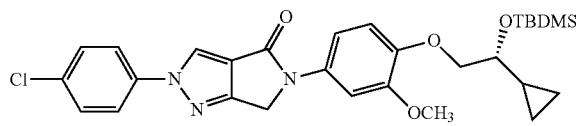

A mixture of Example 1I (122 mg, 0.207 mmol) and potassium carbonate (107 mg, 0.774 mmol) in DMF (1.5 mL) was heated at 95° C. for 3.5 h. The mixture was diluted with EtOAc (25 mL) and washed with H$_2$O (9 mL). The organic layer was separated and concentrated to give a crude product which was further purified by silica gel chromatography (Hexane/EtOAc, 75:25 to 50:50) to give a Example 1J as a white solid (80 mg, 70% yield). $^1$H NMR (CDCl$_3$) δ −0.03 (s, 3H), 0.00 (s, 3H), 0.20-0.28 (m, 2H), 0.30-0.41 (m, 2H), 0.78 (s, 9H), 0.85-0.95 (m, 1H), 3.5-3.60 (m, 1H), 3.78 (s, 3H), 3.85-3.95 (m, 3H), 4.73 (s, 2H), 6.80 (d, J=8.8 Hz, 1H), 6.85 (dd, J=8.2, 2.2 Hz, 1H), 7.32-7.38 (m, 2H), 7.48 (d, J=2.2 Hz, 1H), 7.54-7.57 (m, 2H), 8.04 (s, 1H).

Example 1K (R)-2-(4-Chlorophenyl)-5-(4-(2-cyclopropyl-2-hydroxyethoxy)-3-methoxyphenyl)-5,6-dihydropyrrolo[3,4-c]pyrazol-4(2H)-one

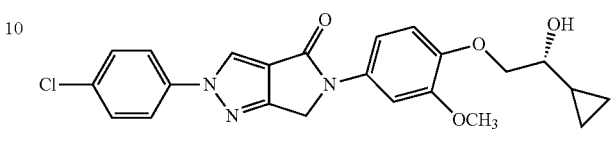

To a solution of Example 1J (80 mg, 0.144 mmol) in THF (5 mL) was added tetra-butylammonium fluoride (0.476 mL, 0.476 mmol, 1M solution in THF) and acetic acid (9.09 μL, 0.159 mmol). The resulting mixture was stirred at room temperature for 1.5 h. The mixture was heated at 63° C. for 1.5 h. The solvent was evaporated to give a crude product which was further purified by silica gel chromatography to give Example 1K as a white solid. This product was washed with Et$_2$O (10 mL) and subjected to filtration to give purer product as a white solid. (Example 1K, 20.3 mg, 31% yield). $^1$H NMR (CDCl$_3$) δ 0.18-0.25 (m, 1H), 0.35-0.41 (m, 1H), 0.42-0.60 (m, 2H), 0.83-0.92 (m, 1H), 2.78 (d, J=2.2 Hz, 1H), 3.19-3.30 (m, 1H), 3.82 (s, 3H), 3.92 (dd, J=9.8, 8.2 Hz, 1H), 4.12 (dd, J=9.8, 2.7 Hz, 1H), 4.78 (s, 2H), 6.85-6.93 (m, 2H), 7.40-7.44 (m, 2H), 7.56-7.62 (m, 3H), 8.09 (s, 1H). LC-MS, [M+H]$^+$=440.2.

Example 2

2-(4-Chlorophenyl)-5-(4-(2-hydroxypropoxy)-3-methoxyphenyl)-5,6-dihydropyrrolo[3,4-c]pyrazol-4(2H)-one

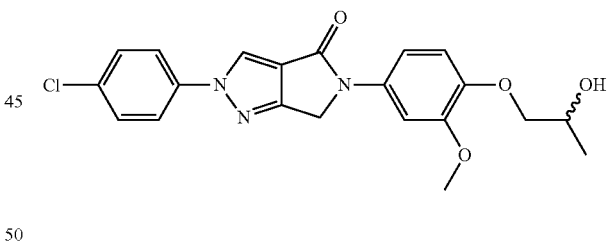

Example 2A

3-Methoxy-4-(2-((2-(trimethylsilyl)ethoxy)methoxy)propoxy)aniline

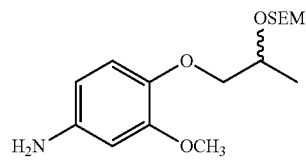

See Example 6B.

Example 2B 1-(4-Chlorophenyl)-3-(hydroxymethyl)-N-(3-methoxy-4-(2((2-(trimethylsilyl)ethoxy)methoxy)propoxy)phenyl)-1H-pyrazole-4-carboxamide

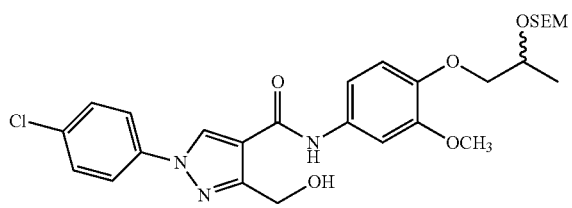

To a mixture of 1-(4-chlorophenyl)-3-(hydroxymethyl)-1H-pyrazole-4-carboxylic acid (Example 1E, 50 mg, 0.198 mmol) in $CH_2Cl_2$ (6 mL) was added Example 2A (78 mg, 0.237 mmol), HOBt (36.4 mg, 0.237 mmol) and EDC (45.5 mg, 0.237 mmol). The resulting mixture was stirred at room temperature. The solvent was evaporated and the crude product was dissolved in minimum amount of $CH_2Cl_2$ and subjected to ISCO automated chromatography (12 g, Hexane/EtOAc, 100:0 to 60:40 gradient) to give Example 2B as a white solid (80 mg, 72% yield). LCMS, $[M-H]^+=560.2$.

Example 2C 3-(Chloromethyl)-1-(4-chlorophenyl)-N-(3-methoxy-4-(2-((2-(trimethylsilyl)ethoxy)methoxy)propoxy)phenyl)-1H-pyrazole-4-carboxamide

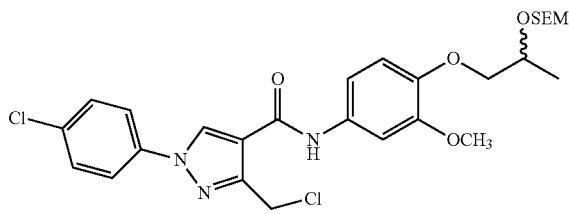

To a mixture of Example 2B (80 mg, 0.142 mmol) in $CH_2Cl_2$ (2 mL) at room temperature under Ar was added methanesulfonyl chloride (0.017 mL, 0.213 mmol) and triethylamine (0.060 mL, 0.427 mmol). The resulting solution was stirred at room temperature over the weekend. Solvent was evaporated and the residue was diluted with EtOAc (10 mL) and washed with 0.5 N aq HCl (1 mL). The organic layer was separated, dried over $MgSO_4$ and concentrated to give a crude product which was further purified by silica gel chromatography (Hexane/EtOAc, 50:50) to give Example 2C as a foam solid (43 mg, 52% yield). LCMS, $[M-H]^+=578.2$.

Example 2D 2-(4-Chlorophenyl)-5-(3-methoxy-4-(2-((2-(trimethylsilyl)ethoxy)methoxy)propoxy)phenyl)-5,6-dihydropyrrolo[3,4-c]pyrazol-4(2H)-one

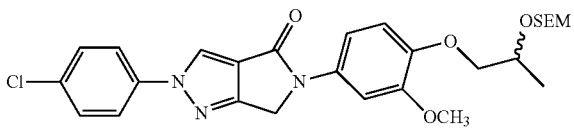

A mixture of Example 2C (44 mg, 0.076 mmol) and potassium carbonate (50 mg, 0.362 mmol) in DMF (0.6 mL) was heated at 95° C. for 2 h. The mixture was diluted with EtOAc (15 mL), washed with $H_2O$ (5 mL). The organic layer was separated and concentrated to give a crude product which was further purified by silica gel chromatography (Hexane/EtOAc, 75:25) to give Example 2D as a white solid (28 mg, 68% yield).

Example 2

2-(4-Chlorophenyl)-5-(4-(2-hydroxypropoxy)-3-methoxyphenyl)-5,6-dihydropyrrolo[3,4-c]pyrazol-4(2H)-one

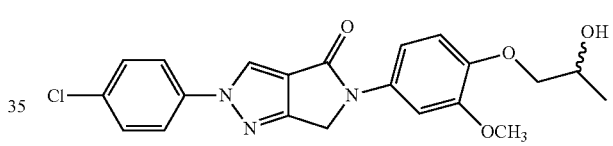

To a solution of Example 2D (28 mg, 0.051 mmol) in $CH_2Cl_2$ (2 mL) at 0° C. was added trifluoroacetic acid (60 μL, 0.779 mmol). The resulting mixture was stirred at 0° C. for 2.5 h. The solvent was evaporated to give a crude product which was further purified by silica gel chromatography (Hexane/EtOAc, 50:50 to 0:100) to give Example 2 as a white solid. The product was further washed with $Et_2O$ to give purer product as a white solid (13.9 mg, 62% yield). LC-MS, $[M+H]^+=414.0$. $^1H$ NMR ($CDCl_3$) δ 1.25 (d, J=6.5 Hz, 3H), 3.80 (dd, J=9.9, 8.8 Hz, 1H), 3.93 (s, 3H), 4.03 (dd, J=9.9, 3.3 Hz, 1H), 4.15-4.23 (m, 1H), 4.86 (s, 2H), 6.97 (s, 2H), 7.47-7.52 (m, 2H), 7.64-7.69 (m, 3H), 8.16 (s, 1H).

Example 3

2-(4-Chlorophenyl)-5-(4-(2-hydroxy-2-methylpropoxy)-3-methoxyphenyl)-5,6-dihydropyrrolo[3,4-c]pyrazol-4(2H)-one

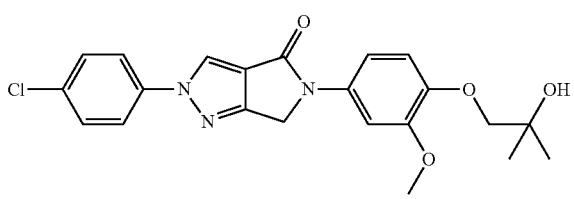 [SMILES: COc1cc(N2Cc3nn(-c4ccc(Cl)cc4)cc3C2=O)ccc1OCC(C)(C)O]

Example 3A (2-((1-(2-Methoxy-4-nitrophenoxy)-2-methylpropan-2-yloxy)methoxy)ethyl)trimethylsilane

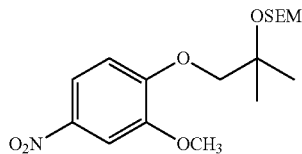

To a solution of 1-(2-methoxy-4-nitrophenoxy)-2-methyl-propan-2-ol (338 mg, 1.401 mmol) in CH$_2$Cl$_2$ (0.7 mL) at 0° C. under Ar was added SEM-Cl (0.497 mL, 2.80 mmol) and diisopropylethylamine (0.979 mL, 5.60 mmol). The resulting mixture was stirred at room temperature overnight. The crude product was diluted with H$_2$O (8 mL) and extracted with EtOAc (30 mL). The organic layer was separated, dried over MgSO$_4$ and concentrated to give a crude product which was further purified by silica gel chromatography (Hexane/EtOAc, 75:25) to give Example 3A as a pale yellow solid (456 mg, 88% yield). LC-MS, [M+Na]$^+$=394.1.

Example 3B

3-Methoxy-4-(2-methyl-2-((2-(trimethylsilyl)ethoxy)methoxy)propoxy)aniline

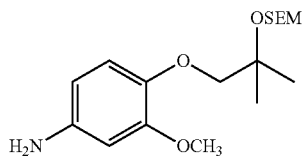

A mixture of (2-((1-(2-methoxy-4-nitrophenoxy)-2-methylpropan-2-yloxy)methoxy)ethyl)trimethylsilane (456 mg, 1.227 mmol), 10% palladium on active carbon (45 mg, 0.046 mmol) in EtOH (10 mL) was hydrogenated (1 atm) for 4 h. The catalyst was removed via filtration through a CELITE® pad. The filtrate was concentrated to give Example 3B as a light brown-colored viscous oil (369 mg, 88% yield) which was used for next step without further purification.

Example 3C 1-(4-Chlorophenyl)-3-(hydroxymethyl)-N-(3-methoxy-4-(2-methyl-2-((2-(trimethylsilyl)ethoxy)methoxy)propoxy)phenyl)-1H-pyrazole-4-carboxamide

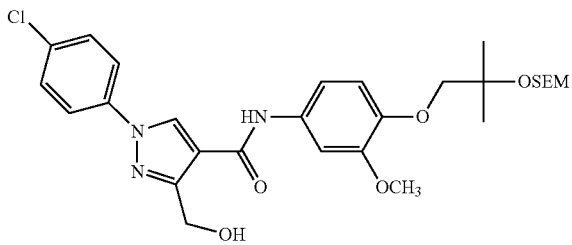

To a mixture of 1-(4-chlorophenyl)-3-(hydroxymethyl)-1H-pyrazole-4-carboxylic acid (Example 1E, 84 mg, 0.331 mmol) and Example 3B (113 mg, 0.331 mmol) in CH$_2$Cl$_2$ (10 mL) was added HOBt (60.8 mg, 0.397 mmol) and EDC (76 mg, 0.397 mmol). The resulting mixture was stirred at room temperature overnight. Solvent was evaporated and the crude product was dissolved in a minimum amount of CH$_2$Cl$_2$ and purified by silical gel chromatography (Hexane/EtOAc, 75:25) to give Example 3C as a white solid (116 mg, 61% yield). LC-MS, [M+H]$^+$=574.2.

Example 3D 3-(Chloromethyl)-1-(4-chlorophenyl)-N-(3-methoxy-4-(2-methyl-2-((2-(trimethylsilyl)ethoxy)methoxy)propoxy)phenyl)-1H-pyrazole-4-carboxamide

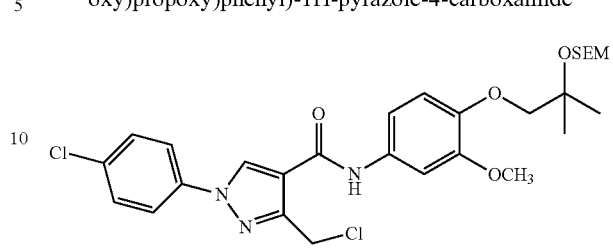

To a mixture of Example 3C (116 mg, 0.201 mmol) in CH$_2$Cl$_2$ (6 mL) at room temperature under Ar was added methanesulfonyl chloride (0.028 mL, 0.362 mmol) and diisopropylamine (0.105 mL, 0.604 mmol). The resulting solution was stirred at room temperature overnight. Solvent was evaporated and the residue was diluted with EtOAc (20 mL) and washed with 0.5 N aq HCl (3 mL). The organic layer was separated, dried over MgSO$_4$ and concentrated to give a crude product which was further purified by silica gel chromatography to give Example 3D as a foam solid (91 mg, 76% yield). LC-MS, [M+H]$^+$=592.4.

Example 3E 2-(4-Chlorophenyl)-5-(3-methoxy-4-(2-methyl-2-((2-(trimethylsilyl)ethoxy)methoxy)propoxy)phenyl)-5,6-dihydropyrrolo[3,4-c]pyrazol-4(2H)-one

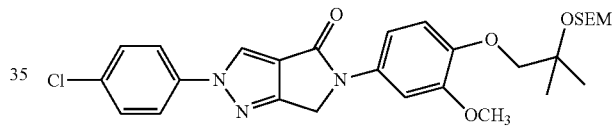

A mixture of Example 3D (91 mg, 0.153 mmol) and potassium carbonate (80 mg, 0.581 mmol) in DMF (1.5 mL) was heated at 95° C. for 3.5 h. The mixture was diluted with EtOAc (25 mL) and washed with H$_2$O (9 mL). The organic layer was separated and concentrated to give a crude product which was further purified by silica gel chromatography (Hexane/EtOAc, 75:25 to 66:33) to give Example 3E as a white solid (41 mg, 48%).

Example 3

2-(4-Chlorophenyl)-5-(4-(2-hydroxy-2-methylpropoxy)-3-methoxyphenyl)-5,6-dihydropyrrolo[3,4-c]pyrazol-4(2H)-one

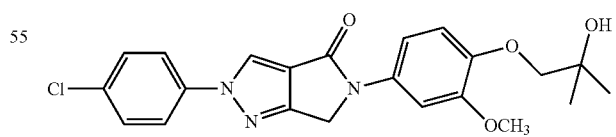

To a solution of Example 3E (41 mg, 0.073 mmol) in CH$_2$Cl$_2$ (2 mL) at 0° C. was added trifluoroacetic acid (60 μL, 0.779 mmol). The resulting mixture was stirred at 0° C. for 45 min. The solvent was evaporated to give a crude product which was further purified by silica gel chromatography (Hexane/EtOAc, 50:50 to 0:100) to give Example 3 as a white solid (10.2 mg, 32% yield). LC-MS, [M+H]$^+$=428.4. $^1$H NMR (CDCl$_3$) δ 1.28 (s, 6H), 3.77 (s, 2H), 3.84 (s, 3H), 4.78

(s, 2H), 6.80-6.92 (m, 2H), 7.38-7.43 (m, 2H), 7.55-7.57 (m, 1H), 7.57-7.62 (m, 2H), 8.09 (s, 1H).

Example 4

1-(4-(2-(4-Chlorophenyl)-4-oxopyrrolo[3,4-c]pyrazol-5(2H,4H,6H)-yl)-2-methoxyphenoxy)propan-2-yl methanesulfonate

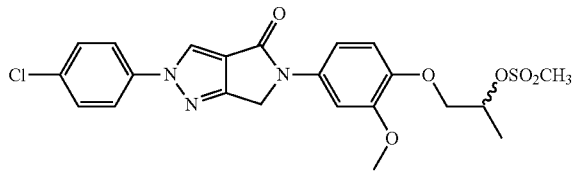

Example 4A 1-(4-Chlorophenyl)-3-(hydroxymethyl)-N-(4-(2-hydroxypropoxy)-3-methoxyphenyl)-1H-pyrazole-4-carboxamide

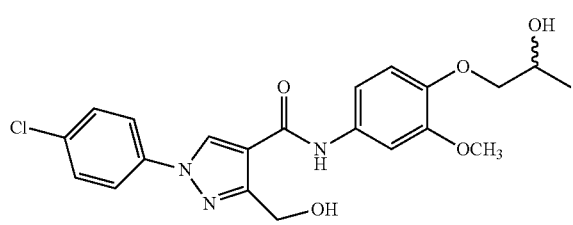 [SMILES: COc1cc(NC(=O)c2cn(-c3ccc(Cl)cc3)nc2CO)ccc1OCC(C)O]

To a mixture of 1-(4-chlorophenyl)-3-(hydroxymethyl)-1H-pyrazole-4-carboxylic acid (Example 1E, 56 mg, 0.222 mmol), 1-(4-amino-2-methoxyphenoxy)propan-2-ol (52.5 mg, 0.266 mmol) in CH$_2$Cl$_2$ (8 mL) was added HOBT (40.7 mg, 0.266 mmol) and EDC (51.0 mg, 0.266 mmol). The resulting mixture was stirred at room temperature for 24 h. Solvent was evaporated and crude product was dissolved in minimum amount of CH$_2$Cl$_2$ and subjected to ISCO automated chromatography (12 g, Hexane/EtOAc, 100:0 to 0:100 gradient) to give Example 4A as a white solid (72 mg, 75% yield). LC-MS, [M+H]$^+$=432.0.

Example 4B 1-(4-(1-(4-Chlorophenyl)-3-((methylsulfonyloxy)methyl)-1H-pyrazole-4-carboxamido)-2-methoxyphenoxy)propan-2-yl methanesulfonate

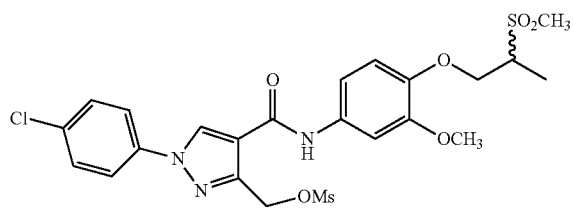 [SMILES: COc1cc(NC(=O)c2cn(-c3ccc(Cl)cc3)nc2COS(C)(=O)=O)ccc1OCC(C)S(C)(=O)=O]

To a mixture of 1-(4-chlorophenyl)-3-(hydroxymethyl)-N-(4-(2-hydroxypropoxy)-3-methoxyphenyl)-1H-pyrazole-4-carboxamide (Example 4A, 15 mg, 0.035 mmol) in CH$_2$Cl$_2$ (0.5 mL) at room temperature under Ar was added methanesulfonyl chloride (0.014 mL, 0.174 mmol) and triethylamine (0.034 mL, 0.243 mmol). The resulting solution was stirred at room temperature for ½ h. The crude product was diluted with H$_2$O (5 mL) and extracted with EtOAc (15 mL). The organic layer was separated, dried over MgSO$_4$ and concentrated to give a crude product which was further purified by chromatography (Hexane/EtOAc, 50:50) to give Example 4B as a white solid (10 mg, 49%). LC-MS, [M+H]$^+$=588.1.

Example 4

1-(4-(2-(4-Chlorophenyl)-4-oxopyrrolo[3,4-c]pyrazol-5(2H,4H,6H)-yl)-2-methoxyphenoxy)propan-2-yl methanesulfonate

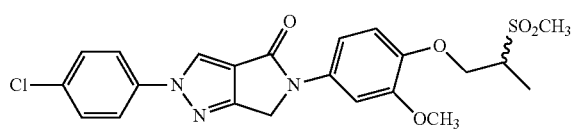 [SMILES: COc1cc(N2Cc3nn(-c4ccc(Cl)cc4)cc3C2=O)ccc1OCC(C)S(C)(=O)=O]

A mixture of 1-(4-(1-(4-chlorophenyl)-3-((methylsulfonyloxy)methyl)-1H-pyrazole-4-carboxamido)-2-methoxyphenoxy)propan-2-yl methanesulfonate (Example 4B, 10 mg, 0.017 mmol) and potassium carbonate (15 mg, 0.109 mmol) in DMF (0.5 mL) was heated at 85° C. for 30 min. The crude product was diluted with H$_2$O (8 mL) and extracted with EtOAc (25 mL). The organic layer was separated, dried over MgSO$_4$ and concentrated to give a crude product which was further purified by preparative HPLC (PHENOMENEX® Luna Axia column, 40-100% in 10 min gradient). The desired fraction was collected and concentrated under SPEEDVAC® to give Example 5 as white solid (2.85 mg, 32%). LC-MS, [M+H]$^+$=492.0. $^1$H NMR (CDCl$_3$) δ 1.52 (d, J=6.6 Hz, 3H), 3.19 (s, 3H), 3.88 (s, 3H), 3.92 (dd, J=9.8, 8.2 Hz, 1H), 4.12 (dd, J=9.8, 2.7 Hz, 1H), 4.78 (s, 2H), 5.10-5.17 (m, 1H), 6.90 (d, J=8.8 Hz, 1H), 6.96 (dd, J=8.8, 2.2 Hz, 1H), 7.44-7.52 (m, 2H), 7.60 (d, J=2.2 Hz, 1H), 7.63-7.70 (m, 2H), 8.20 (s, 1H).

Example 5

1-(4-(2-(4-Chlorophenyl)-6-oxopyrrolo[3,4-c]pyrazol-5(2H,4H,6H)-yl)-2-methoxyphenoxy)propan-2-yl methanesulfonate

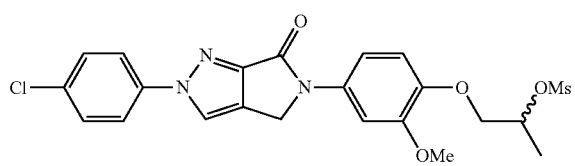 [SMILES: COc1cc(N2Cc3cn(-c4ccc(Cl)cc4)nc3C2=O)ccc1OCC(C)OS(C)(=O)=O]

Example 5A 1-(4-Chlorophenyl)-4-(ethoxycarbonyl)-1H-pyrazole-3-carboxylic acid

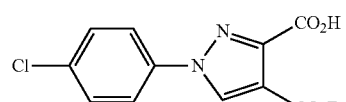

To a mixture of Example 1C [3-benzyl 4-ethyl 1-(4-chlorophenyl)-1H-pyrazole-3,4-dicarboxylate, 6.2 g, 16.11 mmol] in ethyl acetate (65 mL) was added 10% Pd/C (618 mg, 5.81 mmol) and the mixture hydrogenated at RT using a H2 balloon for 5 h. LC (5 h): 69:8:4 (DP:SM: deschloro side-product). The reaction mixture was filtered through CELITE®, washed with EtOAc, MeOH, then DCM (~500 mL) and evaporated to yield Example 5A (2.223 g, 7.54 mmol, 46.8% yield) as a pale brown solid.

Example 5B

Ethyl 1-(4-chlorophenyl)-3-(4-(2-hydroxypropoxy)-3-methoxyphenylcarbamoyl)-1H-pyrazole-4-carboxylate

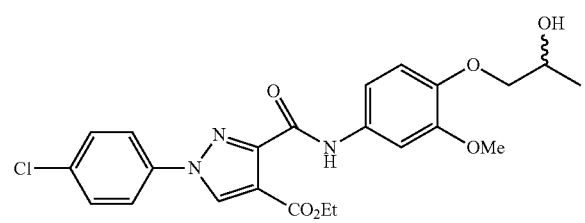

To a solution of Example 5A (6.5 mg, 0.022 mmol), 1-(4-amino-2-methoxyphenoxy)propan-2-ol (5.6 mg, 0.028 mmol), and BOP (14 mg, 0.032 mmol) in dichloromethane (1 mL) was added DIEA (15 µL, 0.086 mmol) and mixture stirred for an hour. Mixture was then diluted with DCM (10 mL) and washed with 1N HCl, brine, dried (Na$_2$SO$_4$), filtered and evaporated to yield 10 mg of crude brown solid, which after flash chromatography (4 g silica, 0% to 100% EtOAc-Hexanes) yielded Example 5B (3 mg, 6.33 gmol, 28.7% yield) as a white solid. LC-MS: [M+H]$^+$=474.1.

Example 5C 1-(4-Chlorophenyl)-4-(hydroxymethyl)-N-(4-(2-hydroxypropoxy)-3-methoxyphenyl)-1H-pyrazole-3-carboxamide

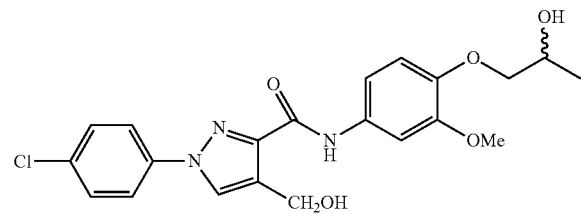 [SMILES: COc1cc(NC(=O)c2nn(-c3ccc(Cl)cc3)cc2CO)ccc1OCC(C)O]

To a solution of Example 5B (34 mg, 0.072 mmol) in THF (5 mL) was added 2M LiBH$_4$ in THF (100 µL, 0.200 mmol) dropwise and the resulting mixture was allowed to stir for 4.5 h, quenched with sat aq. NaHCO$_3$, extracted into EtOAc, and organic layer washed with brine, dried (Na$_2$SO$_4$), filtered, and evaporated to yield 34 mg of crude desired alcohol which was used as such for the next step. LC-MS: [M+H]$^+$=432.1.

Example 5D 1-(4-(4-(Chloromethyl)-1-(4-chlorophenyl)-1H-pyrazole-3-carboxamido)-2-methoxyphenoxy)propan-2-yl methanesulfonate

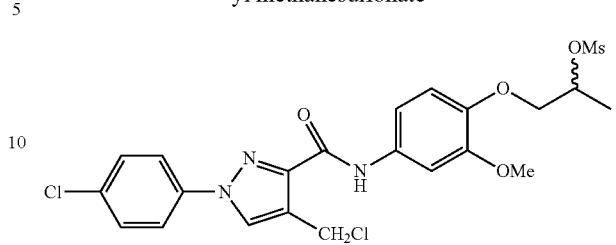

To a solution of Example 5C (34 mg, 0.079 mmol) in DCM (1 mL) was added TEA (0.072 mL, 0.514 mmol) followed by a solution of methanesulfonyl chloride (0.015 mL, 0.192 mmol) in 0.5 mL DCM. Mixture as allowed to stir overnight at RT. Mixture was evaporated and purified by flash chromatography (12 g silica, 0% to 100% EtOAc-Hexanes) to yield Example 5D (12 mg, 0.023 mmol, 29% yield) and Example 5E (5 mg, 0.011 mmol, 14% yield) as white solids.

Example 5D: LC-MS, [M+H]$^+$528.0. $^1$H NMR (CDCl$_3$, 400 MHz): Consistent with structure below:

Example 5D

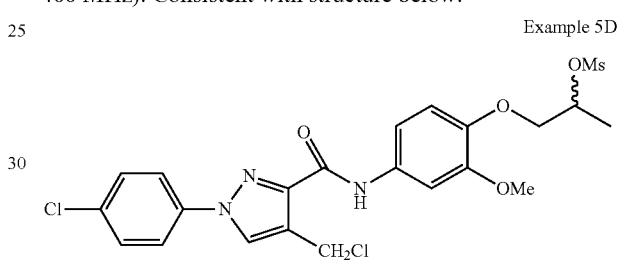

Example 5E: $^1$H NMR (CDCl$_3$, 400 MHz): Consistent with structure below. LC-MS, [M+H]$^+$=450.0.

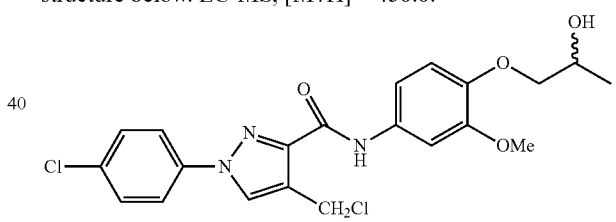

Example 5E 4-(Chloromethyl)-1-(4-chlorophenyl)-N-(4-(2-hydroxypropoxy)-3-methoxyphenyl)-1H-pyrazole-3-carboxamide Example 5

1-(4-(2-(4-Chlorophenyl)-6-oxopyrrolo[3,4-e]pyrazol-5(2H,4H,6H)-yl)-2-methoxyphenoxy)propan-2-yl methanesulfonate

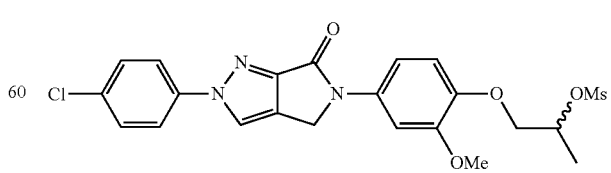

A mixture of Example 5D (10 mg, 0.019 mmol), K$_2$CO$_3$ (20 mg, 0.145 mmol) and DMF (1 mL) was stirred at RT, O.N. The mixture was then diluted with EtOAc (10 mL), washed with H₂O, brine, dried (Na₂SO₄), and evaporated under reduced pressure to obtain a white solid which was triturated in ether and filtered to yield Example 5 (6 mg, 0.012 mmol, 64.4% yield). LC-MS, [M+H]⁺=492.0. HPLC-1: Rt 8.621 min, purity >99%. HPLC-2: Rt 9.083 min, purity >99%. ¹H NMR (400 MHz, CDCl₃): δ 1.52 (d, J=6.6 Hz, 3H), 3.18 (s, 3H), 3.89 (s, 3H), 4.02-4.16 (m, 2H), 4.79 (s, 2H), 5.07-5.17 (m, 1H), 6.88 (d, J=8.8 Hz, 1H), 6.97 (dd, J=8.8, 2.6 Hz, 1H), 7.46 (m, 3H), 7.73 (d, J=8.8 Hz, 2H), 7.89 (s, 1H).

Example 6

2-(4-Chlorophenyl)-5-(4-(2-hydroxypropoxy)-3-methoxyphenyl)-4,5-dihydropyrrolo[3,4-c]pyrazol-6(2H)-one

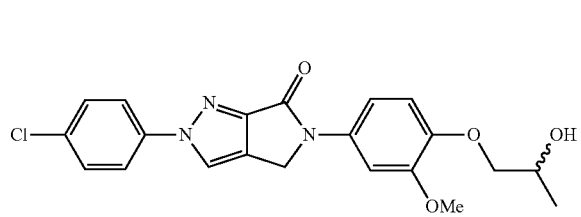 [SMILES: COc1cc(N2Cc3cn(-c4ccc(Cl)cc4)nc3C2=O)ccc1OCC(C)O]

Example 6A (2-((1-(2-Methoxy-4-nitrophenoxy)propan-2-yloxy)methoxy)ethyl)trimethylsilane

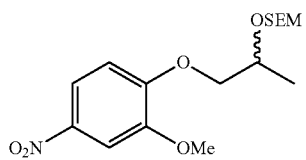

To a solution of 1-(2-methoxy-4-nitrophenoxy)propan-2-ol (1.537 g, 6.76 mmol) in DCM (20 mL) was added SEM-Cl (2.4 mL, 13.5 mmol) followed by DIPEA (4.7 mL, 27.1 mmol) dropwise under N₂. The mixture was stirred O.N. at RT., diluted with DCM (20 mL), washed with 1N HCl, brine, dried (Na₂SO₄), and evaporated under reduced pressure to obtain a yellow oil (3.79 g) which was purified by flash chromatography (40 g silica, 0% to 100% EtOAc-Hexanes) to yield. Example 6A (2.03 g, 5.68 mmol, 84% yield) as a yellow oil.

Example 6B

3-Methoxy-4-(2-((2-(trimethylsilyl)ethoxy)methoxy)propoxy)aniline

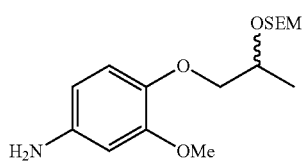

A mixture of Example 6A (2.0 g, 5.59 mmol) and 10% Pd—C (100 mg, 0.094 mmol) in MeOH (12 mL) was hydrogenated O.N. at RT using a H₂ balloon. LC-MS (O.N.): M+Na⁺=350.1. The reaction mixture was filtered and evaporated to yield Example 6B (1.811 g, 5.53 mmol, 99% yield) as an orange-pink oil.

Example 6C

Ethyl 1-(4-chlorophenyl)-3-(3-methoxy-4-(2-((2-(trimethylsilyl)ethoxy)methoxy)propoxy)phenylcarbamoyl)-1H-pyrazole-4-carboxylate

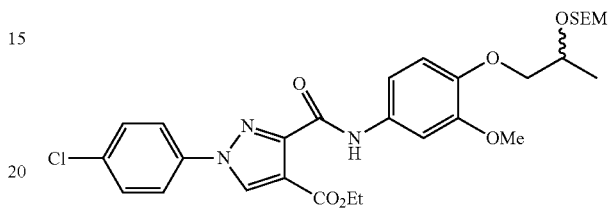

To a solution of Example 6A (173 mg, 0.587 mmol), Example 6B (247 mg, 0.754 mmol), and BOP (Advanced ChemTech) (395 mg, 0.893 mmol) in DCM (20 mL) at RT was added DIPEA (0.31 mL, 1.775 mmol) dropwise. LC and LCMS {[M+H]⁺=604.1} after 2 h indicated completion of reaction. The reaction mixture was allowed to stir for a total of 4.5 h and evaporated to obtain the crude product as a dark brown oil, which was purified by flash chromatography (40 g silica, 0% to 100% EtOAc-Hexanes) to yield Example 6C (380 mg, 0.629 mmol, 107% yield, contains some impurities according to ¹H NMR). Used as such for next step.

Example 6D 1-(4-Chlorophenyl)-4-(hydroxymethyl)-N-(3-methoxy-4-(2-((2-(trimethylsilyl)ethoxy)methoxy)propoxy)phenyl)-1H-pyrazole-3-carboxamide

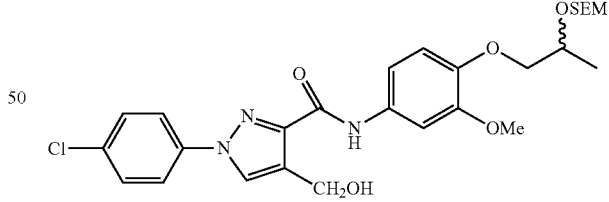

To a solution of Example 6C (355 mg, 0.587 mmol) in THF (10 mL) was added 2M LiBH₄ in THF (1 mL, 2.0 mmol) dropwise and the resulting mixture was allowed to stir for 2 h. The mixture was quenched with sat aq. NaHCO₃, extracted into EtOAc, and the organic layer was washed with brine, dried (Na₂SO₄), filtered, and evaporated to yield the crude alcohol, which was purified by flash chromatography (40 g silica, 0% to 100% EtOAc-Hexanes) to yield Example 6D (270 mg, 0.480 mmol, 82% yield) as a colorless oil (partially solidified). Yield=82% for 2 steps.

Example 6E 4-(Chloromethyl)-1-(4-chlorophenyl)-N-(3-methoxy-4-(2-((2-(trimethylsilyl)ethoxy)methoxy)propoxy)phenyl)-1H-pyrazole-3-carboxamide

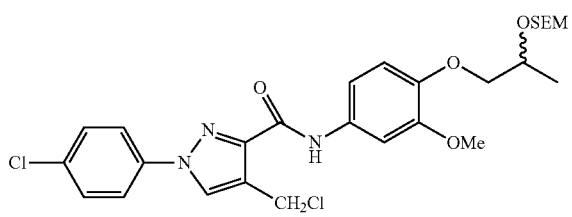

To a solution of Example 6D (270 mg, 0.480 mmol) and DIPEA (250 µL, 1.431 mmol) in DCM (10 mL) was added methanesulfonyl chloride (55 µL, 0.706 mmol) dropwise at RT and the mixture allowed to stir O.N. Evaporation followed by purification by flash chromatography (40 g silica, 0% to 100% EtOAc-Hexanes) yielded Example GE (197 mg, 0.339 mmol, 71% yield) as a colorless oil.

Example 6F 2-(4-Chlorophenyl)-5-(3-methoxy-4-(2-((2-(trimethylsilyl)ethoxy)methoxy)propoxy)phenyl)-4,5-dihydropyrrolo[3,4-c]pyrazol-6(2H)-one

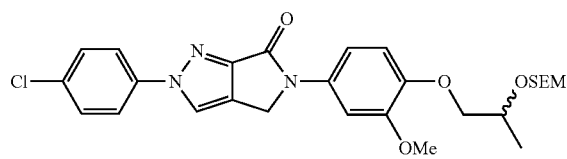

To a solution of Example 6E (72 mg, 0.124 mmol) in DMF (1 mL) was added. $K_2CO_3$ (77 mg, 0.557 mmol) and the mixture was stirred O.N. at R.T. After O.N. stirring, the mixture was treated with 1N HCl (10 mL) and extracted with EtOAc (50 mL). Organic layer was washed with brine (20 mL), dried ($Na_2SO_4$), filtered and evaporated to yield the crude product as a white solid, which was purified by flash chromatography (12 g silica, 0% to 100% EtOAc-Hexanes) to yield Example 6F (28 mg, 0.051 mmol, 42% yield) as a white solid. LC-MS, $[M+H]^+=544.2$.

Example 6

2-(4-Chlorophenyl)-5-(4-(2-hydroxypropoxy)-3-methoxyphenyl)-4,5-dihydropyrrolo[3,4-c]pyrazol-6(2H)-one

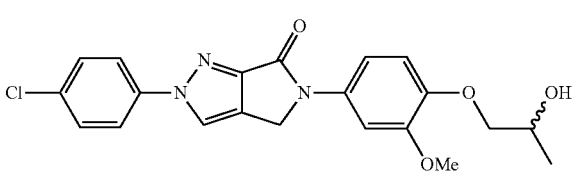 [SMILES: COc1cc(N2Cc3cn(-c4ccc(Cl)cc4)nc3C2=O)ccc1OCC(C)O]

To a solution of Example 6F (28 mg, 0.051 mmol) in DCM (2 mL) at 0° C. was added TFA (50 µL, 0.649 mmol) dropwise. The mixture was evaporated and purified by flash chromatography (12 g silica, 0% to 100% EtOAc-Hexanes) to yield Example 6 (12.5 mg, 0.029 mmol, 56% yield) and recovered SM (Example 6E, white solid, 6 mg, 21%). LC-MS, $[M+H]^+=414.1$. HPLC-1: Rt 7.43 min, purity=95%. HPLC-2: Rt 7.88 min, purity=94%. $^1$H NMR (CDCl$_3$, 400 MHz): $^1$H NMR (400 MHz, CDCl$_3$): δ 1.30 (d, J=6.2 Hz, 3H), 3.62-3.68 (m, 1H), 3.88 (s, 3H), 4.06-4.14 (m, 2H), 4.75 (s, 2H), 6.97 (dd, J=8.8, 2.2 Hz, 1H), 6.89 (d, J=8.8 Hz, 1H), 7.44 (d, J=8.8 Hz, 3H), 7.65 (dd, J=16, 2.2 Hz, 1H), 7.70 (d, J=8.8 Hz, 2H), 7.86 (s, 1H).

Example 7

2-(4-Chlorophenyl)-5-(3,4-dimethoxyphenyl)-4,5-dihydropyrrolo[3,4-c]pyrazol-6(2H)-one

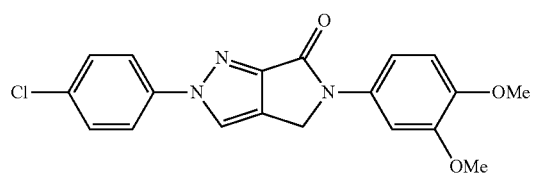 [SMILES: COc1ccc(N2Cc3cn(-c4ccc(Cl)cc4)nc3C2=O)cc1OC]

Example 7 was prepared in a manner analogous to Example 6 above, except that Example 6B was replaced by 3,4-dimethoxyaniline. LC-MS, $[M+H]^+=370.0$. HPLC-1: Rt 8.04 min, purity=96%. HPLC-2: Rt 8.68 min, purity=96%. $^1$H NMR (400 MHz, CDCl$_3$): δ 3.89 (s, 3H), 3.94 (s, 3H), 4.78 (s, 2H), 6.87 (d, J=8.8 Hz, 1H), 7.0 (dd, J=8.6, 2.4 Hz, 1H), 7.45 (d, J=8.8 Hz, 3H), 7.66 (d, J=2.2 Hz, 1H), 7.72 (d, J=8.8 Hz, 2H), 7.88 (s, 1H).

Example 8

2-(4-Chlorophenyl)-5-(4-(2-hydroxy-2-methylpropoxy)-3-methoxyphenyl)-4,5-dihydropyrrolo[3,4-c]pyrazol-6(2H)-one

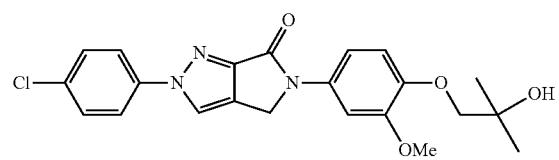 [SMILES: COc1cc(N2Cc3cn(-c4ccc(Cl)cc4)nc3C2=O)ccc1OCC(C)(C)O]

Example 8 was prepared in a manner analogous to Example 6 above, except that Example 6B was replaced by Example 3B.

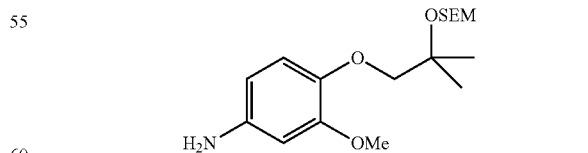

Example 3B

LC-MS, $[M+H]^+=428.0$. HPLC-1: Rt 7.76 min, purity >99%. HPLC-2: Rt 8.33 min, purity >99%. $^1$H NMR (400 MHz, CDCl$_3$): δ 1.35 (s, 6H), 3.83 (s, 2H), 3.91 (s, 3H), 4.77

(s, 2H), 6.96 (m, 2H), 7.27 (s, 1H), 7.45 (br d, J=7.5 Hz, 2H), 7.67 (br s, 1H), 7.72 (br d, J=7.5 Hz, 2H), 7.8 (br s, 1H).

Example 9

(R)-2-(4-Chlorophenyl)-5-(4-(2-cyclopropyl-2-hydroxyethoxy)-3-methoxyphenyl)-4,5-dihydropyrrolo[3,4-c]pyrazol-6(2H)-one

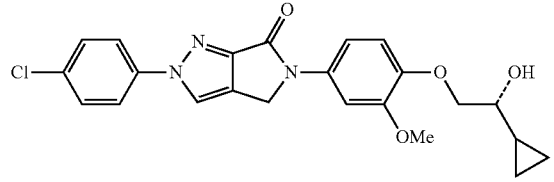 [SMILES: COc1cc(N2Cc3cn(-c4ccc(Cl)cc4)nc3C2=O)ccc1OC[C@H](O)C1CC1]

Example 9 was prepared in a manner analogous to Example 6 above, except that Example 6B was replaced by Example 1G [(R)-4-(2-(tert-butyldimethylsilyloxy)-2-cyclopropylethoxy)-3-methoxyaniline].

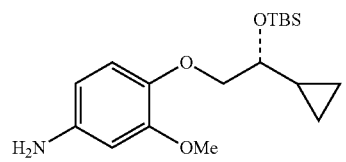

Example 1G

LC-MS, [M+H]$^+$=440.0. HPLC-1: Rt 7.97 min, purity >96%. HPLC-2: Rt 8.49 min, purity >97%. $^1$H NMR (CDCl$_3$, 400 MHz): δ 0.23-0.35 (m, 1H), 0.4-0.5 (m, 1H), 0.5-0.66 (m, 2H), 0.9-1.03 (m, 1H), 2.90 (s, 1H), 3.32 (t, J=7.5 Hz, 1H), 3.92 (s, 3H), 3.99 (t, J=9.2 Hz, 1H), 4.18 (dd, J=9.7, 2.2 Hz, 1H), 4.77 (s, 2H), 6.92-7.05 (m, 1H), 7.45 (d, J=8.4 Hz, 2H), 7.68 (s, 1H), 7.72 (d, J=8.8 Hz, 2H), 7.88 (s, 1H).

Example 10

(S)-((R)-2-(4-(2-(4-Chlorophenyl)-6-oxopyrrolo[3,4-c]pyrazol-5(2H,4H,6H)-yl)-2-methoxyphenoxy)-1-cyclopropylethyl) 2-amino-3-methylbutanoate, TFA salt

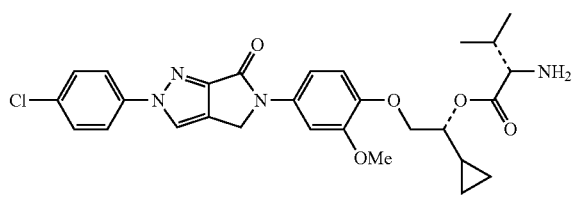 [SMILES: COc1cc(N2Cc3cn(-c4ccc(Cl)cc4)nc3C2=O)ccc1OC[C@H](OC(=O)[C@@H](N)C(C)C)C1CC1]

Example 10A (S)-((R)-2-(4-(2-(4-chlorophenyl)-6-oxopyrrolo[3,4-c]pyrazol-5(2H,4H,6H)-yl)-2-methoxyphenoxy)-1-cyclopropylethyl) 2-(tert-butoxycarbonylamino)-3-methylbutanoate

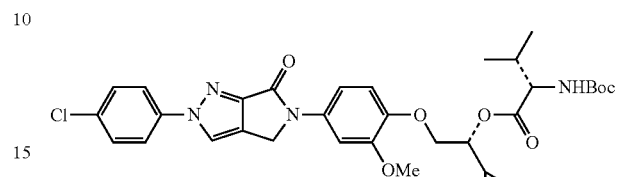

To a solution of Example 9 (61 mg, 0.139 mmol), DMAP (6 mg, 0.049 mmol), and (S)-2-(tert-butoxycarbonylamino)-3-methylbutanoic acid (40 mg, 0.184 mmol) in DCM (6 mL) was added DIC (30 µL, 0.193 mmol) at RT and the mixture stirred for 3 h at R.T. Evaporation, followed by purification by flash chromatography (12 g silica, 0% to 100% EtOAc-Hexanes) yielded Example 10A (103 mg, 0.161 mmol, 116% yield) as a white solid ($^1$H NMR indicated presence of some impurities).

Example 10

(S)-((R)-2-(4-(2-(4-chlorophenyl)-6-oxopyrrolo[3,4-c]pyrazol-5(2H,4H,6H)-yl)-2-methoxyphenoxy)-1-cyclopropyl ethyl) 2-amino-3-methylbutanoate, TFA salt

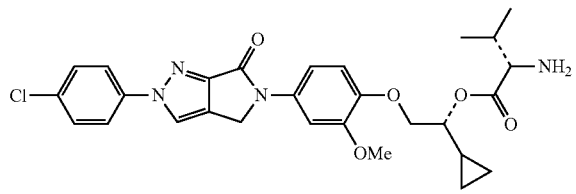 [SMILES: COc1cc(N2Cc3cn(-c4ccc(Cl)cc4)nc3C2=O)ccc1OC[C@H](OC(=O)[C@@H](N)C(C)C)C1CC1]

To a solution of Example 10A (89 mg, 0.139 mmol) in DCM (5 mL) was added TFA (1.5 mL, 19.47 mmol) dropwise and the mixture stirred for 40 min at RT. Evaporation followed by purification by Preparative HPLC (PHENOMENEX® Luna Axia 5µ C18 30×100 mm; 10 min gradient from 30% A: 70% B to 0% A:100% B (A=90% H$_2$O/10% MeOH+0.1% TFA); (B=90% MeOH/10% H$_2$O+0.1% TFA); detection at 220 nm) yielded Example 12, TFA salt (68 mg, 0.104 mmol, 75% yield) as a white solid. LC-MS, [M+H]$^+$= 539.1. HPLC-1: Rt 7.61 min, purity >99.6%. HPLC-2: Rt 6.42 min, purity >99.4%. $^1$H NMR (CD$_3$OD, 400 MHz): δ 0.45-0.58 (m, 2H), 0.6-0.75 (m, 2H), 1.12 (d, J=7.5 Hz, 3H), 1.14 (d, J=7.0 Hz, 3H), 1.2-1.34 (m, 1H), 2.28-2.42 (m, 1H), 3.87 (s, 3H), 3.95 (d, J=4.4 Hz, 1H), 4.29 (d, J=5.3 Hz, 2H), 4.66-4.74 (m, 1H), 4.87 (s, 2H), 7.02 (d, J=8.8 Hz, 1H), 7.14 (dd, J=8.8, 2.6 Hz, 1H), 7.52 (d, J=8.8 Hz, 2H), 7.58 (d, J=2.6 Hz, 1H), 7.85 (d, J=8.8 Hz, 2H), 8.31 (s, 1H).

Example 11

(R)-2-(4-Chlorophenyl)-5-(6-(3-hydroxypyrrolidin-1-yl)pyridin-3-yl)-4,5-dihydropyrrolo[3,4-c]pyrazol-6(2H)-one

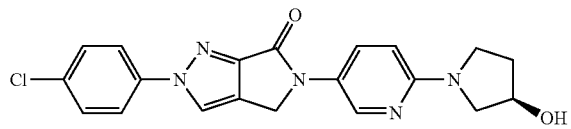 [SMILES: O=C1c2nn(-c3ccc(Cl)cc3)cc2CN1c1ccc(N2CC[C@@H](O)C2)nc1]

Example 11A 1-(5-Bromo-pyridin-2-yl)-pyrrolidin-3-ol

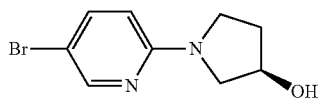 [SMILES: O[C@@H]1CCN(c2ccc(Br)cn2)C1]

To a solution of (R)-pyrrolidin-3-ol (0.3 g, 3.4 mmol) and 2-fluoro-5-bromopyridine (0.6 g, 3.4 mmol) in THF (4 mL) was added triethylamine (0.41 g, 4.1 mmol) dropwise. The resulting solution was irradiated for 30 min at 120° C. in microwave reactor. After removal of THF in vacuo, water was added and the mixture was extracted with ethyl acetate. The organic layer, after drying with sodium sulphate, was filtered, evaporated and purified by recrystallization from DCM to obtain Example 11A (0.36 g, 43% yield) as a white solid. LC-MS, [M+H]$^+$=243. $^1$H NMR (DMSO-$d_6$, 400 MHz): δ 8.10 (d, J=2.0 Hz, 1H), 7.62 (dd, J=2.56, 9.00 Hz, 1H), 6.42 (d, J=8.96 Hz, 1H), 4.96 (s, 1H), 4.37 (s, 1H), 3.45 (m, 3H), 3.26 (m, 1H), 2.02 (m, 1H), 1.89 (m, 1H).

Example 11B (Z)-Ethyl 2-(2-(4-chlorophenyl)hydrazono)propanoate

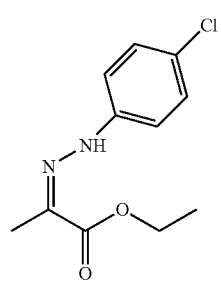 [SMILES: CCOC(=O)/C(C)=N\Nc1ccc(Cl)cc1]

To a solution of 4-chlorophenyl hydrazine hydrochloride (20 g, 111 mmol) in water (5 mL) was added sodium acetate (18.2 g, 222 mmol) followed by ethyl pyruvate (13 g, 111 mmol) and the resulting mixture was stirred for 30 min when a yellow solid precipitated out of solution. The yellow solid was filtered and dried to yield Example 1113 (21.1 g, 80% yield). LC-MS, [M+H]$^+$=241. $^1$H NMR (DMSO-$d_6$, 400 MHz): δ 9.93 (s, 1H), 7.33 (m, 2H), 7.28 (m, 2H), 4.21 (q, J=7.1 Hz, 2H), 2.04 (s, 3H), 1.28 (t, J=7.1 Hz, 3H).

Example 11C

Ethyl 1-(4-chlorophenyl)-4-formyl-1H-pyrazole-3-carboxylate

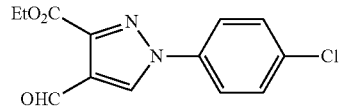

To dry DMF (13 mL) at 0° C. was added POCl$_3$ (40 g, 263 mmol) drop wise and mixture stirred for 30 min. Example 11C (21.1 g, 87 mmol) dissolved in dry DMF was added to the iminium salt solution at 0° C. and stirred for 16 h under nitrogen at RT. The reaction mixture was quenched and neutralized with crushed ice (500 g) and sodium bicarbonate mixture (10% aq. solution, 100 mL) to precipitate a pale yellow solid, which was then filtered, washed with water (150 mL), and dried to yield Example 11C (16 g, 66% yield). LC-MS, [M+H]$^+$=279. $^1$H NMR (DMSO-$d_6$, 300 MHz): δ 10.27 (s, 1H), 9.27 (s, 1H), 8.02 (d, J=8.8 Hz, 2H), 7.65 (d, J=8.8 Hz, 2H), 4.44 (q, J=7.1 Hz, 2H), 1.37 (t, J=7.1 Hz, 3H).

Example 11D

Ethyl 1-(4-chlorophenyl)-4-((4-methoxybenzylamino)methyl)-1H-pyrazole-3-carboxylate

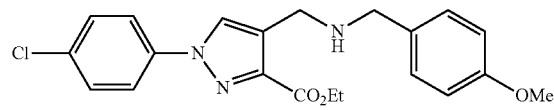

To a solution of Example 11C (16 g, 57 mmol) in dichloromethane (150 mL) was added 4-methoxy benzyl amine (7.8 g, 57 mmol) followed by 2 drops of acetic acid. The resulting reaction mixture was stirred at room temperature for 30 min. Sodium triacetoxyborohydride (18.2 g, 86 mmol) was then added and the mixture stirred for an hour. Reaction was quenched with 10% NaHCO$_3$ and extracted with dichloromethane (300 mL). Organic layer was washed with water (250 mL), brine (100 mL) and dried over Na$_2$SO$_4$. Filtration and concentration of organic layer yielded Example 11D (20 g, 88%) as a pale brown solid which was used as such for the next step. LC-MS, [M+H]$^+$=400. $^1$H NMR (DMSO-$d_6$, 300 MHz): δ 8.55 (s, 1H), 7.92 (d, J=8.8 Hz, 2H), 7.61 (d, J=8.8 Hz, 2H), 7.28 (d, J=8.6 Hz, 2H), 6.88 (d, J=8.7 Hz, 2H), 4.32 (q, J=6.96 Hz, 2H), 3.78 (s, 2H), 3.74 (s, 1H), 3.71 (s, 3H), 3.67 (s, 2H), 1.30 (t, J=6.96 Hz, 3H).

Example 11E 1-(4-Chlorophenyl)-4-(4-methoxybenzylamino)methyl)-1H-pyrazole-3-carboxylic acid

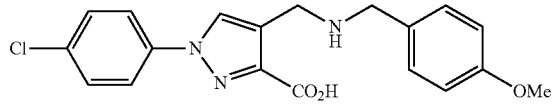 [SMILES: COc1ccc(CNCc2cn(-c3ccc(Cl)cc3)nc2C(=O)O)cc1]

To a solution of Example 11D (20 g, 50 mmol) in ethanol (200 mL) was added THF (100 mL) followed by 2N NaOH (55 mL 110 mmol) and the mixture was stirred at room temperature overnight. Reaction mixture was concentrated to remove THF and ethanol, neutralized with 1.5 N HCl (10 mL), filtered and dried to yield Example 11E (14 g, 75%). LC-MS, [M+H]$^+$=372. $^1$H NMR (DMSO-d$_6$, 400 MHz): δ 8.60 (s, 1H), 7.87 (d, J=8.8 Hz, 2H), 7.62 (d, J=8.8 Hz, 2H), 7.41 (d, J=8.4 Hz, 2H), 7.00 (d, J=8.8 Hz, 2H), 4.07 (m, 4H), 3.73 (s, 3H).

Example 11F 2-(4-Chlorophenyl)-5-(4-methoxybenzyl)-4,5-dihydropyrrolo[3,4-c]pyrazol-6(2H)-one

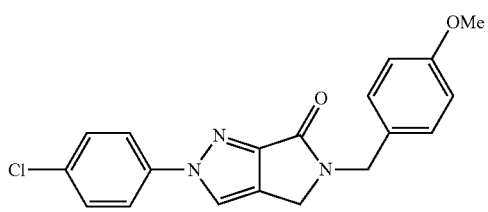 [SMILES: COc1ccc(CN2Cc3cn(-c4ccc(Cl)cc4)nc3C2=O)cc1]

A solution of Example 11E (14 g, 37 mmol) in dichloromethane (200 mL) was cooled to 5° C. EDCI HCl (14.3 g, 75 mmol), HOBT (4.7 g, 37 mmol) and triethyl amine (7.6 g, 75 mmol) were then added to it in that order. The resulting mixture was stirred at room temperature overnight and then quenched with 200 mL of 10% sodium bicarbonate solution. The mixture was extracted with ethyl acetate and the organic layer concentrated to yield a residue which was purified by flash chromatography (0 to 40% ethyl acetate: pet ether) to afford Example 11F (8 g, 60% yield). LC-MS, [M+H]$^+$=354. $^1$H NMR (DMSO-d$_6$, 400 MHz): δ 8.52 (s, 1H), 7.92 (d, J=8.92 Hz, 2H), 7.61 (d, J=8.92 Hz, 2H), 7.23 (d, J=8.52 Hz, 2H), 6.92 (d, J=8.6 Hz, 2H), 4.61 (s, 2H), 4.28 (s, 2H), 3.72 (s, 3H).

Example 11G 2-(4-Chlorophenyl)-4,5-dihydropyrrolo[3,4-c]pyrazol-6(2H)-one

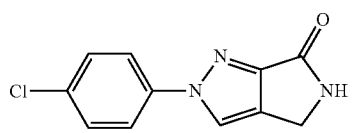 [SMILES: O=C1NCc2cn(-c3ccc(Cl)cc3)nc21]

To a solution of Example 11F (6 g, 17 mmol) in acetonitrile:water (60 mL:20 mL) was added ceric ammonium nitrite (37 g, 67 mmol) and the mixture stirred at RT for 3 h. Acetonitrile was removed under vacuum and the reaction mixture was then extracted with ethyl acetate (5×30 mL). Organic layer was washed with brine, dried over sodium sulfate, and concentrated to yield the crude product which was recrystallized from methanol to afford Example 11G (2 g, 50% yield) as a yellow solid. LC-MS, [M+H]$^+$=234. $^1$H NMR (DMSO-d$_6$, 400 MHz): δ 8.56 (s, 1H), 7.94 (d, J=8.4 Hz, 2H), 7.63 (d, J=8.8 Hz, 2H), 4.31 (s, 2H).

Example 11

(R)-2-(4-Chlorophenyl)-5-(6-(3-hydroxypyrrolidin-1-yl)pyridin-3-yl)-4,5-dihydropyrrolo[3,4-c]pyrazol-6(2H)-one

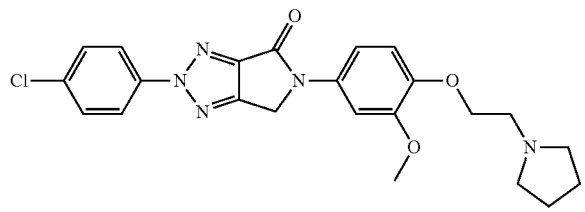 [SMILES: COc1cc(N2Cc3nn(-c4ccc(Cl)cc4)nc3C2=O)ccc1OCCN1CCCC1]

A mixture of Example 110 (60 mg, 0.26 mmol), Example 11A (75 mg, 0.31 mmol), N1,N2-dimethylethane-1,2-diamine (70 mg, 0.78 mmol), potassium phosphate tribasic (160 mg, 0.78 mmol) and copper(I) iodide (50 mg, 0.26 mmol) in dioxane (5.0 mL) was stirred at 115° C. overnight. The precipitate was filtered and the filtrate concentrated under reduced pressure. The crude product was purified by flash chromatography (0-0.5% methanol in DCM) to yield Example 14 (10 mg, 10% yield) as a pale yellow solid. LC-MS, [M+H]$^+$=396. $^1$H NMR (DMSO-d$_6$, 400 MHz): δ 8.65 (s, 1H), 8.35 (s, 1H), 7.96 (d, J=8.36 Hz, 2H), 7.91 (d, J=8.76 Hz, 1H), 7.63 (d, J=8.3 Hz, 2H), 6.50 (d, J=9.0 Hz, 1H), 4.96 (s, 1H), 4.86 (s, 2H), 4.39 (s, 1H), 3.49 (m, 4H), 2.03 (m, 1H), 1.90 (m, 1H). HPLC-1: Rt 5.9 min, purity=96%. HPLC-2: Rt 7.1 min, purity=95%

Example 12

2-(4-Chlorophenyl)-5-(3-methoxy-4-(2-(pyrrolidin-1-yl)ethoxy)phenyl)-5,6-dihydropyrrolo[3,4-d][1,2,3]triazol-4(2H)-one

Example 12A 1-(Benzyloxy)-4-bromo-2-methoxybenzene

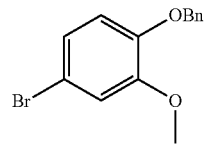

To a stirred suspension of 4-bromoguaiacol (1.51 g, 7.29 mmol) and potassium carbonate (3.00 g, 21.71 mmol) in MeCN (30 mL) was added benzyl bromide (1.0 mL, 8.24 mmol) dropwise at RT. After the addition was complete, stirring was continued at 70° C. for 13.5 h, the mixture was diluted with CH$_2$Cl$_2$ (100 mL) and washed with water (30 mL). The aqueous wash was back-extracted with CH$_2$Cl$_2$ (2×30 mL) and the combined organic layers were dried (Na$_2$SO$_4$) and evaporated. Chromatography (SiO$_2$ 230-400 mesh, 9/1 Hex/EtOAc) of the crude product gave Example 12A (2.16 g, quant.) as a white solid. LC-MS, [M+Na]$^+$=315, 317.

Example 12B 1-(4-(Benzyloxy)-3-methoxyphenyl)-4-methoxy-1H-pyrrol-2(5H)-oneoxylate

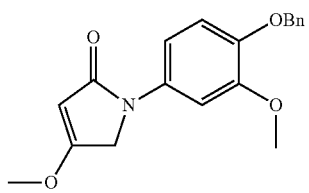 [SMILES: COC1=CC(=O)N(c2ccc(OCc3ccccc3)c(OC)c2)C1]

A flask containing Example 12A (1.09 g, 3.72 mmol), 4-methoxy-3-pyrrolin-2-one (517 mg, 4.57 mmol), potassium carbonate (powder, ~325 mesh, 1.03 g, 7.45 mmol) and copper(I) iodide (46 mg, 0.242 mmol) was evacuated and back-filled with argon. Toluene (4.0 mL) and N,N'-dimethylethylenediamine (50 µL, 0.465 mmol) were added under Ar and the mixture was stirred at 105° C. while stirring. for 18 h. The reaction mixture was filtered through a short pad of SiO$_2$ (230-400 mesh), eluting with 3/2 CH$_2$Cl$_2$/EtOAc (100 mL). The filtrates were evaporated and the residue was chromatographed (SiO$_2$ 230-400 mesh, 7/3 to 3/2 CH$_2$Cl$_2$/EtOAc) to provide Example 12B (914 mg, 76% yield) as a white solid. LC-MS, [M+H]$^+$=326.

Example 12C 1-(4-(Benzyloxy)-3-methoxyphenyl)pyrrolidine-2,4-dione

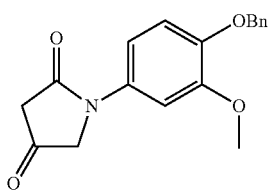 [SMILES: COc1cc(N2CC(=O)CC2=O)ccc1OCc1ccccc1]

To a stirred suspension of the Example 12B (310 mg, 0.953 mmol) in dioxane (4.2 mL) was added 5M hydrochloric acid (0.8 mL, 4.00 mmol) and the resulting solution was stirred at 38° C. for 24 h. The mixture was cooled to RT and partitioned between CH$_2$Cl$_2$ (50 mL) and water (3 mL). The aqueous layer was extracted with CH$_2$Cl$_2$ (2×15 mL) and the combined organic layers were dried (Na$_2$SO$_4$) and evaporated. Further drying under vacuum furnished Example 12C (300 mg, 94% yield) as a reddish solid. LC-MS, [M+H]$^+$=312.

Example 12D 5-(4-(Benzyloxy)-3-methoxyphenyl)-2-(4-chlorophenyl)-5,6-dihydropyrrolo[3,4-d][1,2,3]triazol-4(2H)-one

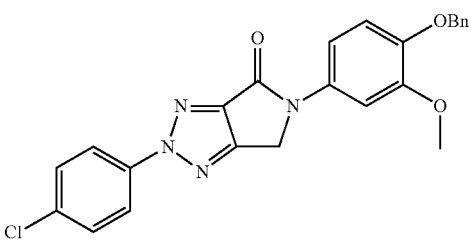 [SMILES: COc1cc(N2Cc3nn(-c4ccc(Cl)cc4)nc3C2=O)ccc1OCc1ccccc1]

To 1.5M aqueous sulfuric acid (0.83 mL, 1.245 mmol) at 0° C. was added dropwise a solution of Example 12C (299 mg, 0.884 mmol), sodium nitrite (95.0 mg, 1.336 mmol) and 1.0M aqueous sodium hydroxide (0.96 mL, 0.960 mmol) in THF (7.0 mL). The mixture was stirred at 0° C. for 30 min and then poured onto 5% aqueous NaHCO$_3$ (15 mL). The aqueous mixture was mixed with CH$_2$Cl$_2$ (50 mL) and filtered. The resulting biphasic solution was separated and the aqueous layer was extracted with Cl$_2$Cl$_2$ (2×30 mL). The combined organic layers were dried (Na$_2$SO$_4$) and evaporated to give a brown solid (299 mg). To a solution of this solid in THF (7.5 mL) was added a solution of 4-chlorophenylhydrazine hydrochloride (158 mg, 0.884 mmol) in water (2.4 mL) and the mixture was stirred at RT for 12 h. At this time, water (10 mL) was added and the resulting heterogeneous mixture was filtered. The collected solid was washed with water and taken up in CH$_2$Cl$_2$. The CH$_2$Cl$_2$ solution was dried (Na$_2$SO$_4$) and evaporated to give a brown solid (289 mg). To a 0° C. solution of the last solid in dry DME (2.0 mL), phosphorus pentachloride (154 mg, 0.725 mmol) was added in portions over 15 min. After the addition was complete, the mixture was stirred at RT for 3 h and then cooled to 0° C. The reaction mixture was poured onto cold 5% aqueous NaHCO$_3$ (20 mL) and the aqueous mixture was extracted with CH$_2$Cl$_2$ (4×30 mL). The combined organic extracts were dried (Na$_2$SO$_4$) and concentrated. The residue was chromatographed (SiO$_2$ 230-400 mesh, 95/5 CH$_2$Cl$_2$/ether) to give Example 12D (80 mg, 0.179 mmol, 20% yield) as a yellowish solid. LC-MS, [M+H]$^+$=447.

Example 12E 2-(4-Chlorophenyl)-5-(4-hydroxy-3-methoxyphenyl)-5,6-dihydropyrrolo[3,4-d][1,2,3]triazol-4(2H)-one

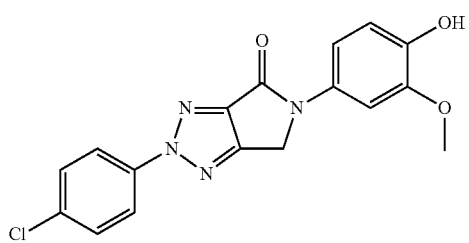 [SMILES: COc1cc(N2Cc3nn(-c4ccc(Cl)cc4)nc3C2=O)ccc1O]

To a mixture of Example 12D (57.4 mg, 0.128 mmol), thioanisole (0.16 mL, 1.349 mmol) and dichloromethane (0.5 mL) was added trifluoroacetic acid (2.0 mL, 26.9 mmol) at RT and the resulting solution was stirred at RT for 17 h. The solution was evaporated and the excess TFA was removed by co-evaporation with $CH_2Cl_2$ (6 mL), MeOH (8 mL) and $CH_2Cl_2$ (6 mL). The residue was taken up in MeOH and sonicated. The solid that formed was collected by filtration and rinsed with MeOH and ether. Drying under vacuum afforded Example 12E (35 mg, 76% yield) as a yellowish solid. LC-MS, $[M+H]^+=357$.

Example 12

2-(4-Chlorophenyl)-5-(3-methoxy-4-(2-(pyrrolidin-1-yl)ethoxy)phenyl)-5,6-dihydropyrrolo[3,4-d][1,2,3]triazol-4(2H)-one

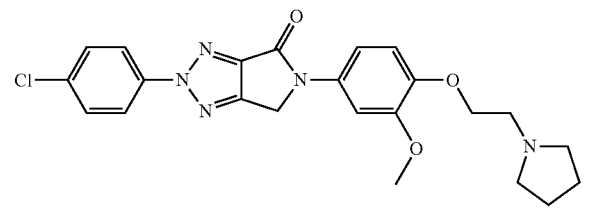 [SMILES: COc1cc(N2Cc3nn(-c4ccc(Cl)cc4)nc3C2=O)ccc1OCCN1CCCC1]

To a stirred suspension of Example 12E (15.3 mg, 0.043 mmol) and cesium carbonate (69.9 mg, 0.214 mmol) in MeCN (1.0 mL), heated at 78° C., was added 1-(2-chloroethyl)pyrrolidine hydrochloride (7.44 mg, 0.043 mmol). Stirring was continued at 78° C. for 12 h and then, the mixture was diluted with $CH_2Cl_2$ (20 mL). The mixture was washed with water (8.0 mL) and the aqueous layer was extracted with $CH_2Cl_2$ (2×10 mL). The combined organic layer was dried ($Na_2SO_4$) and concentrated. Chromatography ($SiO_2$ 230-400 mesh, 9/1 $CH_2Cl_2$/MeOH to 90/10/0.2 $CH_2Cl_2$/MeOH/ $NH_4OH$) of the crude product afforded Example 12 (12.1 mg, 61.5% yield) as a yellow solid. LC-MS, $[M+H]^+=454$. $^1H$ NMR ($CD_2Cl_2$, 400 MHz): δ 8.04 (d, J=8.8 Hz, 2H), 7.48 (d, J=2.6 Hz, 1H) 7.45 (d, J=8.8 Hz, 2H), 6.97 (dd, J=8.8, 2.6 Hz, 1H), 6.89 (d, J=8.8 Hz, 1H), 4.87 (s, 2H), 4.15 (t, J=5.3 Hz, 2H), 3.82 (s, 3H), 2.99 (t, J=5.3 Hz, 2H), 2.77 (m, 4H), 1.81 (m, 4H). HPLC-3: Rt 5.68 min, purity=99%.

Example 13

2-(4-Chlorophenyl)-5-(4-(2-hydroxy-2-methylpropoxy)-3-methoxyphenyl)-5,6-dihydropyrrolo[3,4-d][1,2,3]triazol-4(2H)-one

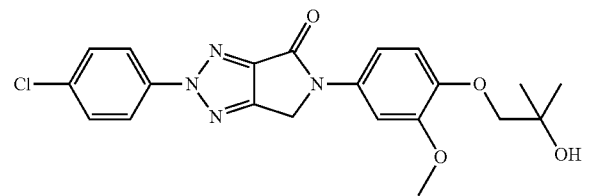 [SMILES: COc1cc(N2Cc3nn(-c4ccc(Cl)cc4)nc3C2=O)ccc1OCC(C)(C)O]

A mixture of Example 12E (6.5 mg, 0.018 mmol), MeCN (1.0 mL), water (0.1 mL), potassium carbonate (11 mg, 0.080 mmol) and 2,2-dimethyloxirane (40 μL, 0.437 mmol) was heated at 120° C. for 1.5 h in a microwave reactor. After cooling to RT, the mixture was partitioned between $CH_2Cl_2$ (30 mL) and water (5 mL). The aqueous layer was extracted with $CH_2Cl_2$ (2×10 mL) and the combined organic layers were dried ($Na_2SO_4$) and evaporated. Chromatography ($SiO_2$ 230-400 mesh, 95/5 $CHCl_3$/MeOH) of the crude product yielded Example 13 (5.3 mg, 67.2% yield) as a yellow solid. LC-MS, $[M+H]^+=429$. $^1H$ NMR ($CD_2Cl_2$, 400 MHz): δ 8.12 (d, J=8.8 Hz, 2H), 7.55 (d, J=2.6 Hz, 1H) 7.53 (d, J=8.8 Hz, 2H), 7.06 (dd, J=8.8, 2.6 Hz, 1H), 6.96 (d, J=8.8 Hz, 1H), 4.95 (s, 2H), 3.90 (s, 3H), 3.83 (s, 2H), 1.32 (2, 6H). HPLC-3: Rt 7.48 min, purity=99%.

Example 14

2-(4-Chlorophenyl)-5-(4-(2-cyclopropyl-2-hydroxyethoxy)-3-methoxyphenyl)-5,6-dihydropyrrolo[3,4-d][1,2,3]triazol-4(2H)-one

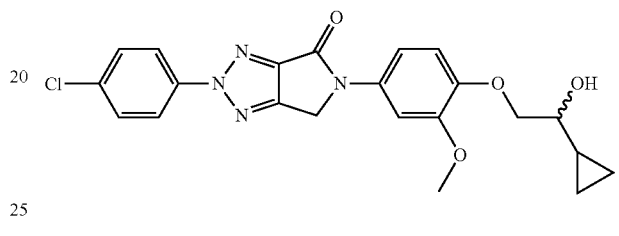

Example 14A

2-Cyclopropyl-2-oxoethyl 4-methylbenzenesulfonate

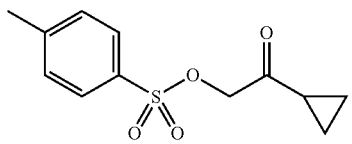 [SMILES: Cc1ccc(S(=O)(=O)OCC(=O)C2CC2)cc1]

Example 14A was prepared following a procedure reported in *Tetrahedron Lett.*, 33:7647 (1992).

Example 14B 2-(4-Chlorophenyl)-5-(4-(2-cyclopropyl-2-oxoethoxy)-3-methoxyphenyl)-5,6-dihydropyrrolo[3,4-d][1,2,3]triazol-4(2H)-one

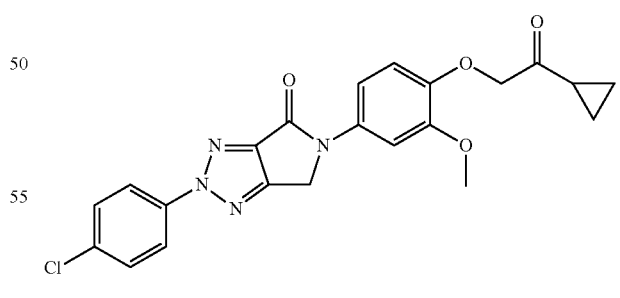

To a stirred suspension of Example 12E (13.2 mg, 0.037 mmol) and cesium carbonate (37 mg, 0.114 mmol) in MeCN (1.4 mL) was added Example 14A (16 mg, 0.063 mmol) and the mixture was heated at 80° C. for 3.5 h. At this time, an additional amount of Example 14A (7.0 mg, 0.027 mmol) was added and stirring was continued at 80° C. for 1.5 h. After cooling to RT, the mixture was diluted with $CH_2Cl_2$ (50 mL) and washed with 2% aqueous $NaHCO_3$ (10 mL). The aqueous wash was back-extracted with $CH_2Cl_2$ (2×10 mL) and the combined organic layers were dried ($Na_2SO_4$) and evaporated. Chromatography ($SiO_2$ 230-400 mesh, 9/1 $CH_2Cl_2$/Ether) of the crude product afforded Example 14B (12.8 mg, 77% yield) as a yellowish solid. LC-MS, $[M+H]^+$=439. $^1H$ NMR ($CDCl_3$, 400 MHz): δ 8.11 (d, J=8.8 Hz, 2H), 7.70 (d, J=2.6 Hz, 1H) 7.50 (d, J=8.8 Hz, 2H), 6.95 (dd, J=8.8, 2.6 Hz, 1H), 6.82 (d, J=8.8 Hz, 1H), 4.95 (s, 2H), 4.77 (s, 2H), 3.96 (s, 3H), 2.32 (m, 2H), 1.16 (m, 2H), 0.99 (m, 2H). HPLC-3: Rt 7.40 min, purity=98%.

Example 14

2-(4-Chlorophenyl)-5-(4-(2-cyclopropyl-2-hydroxyethoxy)-3-methoxyphenyl)-5,6-dihydropyrrolo[3,4-d][1,2,3]triazol-4(2H)-one

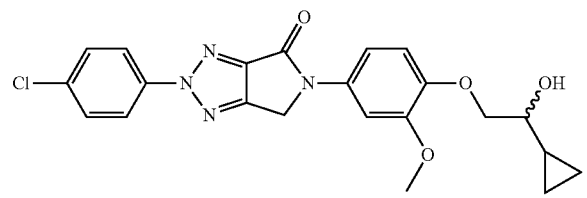

To a stirred suspension of Example 14B (11.7 mg, 0.027 mmol) in MeOH (2.0 mL) and THF (0.75 mL) at RT was added sodium borohydride (1.1 mg, 0.029 mmol) and the mixture was stirred at RT for 12 h. After cooling to 0° C., phosphate buffer (8 mL, 0.5M $KH_2PO_4$ +$H_3PO_4$ to pH 3) was added and the aqueous mixture was stirred at RT for 5 h. The mixture was extracted with $CH_2Cl_2$ (3×30 mL) and the combined organic extracts were dried ($Na_2SO_4$) and concentrated. Chromatography ($SiO_2$ 230-400 mesh, 95/5 $CHCl_3$/MeOH) of the crude product furnished Example 14 (10.2 mg, 0.023 mmol, 86% yield) as a yellow solid: LC-MS, $[M+H]^+$=441. $^1H$ NMR ($CD_2Cl_2$, 500 MHz): δ 8.08 (d, J=8.8 Hz, 2H), 7.53 (d, J=2.2 Hz, 1H) 7.49 (d, J=8.8 Hz, 2H), 7.03 (dd, J=8.8, 2.2 Hz, 1H), 6.96 (d, J=8.8 Hz, 1H), 4.92 (s, 2H), 4.13 (dd, J=9.9, 2.8 Hz, 1H), 3.94 (dd, J=9.9, 8.3 Hz, 1H), 3.87 (s, 3H), 3.27 (dt, J=8.3, 2.8 Hz, 1H), 0.92 (m, 1H), 0.52 (m, 2H), 0.37 (m, 1H) 0.28 (m, 1H). HPLC-3: Rt 7.55 min, purity=99%.

Example 15

2-(4-Chlorophenyl)-5-(3-methoxy-4-(2-(pyrrolidin-1-yl)ethoxy)phenyl)-4,5-dihydropyrrolo[3,4-e]pyrazol-6(2H)-one, TFA

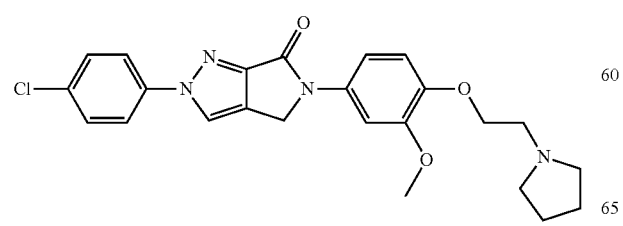

Example 15A 2-((2-Methoxy-4-nitrophenoxy)methoxy)ethyl)trimethylsilane

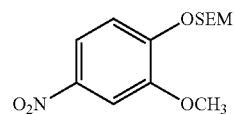

To a mixture of 2-methoxy-4-nitrophenol (2 g, 11.82 mmol) in $CH_2Cl_2$ (5 mL) at 0° C. was added SEM-Cl (2.73 mL, 15.37 mmol) and diisopropylethylamine (3.10 mL, 17.74 mmol). The resulting mixture was stirred at this temperature for 10 min then allowed to warm to room temperature. After stirring at room temperature for 3.5 h, the solvent was evaporated. The crude residue was diluted with EtOAc (200 mL) and washed with $H_2O$ (30 mL). The organic layer was separated, dried over $MgSO_4$ and concentrated to give the crude product which was further purified by ISCO automated chromatography (110 g, Hexane/EtOAc, 100:0 to 50:50 gradient) to give Example 15A (2.9 g, 82% yield) as a light yellow oil.

Example 1513

3-Methoxy-4((2-(trimethylsilyl)ethoxy)methoxy)aniline

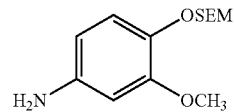

A mixture of (2-((2-methoxy-4-nitrophenoxy)methoxy)ethyl)trimethylsilane (2.9 g, 9.69 mmol), 10% palladium on active carbon (290 mg, 0.273 mmol) in EtOH (30 mL) was set for hydrogenation (1 atm) for 4 h. The catalyst was removed via filtration through a CELITE® pad. The filtrate was collected and concentrated to give Example 15B (2.45 g, 94% yield) as a light brown, viscous oil, which was used for next step without further purification. LCMS (ES): m/z 270.5 $[M+H]^+$.

Example 15C

Ethyl 1-(4-chlorophenyl)-3-(3-methoxy-4-((2-(trimethylsilyl)ethoxy)methoxy)phenylcarbamoyl)-1H-pyrazole-4-carboxylate

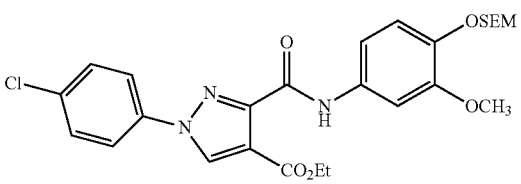

To a mixture of 1-(4-chlorophenyl)-4-(ethoxycarbonyl)-1H-pyrazole-3-carboxylic acid (1.5 g, 5.09 mmol) in $CH_2Cl_2$ (60 mL) was added BOP reagent (3.38 g, 7.64 mmol) and diisopropylethylamine (2.67 mL, 15.27 mmol). The resulting mixture was stirred at room temperature over night. The solvent was evaporated and the crude product was purified by ISCO automated chromatography (110 g, Hexane/EtOAc, 100:0 to 0:100 gradient) to give a product as light pink solid. This product was diluted with $CH_2Cl_2$ (200 mL), extracted with $H_2O$ (100 mL), dried over $MgSO_4$ and concentrated to give Example 15C (3.17 g, partially pure) as a light pink solid. LCMS (ES): m/z 546.5 $[M+H]^+$.

Example 15D 1-(4-Chlorophenyl)-4-(hydroxymethyl)-N-(3-methoxy-4-((2-(trimethylsilyl)ethoxy)methoxy)phenyl)-1H-pyrazole-3-carboxamide

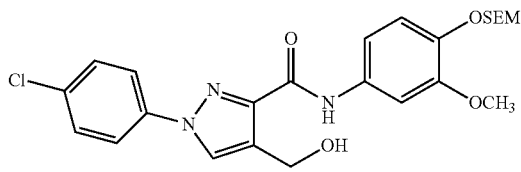

To a solution of ethyl 1-(4-chlorophenyl)-3-(3-methoxy-4-((2-(trimethylsilyl)ethoxy)methoxy)phenylcarbamoyl)-1H-pyrazole-4-carboxylate (3.17 g, 5.80 mmol) in THF (100 mL) at room temperature was added a solution of $LiBH_4$ (8.13 mL, 16.25 mmol, 2M in THF) dropwise. The resulting mixture was allowed to stir at room temperature for 2.5 h. The mixture was carefully quenched with aqueous sate. $NaHCO_3$ (2.5 mL). Solid residue was removed via filtration. The filtrate was concentrated to give the crude product which was further purified by ISCO automated chromatography (40 g size, Hexane/EtOAc, 100:0 to 0:100 gradient) to give Example 15D (2.11 g, 72% yield) as a yellow foam solid Example 15E (4-(Chloromethyl)-1-(4-chlorophenyl)-N-(4-hydroxy-3-methoxyphenyl)-1H-pyrazole-3-carboxamide

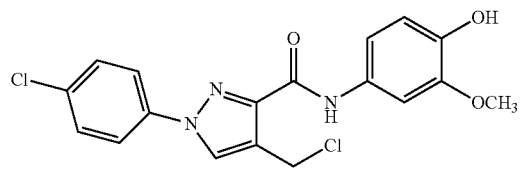 [SMILES: COc1cc(NC(=O)c2nn(-c3ccc(Cl)cc3)cc2CCl)ccc1O]

To a mixture of 1-(4-chlorophenyl)-4-(hydroxymethyl)-N-(3-methoxy-4-((2-(trimethylsilyl)ethoxy)methoxy)phenyl)-1H-pyrazole-3-carboxamide (2.11 g, 4.19 mmol) in $CH_2Cl_2$ (40 mL) at room temperature under Ar was added methanesulfonyl chloride (0.424 mL, 5.44 mmol) and triethylamine. (1.20 mL, 8.61 mmol). The resulting solution was stirred at room temperature for 1.5 h. Solvent was evaporated. The crude product was diluted with EtOAc (150 mL), washed with $H_2O$ (30 mL). The organic layer was separated, dried over $MgSO_4$ and concentrated to give a crude product which was further purified by ISCO automated chromatography (110 g, Hexane/EtOAc, 100:0 to 50:50 gradient) to give the products as beige solid (0.721 g, 44% yield). SEM group was deprotected during the process. LCMS (ES): m/z 392.0 $[M+H]^+$.

Example 15F 2-(4-Chlorophenyl)-5-(4-hydroxy-3-methoxyphenyl)-4,5-dihydropyrrolo[3,4-c]pyrazol-6(2H)-one

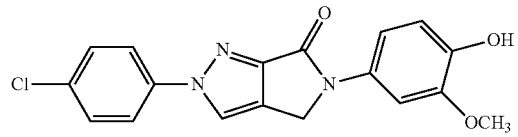 [SMILES: COc1cc(N2Cc3cn(-c4ccc(Cl)cc4)nc3C2=O)ccc1O]

A mixture of 4-(chloromethyl)-1-(4-chlorophenyl)-N-(4-hydroxy-3-methoxyphenyl)-1H-pyrazole-3-carboxamide (29.9 mg, 0.076 mmol) and potassium carbonate (42 mg, 0.304 mmol) in DMF (0.5 mL) was stirred at room temperature overnight. The mixture was diluted with $H_2O$ (4.5 mL). The pH of the resulting mixture was adjusted to 8 by adding 1N aq. HCl. The solid was collected via filtration to give a product as pink color solid (15 mg, 56% yield). The product was used for next step without further purification. LCMS (ES): m/z 356.4 $[M+H]^+$.

Example 15

2-(4-Chlorophenyl)-5-(3-methoxy-4-(2-(pyrrolidin-1-yl)ethoxy)phenyl)-4,5-dihydropyrrolo[3,4-c]pyrazol-6(2H)-one, TFA

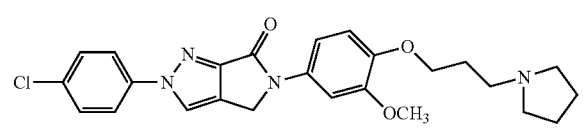 [SMILES: COc1cc(N2Cc3cn(-c4ccc(Cl)cc4)nc3C2=O)ccc1OCCCN1CCCC1]

A stirring mixture of 2-(4-chlorophenyl)-5-(4-hydroxy-3-methoxyphenyl)-4,5-dihydropyrrolo[3,4-c]pyrazol-6(2H)-one (15 mg, 0.042 mmol), 1-(2-chloroethyl)pyrrolidine, HCl (17.93 mg, 0.105 mmol) and cesium carbonate (54.9 mg, 0.169 mmol) in acetonitrile (3 mL) was heated at 80° C. for 5 h. Supernatant was taken out. The solid residue was diluted with $H_2O$ (1.5 mL), extracted with EtOAc (3×8 mL). The organic layer was combined with supernatant then concentrated to give the crude product which was purified by preparative HPLC. Desired fraction was collected and concentrated under SPEEDVAC® to give Example 15 (2.5 mg, 11% yield) as a white solid. LCMS (ES): m/z 453.5 $[M+H]^+$. $^1H$ NMR ($CDCl_3$) δ 2.05-2.22 (m, 4H), 3.01-3.15 (m, 2H), 3.52-3.60 (m, 2H), 3.90 (s, 3H), 3.90-4.00 (m, 2H), 4.35-4.43 (m, 2H), 4.80 (s, 2H), 6.90 (dd, J=8.8, 2.7 Hz, 1H), 6.94 (d, J=8.8 Hz, 1H), 7.43-7.50 (m, 2H), 7.72-7.76 (m, 2H), 7.84 (d, J=2.7 Hz, 1H), 7.89 (s, 1H).

Example 16

2-(4-Chlorophenyl)-5-(6-(3-(methylamino)pyrrolidin-1-yl)pyridin-3-yl)-4,5-dihydropyrrolo[3,4-c]pyrazol-6(2H)-one, 2 TFA

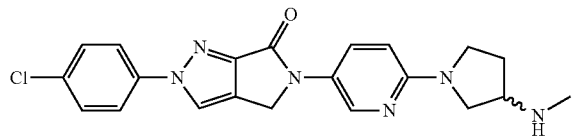 [SMILES: CNC1CCN(c2ccc(N3Cc4cn(-c5ccc(Cl)cc5)nc4C3=O)cn2)C1]

Example 16A

N-Methyl-1-(5-nitropyridin-2-yl)pyrrolidin-3-amine

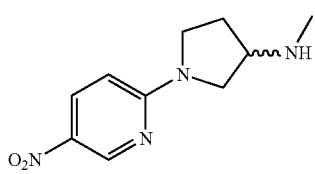 [SMILES: CNC1CCN(c2ccc([N+](=O)[O-])cn2)C1]

N-methylpyrrolidin-3-amine (0.395 g, 3.94 mmol) was added to 2-bromo-5-nitropyridine (0.8 g, 3.94 mmol) slowly (CAUTION: extreme exotherm!!!). The resulting mixture was heated at 110° C. for 2 h. After cooling down to room temperature, the obtained black solid product (Example 16A, 0.87 g, 99%) was used for next step without further purification. LCMS (ES): m/z 233.4 [M+H]$^+$.

Example 16B tert-Butyl methyl(1-(5-nitropyridin-2-yl)pyrrolidin-3-yl)carbamate

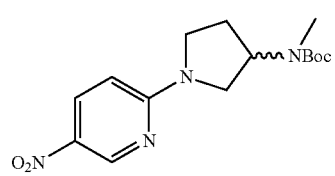

To a mixture of N-methyl-1-(5-nitropyridin-2-yl)pyrrolidin-3-amine (0.87 g, 3.91 mmol) in THF (50 mL) and H$_2$O (20 mL) was added NaHCO$_3$ (0.987 g, 11.74 mmol) and di-t-butyl dicarbonate (1.182 mL, 5.09 mmol). The resulting mixture was stirred at room temperature for 3 h. Solvent was evaporated. The residue was diluted with H$_2$O (20 mL), extracted with EtOAc (80 mL). The organic layer was separated, dried over MgSO$_4$ and concentrated to give the crude product which was further purified by ISCO automated chromatography (40 g, Hexane/EtOAc, 100:0 to 50:50 gradient) to give Example 16B (0.95 g, 75%) as a bright yellow solid. LCMS (ES): m/z 323.4 [M+H]$^+$.

Example 16C tert-Butyl 1-(5-aminopyridin-2-yl)pyrrolidin-3-yl(methyl)carbamate

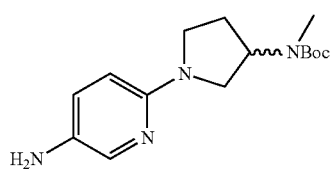 [SMILES: CN(C(=O)OC(C)(C)C)C1CCN(c2ccc([N+](=O)[O-])cn2)C1]

A mixture of tert-butyl methyl(1-(5-nitropyridin-2-yl)pyrrolidin-3-yl)carbamate (0.91 g, 2.82 mmol), 10% palladium on active carbon (91 mg, 0.086 mmol) in EtOH (30 mL) was hydrogenated (1 atm) for 10 min. MeOH (15 mL) was added. The resulting mixture was hydrogenated (1 atm) for 4 h. The catalyst was removed via filtration through CELITE® pad. The filtrate was collected and concentrated to give Example 16C (0.79 g, 96%) as a dark brown foam solid which was used for next step without further purification. LCMS (ES): m/z 293.5 [M+H]$^+$.

Example 16D

Ethyl 3-(6-(3-(tert-butoxycarbonyl(methyl)amino)pyrrolidin-1-yl)pyridin-3-ylcarbamoyl)-1-(4-chlorophenyl)-1H-pyrazole-4-carboxylate

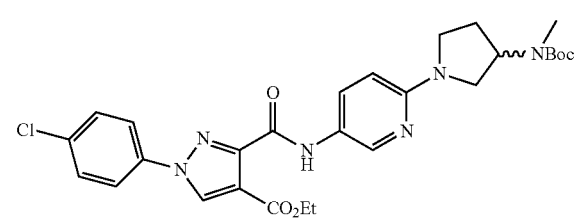 [SMILES: CCOC(=O)c1cn(-c2ccc(Cl)cc2)nc1C(=O)Nc1ccc(N2CCC(N(C)C(=O)OC(C)(C)C)C2)nc1]

To a mixture of 1-(4-chlorophenyl)-4-(ethoxycarbonyl)-1H-pyrazole-3-carboxylic acid (120 mg, 0.407 mmol) in CH$_2$Cl$_2$ (15 mL) was added HOBt (74.8 mg, 0.489 mmol) and EDC (94 mg, 0.489 mmol). The resulting mixture was stirred at room temperature over a weekend. Solvent was evaporated. The crude was diluted with H$_2$O (10 mL), extracted with EtOAc (30 mL). The organic layer was separated, dried over MgSO$_4$ and concentrated to give a product which was further purified by ISCO automated chromatography (12 g, Hexane/EtOAc, 100:0 to 0:100 gradient) to give Example 16D (218 mg, 94%) as a light brown foam solid. LCMS (ES): m/z 569.5 [M+H]$^+$.

Example 16E tert-Butyl 1-(5-(1-(4-chlorophenyl)-4-(hydroxymethyl)-1H-pyrazole-3-carboxamido)pyridin-2-yl)pyrrolidin-3-yl(methyl)carbamate

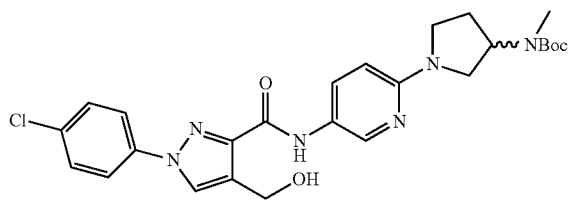 [SMILES: CN(C(=O)OC(C)(C)C)C1CCN(c2ccc(NC(=O)c3nn(-c4ccc(Cl)cc4)cc3CCl)cn2)C1]

To a solution of ethyl 3-(6-(3-(tert-butoxycarbonyl(methyl)amino)pyrrolidin-1-yl)pyridin-3-ylcarbamoyl)-1-(4-chlorophenyl)-1H-pyrazole-4-carboxylate (218 mg, 0.383 mmol) in THF (8 mL) was added LiBH$_4$ solution (0.536 mL, 1.073 mmol, 2M in THF). The resulting mixture was stirred at room temperature for 3 h. The mixture was quenched with sat. NaHCO$_3$ solution (0.5 mL). Solid residue was removed via filtration. The filtrate was concentrated to give the crude product which was further purified by silica gel chromatography (Hexane/EtOAc, 100:0 to 0:100 gradient) to give Example 16E (130 mg, 64%) as a yellow solid. LCMS (ES): m/z 527.1 [M+H]$^+$.

Example 16F tert-Butyl 1-(5-(4-(chloromethyl)-1-(4-chlorophenyl)-1H-pyrazole-3-carboxamido)pyridin-2-yl)pyrrolidin-3-yl(methyl)carbamate

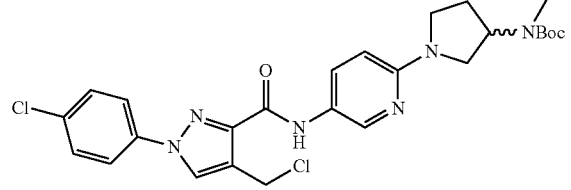

To a mixture of tert-butyl 1-(5-(1-(4-chlorophenyl)-4-(hydroxymethyl)-1H-pyrazole-3-carboxamido)pyridin-2-yl)pyrrolidin-3-yl(methyl)carbamate (130 mg, 0.247 mmol) in CH$_2$Cl$_2$ (2.5 mL) at room temperature under Ar was added methanesulfonyl chloride (0.031 mL, 0.395 mmol) and diisopropylethylamine (0.086 mL, 0.493 mmol). The resulting solution was stirred at room temperature overnight. Solvent was evaporated. The residue was diluted with H$_2$O (3 mL), extracted with EtOAc (15 mL). The organic layer was separated, dried over MgSO$_4$ and concentrated to give a crude product which was further purified by ISCO automated chromatography (12 g, Hexane/EtOAc, 100:0 to 30:70 gradient) to give Example 16F (126 mg, 94%) as a light brown foam solid. LCMS (ES): m/z 545.5 [M+H]$^+$.

Example 16G tert-Butyl 1-(5-(2-(4-chlorophenyl)-6-oxopyrrolo[3,4-e]pyrazol-5(2H,4H,6H)-yl)pyridin-2-yl)pyrrolidin-3-yl(methyl)carbamate

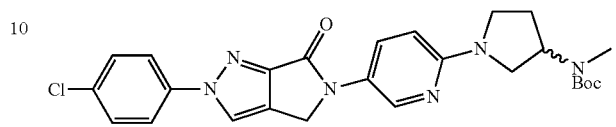

A mixture of tert-butyl 1-(5-(4-(chloromethyl)-1-(4-chlorophenyl)-1H-pyrazole-3-carboxamido)pyridin-2-yl)pyrrolidin-3-yl(methyl)carbamate (126 mg, 0.231 mmol) and potassium carbonate (89 mg, 0.647 mmol) in DMF (3 mL) was stirred at RT for 40 h. The resulting mixture was diluted with H$_2$O (10 mL), stirred for 5 min and subjected to filtration. The solid was further washed with H$_2$O (30 mL), dried under vacuum to give Example 16G (71 mg, 57% yield) as a beige solid. LCMS (ES): m/z 509.5 [M+H]$^+$. $^1$H NMR (CDCl$_3$) δ 1.51 (s, 9H), 2.10-2.28 (m, 2H), 2.84 (s, 3H), 3.35-3.50 (m, 2H), 3.65-3.72 (m, 2H), 4.78 (s, 2H), 4.85-5.05 (bs, 1H), 6.45 (d, J=8.8 Hz, 1H), 7.45-7.50 (m, 2H), 7.73-7.79 (m, 2H), 7.90 (s, 1H), 8.09 (dd, J=8.8, 2.7 Hz, 1H), 8.29 (d, J=2.7 Hz, 1H).

Example 16

2-(4-Chlorophenyl)-5-(6-(3-(methylamino)pyrrolidin-1-yl)pyridin-3-yl)-4,5-dihydropyrrolo[3,4-e]pyrazol-6(2H)-one, 2 TFA

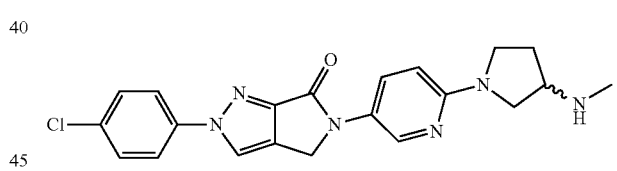

To a solution of tert-butyl 1-(5-(2-(4-chlorophenyl)-6-oxopyrrolo[3,4-e]pyrazol-5(2H,4H,6H)-yl)pyridin-2-yl)pyrrolidin-3-yl(methyl)carbamate (51.4 mg, 0.101 mmol) in CH$_2$Cl$_2$ (3.5 mL) at room temperature was added TFA (1.50 mL). The resulting mixture was stirred at room temperature for 1.5 h. The solvent was evaporated to give a solid product. The product was washed with cold CH$_2$Cl$_2$ (10 mL) to afford Example 16 (64 mg, 98%) as a beige solid. LCMS (ES): m/z 409.5 [M+H]$^+$. $^1$H NMR (DMSO-d$_6$) δ 2.12-2.23 (m, 1H), 2.30-2.42 (m, 1H), 2.65 (t, J=5.5 Hz, 3H), 3.42-3.50 (m, 1H), 3.55-3.56 (m, 1H), 3.71-3.78 (m, 2H), 3.85-3.94 (m, 1H), 4.90 (s, 2H), 6.70 (d, J=9.4 Hz, 1H), 7.60-7.66 (m, 2H), 7.93-7.98 (m, 2H), 8.03 (dd, J=9.4, 2.8 Hz, 1H), 8.46 (d, J=2.8 Hz, 1H), 8.68 (s, 1H), 8.75 (m, 2H).

Example 16 was also prepared using a sequence analogous to the one shown for Example 11 above, except that Example 11A was replaced by 1-(5-bromopyridin-2-yl)-N-methylpyrrolidin-3-amine.

Example 17

(S)-2-(4-Chlorophenyl)-5-(6-(3-(dimethylamino)pyrrolidin-1-yl)pyridin-3-yl)-4,5-dihydropyrrolo[3,4-c]$_{pyrazol}$-6(2H)-one, 2 HCl

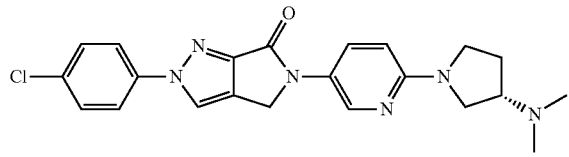 [SMILES: CN(C)[C@H]1CCN(c2ccc(N3Cc4cn(-c5ccc(Cl)cc5)nc4C3=O)cn2)C1]

Example 17A

Ethyl 1-(4-chlorophenyl)-4-(hydroxymethyl)-1H-pyrazole-3-carboxylate

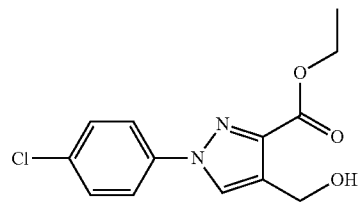 [SMILES: CCOC(=O)c1nn(-c2ccc(Cl)cc2)cc1CO]

To a solution of ethyl 1-(4-chlorophenyl)-4-formyl-1H-pyrazole-3-carboxylate (Example 11C, 1.63 g, 5.85 mmol) in THF (60 mL) at 0° C. was added sodium borohydride (0.111 g, 2.92 mmol). The resulting solution was stirred at this temperature for 2 h then quenched with sat. NaHCO$_3$ solution (4 mL) at 0° C. Supernatant was taken out. The solvent was evaporated to give a solid residue which was diluted with EtOAc (150 mL), and washed with H$_2$O (30 mL). The organic layer was separated, dried over MgSO$_4$, and concentrated to give a product. This product was further purified via recrystallization from EtOAc to give Example 17A (1.27 g, 77%) as a white solid. $^1$H NMR (CDCl$_3$) δ 1.48 (t, J=7.1 Hz, 3H), 3.59 (t, J=7.1 Hz, 1H), 4.52 (q, J=7.1 Hz, 2H), 4.79 (d, J=6.6 Hz, 2H), 7.45-7.50 (m, 2H), 7.66-7.71 (m, 2H), 7.89 (s, 1H).

Example 17B

Ethyl 1-(4-chlorophenyl)-4-(hydroxymethyl)-1H-pyrazole-3-carboxylic acid

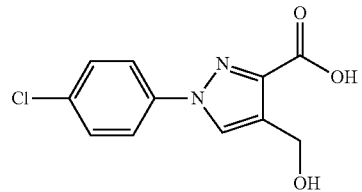 [SMILES: O=C(O)c1nn(-c2ccc(Cl)cc2)cc1CO]

A mixture of ethyl 1-(4-chlorophenyl)-4-(hydroxymethyl)-1H-pyrazole-3-carboxylate (1.27 g, 4.52 mmol), sodium hydroxide (0.59 g, 14.75 mmol) and water (70 mL) was heated at reflux for 2 h. After cooling down to RT, supernatant was separated. The supernatant was acidified with conc HCl. The mixture was cooled in a refrigerator for 2 h and then subjected to filtration to give the product, which was further dried under vacuum to give Example 17B (1.04 g, 91%) as a white solid. $^1$H NMR (DMSO-d$_6$) δ 4.64 (s, 2H), 5.15 (bs, 1H), 7.35-7.60 (m, 2H), 7.88-7.92 (m, 2H), 8.46 (s, 1H);

Example 17C

N-(6-Bromopyridin-3-yl)-1-(4-chlorophenyl)-4-(hydroxymethyl)-1H-pyrazole-3-carboxamide

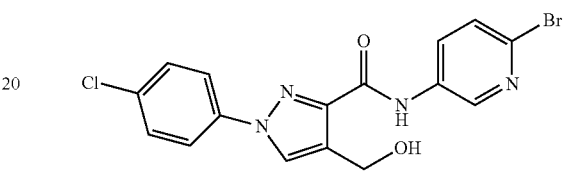

To a mixture of 1-(4-chlorophenyl)-4-(hydroxymethyl)-1H-pyrazole-3-carboxylic acid (350 mg, 1.39 mmol) and 6-bromopyridin-3-amine (288 mg, 1.66 mmol) in CH$_2$Cl$_2$ (35 mL) at room temperature was added HOBT (255 mg, 1.66 mmol) and EDC (319 mg, 1.66 mmol). The resulting mixture was stirred at room temperature overnight. The solvent was evaporated. The solid residue was diluted with water (30 mL), stirred for 10 min and then subjected to filtration. The solid was further washed with cold MeOH (20 mL) and dissolved in CH$_2$Cl$_2$ (60 mL). The organic layer was washed with H$_2$O (20 mL) and concentrated to give a solid product. The solid was further dried under vacuum to give Example 17C (330 mg, 58%) as a beige solid. $^1$H NMR (CDCl$_3$) δ 4.77 (s, 2H), 7.45-7.57 (m, 2H), 7.60-7.70 (m, 2H), 7.89 (s, 1H), 8.20-8.26 (s, 2H), 8.56 (s, 1H), 8.89 (s, 1H). LCMS, [M+H]$^+$=409.2.

Example 17D

N-(6-Bromopyridin-3-yl)-4-(chloromethyl)-1-(4-chlorophenyl)-1H-pyrazole-3-carboxamide

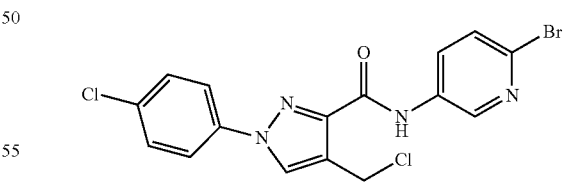

To mixture of N-(6-bromopyridin-3-yl)-1-(4-chlorophenyl)-4-(hydroxymethyl)-1H-pyrazole-3-carboxamide (330 mg, 0.810 mmol) in CH$_2$Cl$_2$ (15 mL) at RT was added methanesulfonyl chloride (0.101 mL, 1.295 mmol) and DIEA (0.283 mL, 1.619 mmol). The resulting mixture was stirred at room temperature over a weekend. The reaction mixture was diluted with H$_2$O, stirred for 5 min and subjected to filtration. The solid collected was dried under vacuum to give Example 17D (340 mg, (99%) as a beige solid. $^1$H NMR (CDCl$_3$) δ

4.98 (s, 2H), 7.44-7.53 (m, 2H), 7.61-7.72 (m. 2H), 8.06 (s, 1H), 8.20-8.28 (s, 2H), 8.53 (s, 1H), 8.79 (s, 1H). LCMS, [M+H]⁺=426.9.

Example 17E 5-(6-Bromopyridin-3-yl)-2-(4-chlorophenyl)-4,5-dihydropyrrolo[3,4-e]pyrazol-6(2H)-one

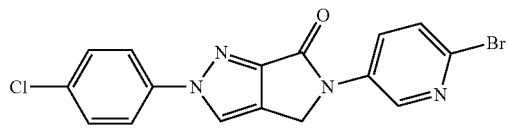 [SMILES: O=C1c2nn(-c3ccc(Cl)cc3)cc2CN1c1ccc(Br)nc1]

A mixture of N-(6-bromopyridin-3-yl)-4-(chloromethyl)-1-(4-chlorophenyl)-1H-pyrazole-3-carboxamide (340 mg, 0.798 mmol) and potassium carbonate (309 mg, 2.23 mmol) in DMF (5 mL) was stirred at room temperature for 40 h. The resulting mixture was diluted with H₂O (10 mL), stirred for 5 min and subjected to filtration. The solid was further washed with H₂O (30 mL), dried under vacuum to give Example 17E (220 mg, 71% yield) as a beige solid. ¹H NMR (DMSO-d₆) δ 5.01 (s, 2H), 7.62-7.65 (m, 2H), 7.73 (d, J=8.7 Hz, 1H), 7.94-8.00 (m. 2H), 8.31 (dd, J=8.7, 2.7 Hz, 1H), 8.73 (s, 1H), 8.86 (d, J=2.7 Hz, 1H). LCMS, [M+H]⁺=391.3.

Example 17

(S)-2-(4-Chlorophenyl)-5-(6-(3-(methylamino)pyrrolidin-1-yl)pyridin-3-yl)-4,5-dihydropyrrolo[3,4-e]pyrazol-6(2H)-one, 2 HCl

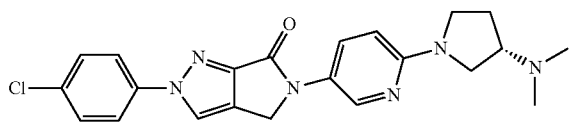 [SMILES: CN(C)[C@H]1CCN(c2ccc(N3Cc4cn(-c5ccc(Cl)cc5)nc4C3=O)cn2)C1]

To a mixture of 5-(6-bromopyridin-3-yl)-2-(4-chlorophenyl)-4,5-dihydropyrrolo[3,4-c]pyrazol-6(2H)-one (50 mg, 0.128 mmol) in DMSO (1.5 mL) was added (S)-N,N-dimethylpyrrolidin-3-amine (480 mg, 4.20 mmol). The resulting mixture was irradiated in microwave reactor at 120° C. for 30 min. The sealed tube was heated at 120° C. for 2 h and allowed to cool down to room temperature. The reaction mixture was subjected to filtration. The solid collected was further washed with MeOH (5 mL) and dried under vacuum to give the free base product (33.5 mg) as light yellow solid. The solid product was stirred with 4M HCl in dioxane (1 mL) for 15 min. MeOH (1 mL) was added. The mixture was stirred for 15 min, sonicated for 2 min. The solvent was evaporated to give the product as light yellow powder. The product was dissolved in ml H₂O (8 mL) and subjected to lyophilization to give Example 17 (39.4 mg, 100%) as a yellow powder. ¹H NMR (D₂O) δ 2.20-2.35 (m, 1H), 2.60-2.70 (m, 1H), 2.86 (s, 6H), 3.40-3.70 (m, 3H), 3.86-3.95 (m, 1H), 4.02-4.14 (m, 1H), 4.30-4.40 (m, 2H), 6.60-6.68 (m, 1H), 7.13-7.20 (m, 2H), 7.26-7.35 (m, 2H), 7.78-7.85 (m, 1H), 7.92-7.99 (m, 2H). LCMS, [M+H]⁺=423.3.

Example 18

(R)-2-(4-Chlorophenyl)-5-(6-(3-(methylamino)pyrrolidin-1-yl)pyridin-3-yl)-4,5-dihydropyrrolo[3,4-c]pyrazol-6(2H)-one, 2 HCl

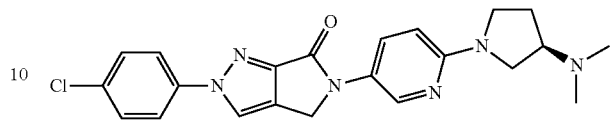

To a mixture of 5-(6-bromopyridin-3-yl)-2-(4-chlorophenyl)-4,5-dihydropyrrolo[3,4-c]pyrazol-6(2H)-one (50 mg, 0.128 mmol) in DMSO (1.5 mL) was added (R)-N,N-dimethylpyrrolidin-3-amine (430 mg, 3.77 mmol). The resulting mixture was irradiated in microwave reactor at 120° C. for 30 min. The sealed tube was heated at 120° C. for 2 h and allowed to cool down to room temperature. The reaction mixture was subjected to filtration. The solid collected was further washed with MeOH (5 mL). The product was dried under vacuum to give the free base product (33.0 mg) as light yellow solid. The solid product was stirred with 4M HCl in dioxane (1 mL) for 15 min. MeOH (1 mL) was added and the mixture was stirred for 15 min, and sonicated for 2 min. The solvent was evaporated to give the product as a light yellow powder. The product was dissolved in H₂O (8 mL) and subjected to lyophilization to give Example 18 (41 mg, 106%) as a yellow powder. ¹H NMR (D₂O) δ 2.20-2.35 (m, 1H), 2.58-2.71 (m, 1H), 2.84 (s, 6H), 3.40-3.75 (m, 3H), 3.87-3.96 (m, 1H), 4.05-4.15 (m, 1H), 4.25-4.43 (m, 2H), 6.60-6.68 (m, 1H), 7.10-7.22 (m, 2H), 7.25-7.31 (m, 2H), 7.75-7.86 (m, 1H), 7.90-7.99 (m, 2H). LCMS, [M+H]⁺=423.3.

Example 19

(R)-2-(4-Chlorophenyl)-5-(6-(3-(methylamino)pyrrolidin-1-yl)pyridin-3-yl)-4,5-dihydropyrrolo[3,4-c]pyrazol-6(2H)-one, 2 HCl

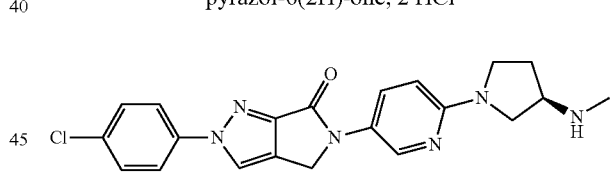

Example 19A (R)-tort-Butyl 1-(5-(2-(4-chlorophenyl)-6-oxopyrrolo[3,4-c]pyrazol-5(2H,4H,6H)-yl)pyridin-2-yl)pyrrolidin-3-yl(methyl)carbamate

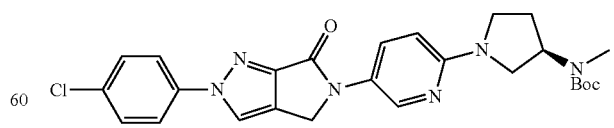

Following a procedure similar to one described in Example 16, Example 19A was obtained by using commercially available (R)-N-methylpyrrolidin-3-amine as starting material. LCMS (ES): [M+H]⁺=509.5. ¹H NMR (CDCl₃) δ 1.49 (s, 9H), 2.10-2.28 (m, 2H), 2.83 (s, 3H), 3.35-3.50 (m, 2H), 3.65-3.72 (m, 2H), 4.77 (s, 2H), 4.85-5.05 (bs, 1H), 6.44 (d, J=8.8 Hz, 1H), 7.44-7.50 (m, 2H), 7.72-7.77 (m, 2H), 7.89 (s, 1H), 8.08 (dd, J=8.8, 2.2 Hz, 1H), 8.28 (d, J=2.2 Hz, 1H).

Example 19

(R)-2-(4-Chlorophenyl)-5-(6-(3-(methylamino)pyrrolidin-1-yl)pyridin-3-yl)-4,5-dihydropyrrolo[3,4-c]pyrazol-6(2H)-one, 2 HCl

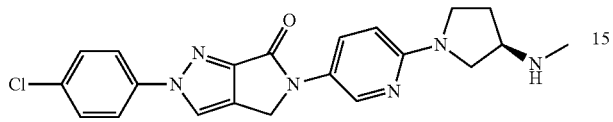

A mixture of (R)-tort-butyl 1-(5-(2-(4-chlorophenyl)-6-oxopyrrolo[3,4-c]pyrazol-5(2H,4H,6H)-yl)pyridin-2-yl)pyrrolidin-3-yl(methyl)carbamate (186 mg, 0.365 mmol) and 4M HCl in dioxane (10 mL, 40.0 mmol) was stirred at RT for 2 h. MeOH (0.6 mL) was added and the resulting mixture was sonicated for 3 min and stirred at RT for 0.5 h. The solvent was evaporated to give a product as a white powder which was dissolved in H$_2$O (15 mL) and subjected to lyophilization to give Example 19 (188 mg, 101%) as a light yellow powder. $^1$H NMR (D$_2$O) δ 2.35-2.48 (m, 1H), 2.65-2.76 (m, 1H), 2.86 (s, 3H), 3.63-3.83 (m, 3H), 3.95-4.05 (m, 1H), 4.11-4.20 (m, 1H), 4.65 (s, 2H), 6.85-6.92 (m, 1H), 7.37-7.44 (m, 2H), 7.52-7.60 (m, 2H), 8.02-8.24 (m, 3H). LCMS (ES): [M+H]$^+$ 409.2.

Example 20

(S)-2-(4-Chlorophenyl)-5-(6-(3-(methylamino)pyrrolidin-1-yl)pyridin-3-yl)-4,5-dihydropyrrolo[3,4-c]pyrazol-6(2H)-one, 2 HCl

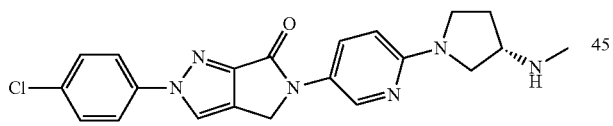

Example 20A (S)-tert-Butyl 1-(5-(2-(4-chlorophenyl)-6-oxopyrrolo[3,4-c]pyrazol-5(2H,4H,6H)-yl)pyridin-2-yl)pyrrolidin-3-yl(methyl)carbamate

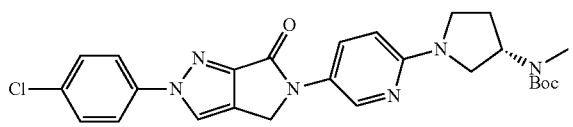 [SMILES: CN(C(=O)OC(C)(C)C)[C@H]1CCN(c2ccc(N3Cc4cn(-c5ccc(Cl)cc5)nc4C3=O)cn2)C1]

Following a procedure similar to one described in Example 16, Example 20A was obtained by using commercially available (S)-N-methylpyrrolidin-3-amine as starting material. LCMS (ES): [M+H]$^+$=509.5. $^1$H NMR (CDCl$_3$) δ 1.49 (s, 9H), 2.10-2.28 (m, 2H), 2.83 (s, 3H), 3.35-3.50 (m, 2H), 3.63-3.72 (m, 2H), 4.78 (s, 2H), 4.85-5.05 (bs, 1H), 6.43 (d, J=8.8 Hz, 1H), 7.45-7.50 (m, 2H), 7.73-7.75 (m, 2H), 7.89 (s, 1H), 8.07 (dd, J=8.8, 2.7 Hz, 1H), 8.28 (d, J=2.7 Hz, 1H).

Example 20

(S)-2-(4-Chlorophenyl)-5-(6-(3-(methylamino)pyrrolidin-1-yl)pyridin-3-yl)-4,5-dihydropyrrolo[3,4-c]pyrazol-6(2H)-one, 2 HCl

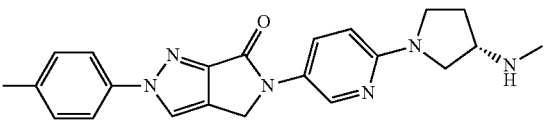

A mixture of (S)-tert-butyl 1-(5-(2-(4-chlorophenyl)-6-oxopyrrolo[3,4-c]pyrazol-5(2H,4H,6H)-yl)pyridin-2-yl)pyrrolidin-3-yl(methyl)carbamate (15 mg, 0.029 mmol) and 4M HCl in dioxane (0.9 mL) was stirred at RT for 2 h. MeOH (0.6 mL) was added. The resulting mixture was sonicated for 3 min and stirred at RT for 0.5 h. The solvent was evaporated to give the product as white powder. The product was dissolved in H$_2$O (3 mL) and subjected to lyophilization to give Example 20 (13.4 mg, 90%) as a light yellow powder. $^1$H NMR (D$_2$O) δ 2.20-2.30 (m, 1H), 2.45-2.58 (m, 1H), 2.70 (s, 3H), 3.40-3.60 (m, 3H), 3.72-3.80 (m, 1H), 3.90-4.0 (m, 1H), 4.40 (s, 2H), 6.52-6.60 (m, 1H), 7.15-7.24 (m, 2H), 7.28-7.35 (m, 2H), 7.75-8.00 (m, 3H). LCMS (ES): [M+H]$^+$=409.2.

Examples 21 to 32

Examples 21 to 32 shown in the table below were prepared using a procedure analogous to one used to prepare Example 11 above except that Example 11A was replaced by the corresponding bromo pyridine (synthesized similar to Example 11A). In several cases, the bromopyridine intermediates were prepared via displacement of Mesylate A shown below by the appropriate amine.

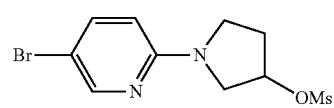

Mesylate A

TABLE

| Ex. No. | Name | R | LC-MS, [M + H]+ | 1H NMR (DMSO-d6, 400 MHz): δ | HPLC-1: Rt min, purity; HPLC-2: Rt min, purity |
|---|---|---|---|---|---|
| 21 | N-(1-(5-(2-(4-Chlorophenyl)-6-oxopyrrolo[3,4-c]pyrazol-5(2H,4H,6H)-yl)pyridin-2-yl)pyrrolidin-3-yl)-N-methylacetamide | X = CH | 451 | 8.68 (s, 1H), 8.44 (s, 1H), 8.10 (m, 1H), 7.97 (d, J = 8.8 Hz, 2H), 7.65 (d, J = 8.8 Hz, 2H), 6.80 (m, 1H), 4.92 (s, 2H), 3.49 (m, 3H), 3.11 (m, 1H), 2.90 (s, 3H), 2.75 (s, 1H), 2.1 (s, 3H), 2.03 (m, 2H) | 6.25, 92%; 7.22, 93% |
| 22 | N-(1-(5-(2-(4-Chlorophenyl)-6-oxopyrrolo[3,4-c]pyrazol-5(2H,4H,6H)-yl)pyridin-2-yl)pyrrolidin-3-yl)acetamide | X = CH | 437 | 8.68 (s, 1H), 8.41 (s, 1H), 8.32 (m, 1H), 8.19 (d, J = 6.4 Hz, 1H), 7.98 (m, 3H), 7.65 (d, J = 6.8 Hz, 2H), 6.78 (m, 1H), 4.89 (s, 2H), 4.36 (m, 1H), 3.63 (m, 4H), 2.20 (m, 2H), 1.82 (s, 3H) | 6.07, 94%; 6.96, 96% |
| 23 | N-(1-(5-(2-(4-Chlorophenyl)-6-oxopyrrolo[3,4-c]pyrazol-5(2H,4H,6H)-yl)pyridin-2-yl)pyrrolidin-3-yl)-N-ethylacetamide | X = CH | 465 | At 80° C.: 8.52 (s, 1H), 8.42 (d, J = 2.64 Hz, 1H), 7.94 (m, 3H), 7.61 (d, J = 8.04 Hz, 2H), 6.56 (d, J = 9.20 Hz, 1H), 4.86 (s, 2H), 4.72 (m, 1H), 3.72 (m, 2H), 3.43 (m, 4H), 2.22 (m, 2H), 2.08 (s, 3H), 1.15 (m, 3H) | 6.41, 95%; 7.50, 95% |
| 24 | 5-(6-(3-(tert-Butylamino)pyrrolidin-1-yl)pyridin-3-yl)-2-(4-chlorophenyl)-4,5-dihydropyrrolo[3,4-c]pyrazol-6(2H)-one | X = CH | 451 | 8.66 (s, 1H), 8.37 (d, J = 3.96 Hz, 1H), 7.86 (s, 1H), 7.96 (d, J = 8.76 Hz, 2H), 7.85 (m, 1H), 7.63 (d, J = 8.76 Hz, 2H), 6.48 (d, J = 9.12 Hz, 1H), 4.86 (s, 2H), 3.66 (m, 1H), 3.49 (m, 2H), 2.94 (s, 1H), 2.15 (m, 2H), 1.69 (m, 2H), 1.06 (s, 9H) | HPLC-1: 6.78, >99% |
| 25 | (R)-2-(4-Chlorophenyl)-5-(6-(3-fluoropyrrolidin-1-yl)pyridin-3-yl)-4,5-dihydropyrrolo[3,4-c]pyrazol-6(2H)-one | X = CH | 398 | 8.57 (s, 1H), 8.43 (s, 1H), 7.96 (m, 3H), 7.63 (d, J = 8.76 Hz, 2H), 6.57 (d, J = 9.60 Hz, 1H), 5.52 (m, 1H), 4.87 (s, 2H), 3.75 (m, 3H), 3.51 (m, 1H), 2.31 (m, 2H) | HPLC-1: 6.88, 99% |
| 26 | 2-(4-Chlorophenyl)-5-(6-(4-hydroxypiperidin-1-yl)pyridin-3-yl)-4,5-dihydropyrrolo[3,4-c]pyrazol-6(2H)-one | X = CH | 410 | 8.68 (s, 1H), 8.45 (d, J = 2.80 Hz, 1H), 7.98 (m, 3H), 7.65 (d, J = 9.20 Hz, 2H), 6.94 (d, J = 9.60 Hz, 1H), 4.90 (s, 2H), 4.70 (d, J = 4.00 Hz, 1H), 4.03 (m, 2H), 3.73 (m, 1H), 3.12 (m, 2H), 1.80 (m, 2H), 1.41 (m, 2H) | 6.16, 94%; 7.09, 97% |
| 27 | 5-(6-(4-Aminopiperidin-1-yl)pyridin-3-yl)-2-(4-chlorophenyl)-4,5-dihydropyrrolo[3,4-c]pyrazol-6(2H)-one | X = CH | 409 | 8.66 (s, 1H), 8.44 (d, J = 2.60 Hz, 1H), 7.97 (m, 3H), 7.64 (d, J = 8.80 Hz, 2H), 6.93 (d, J = 9.24 Hz, 1H), 4.89 (s, 2H), 4.20 (m, 2H), 2.92 (m, 5H), 1.77 (m, 2H), 1.25 (m, 2H) | HPLC-1: 11.46, 95% |

TABLE-continued

| Ex. No. | Name | R | LC-MS, [M + H]+ | 1H NMR (DMSO-d6, 400 MHz): δ | HPLC-1: Rt min, purity; HPLC-2: Rt min, purity |
|---|---|---|---|---|---|
| 28 | 5-(6-(1,3'-Bipyrrolidin-1'-yl)pyridin-3-yl)-2-(4-chlorophenyl)-4,5-dihydropyrrolo[3,4-c]pyrazol-6(2H)-one | X = CH | 449 | 8.52 (s, 1H), 8.39 (d, J = 2.60 Hz, 1H), 7.94 (d, J = 8.76 Hz, 2H), 7.89 (dd, J = 2.60, 8.88 Hz, 1H), 7.61 (d, J = 8.76 Hz, 2H), 6.52 (d, J = 8.88 Hz, 1H), 4.84 (s, 2H), 3.67 (m, 1H), 3.59 (m, 1H), 3.42 (m, 1H), 3.30 (m, 1H), 3.01 (m, 1H), 2.57 (m, 4H), 2.18 (m, 1H), 1.95 (m, 1H), 1.73 (s, 4H) | 5.41, 95%; 6.62, 96% |
| 29 | 2-(4-Chlorophenyl)-5-(6-(4-(pyrrolidin-1-yl)piperidin-1-yl)pyridin-3-yl)-4,5-dihydropyrrolo[3,4-c]pyrazol-6(2H)-one | X = CH HCl salt | 463 | 10.46 (s, 1H), 8.69 (s, 1H), 8.51 (s, 1H), 8.10 (d, J = 8.32 Hz, 1H), 7.97 (d, J = 8.92 Hz, 2H), 7.64 (d, J = 8.92 Hz, 2H), 7.15 (d, J = 8.32 Hz, 1H), 4.93 (s, 2H), 4.43 (m, 2H), 3.50 (m, 2H), 3.36 (m, 1H), 3.09 (m, 2H) 2.94 (m, 2H), 2.14 (m, 2H), 1.98 (m, 2H), 1.86 (m, 2H), 1.71 (m, 2H) | 5.95, 97%; 7.14, 97% |
| 30 | 2-(4-Chlorophenyl)-5-(6-(3-(1-hydroxy-2-methylpropan-2-ylamino)pyrrolidin-1-yl)pyridin-3-yl)-4,5-dihydropyrrolo[3,4-c]pyrazol-6(2H)-one | X = CH HCl salt | 467 | 8.98 (brs, 1H), 8.88 (brs, 1H), 8.71 (s, 1H), 8.49 (d, J = 2.36 Hz, 1H), 8.23 (m, 1H), 7.98 (d, J = 8.84 Hz, 2H), 7.65 (d, J = 8.84 Hz, 2H), 6.96 (m, 1H), 4.95 (s, 2H), 4.15 (m, 1H), 3.95 (m, 1H), 3.71 (m, 3H), 3.17 (m, 1H), 2.34 (m, 3H), 1.55 (m, 1H), 1.30 (m, 6H) | 5.43, 97%; 6.54, 97% |
| 31 | 2-(4-Chlorophenyl)-5-(6-(3-(tert-pentylamino)pyrrolidin-1-yl)pyridin-3-yl)-4,5-dihydropyrrolo[3,4-c]pyrazol-6(2H)-one | X = CH | 465 | 8.66 (s, 1H), 8.36 (s, 1H), 7.97 (d, J = 8.80 Hz, 2H), 7.91 (d, J = 8.32 Hz, 1H), 7.64 (d, J = 8.80 Hz, 2H), 6.48 (d, J = 8.32 Hz, 1H), 4.87 (s, 2H), 3.67 (m, 1H), 3.63 (m, 3H), 2.96 (m, 1H), 2.11 (m, 1H), 1.73 (m, 1H), 1.67 (m, 1H), 1.37 (m, 2H), 0.99 (m, 6H), 0.79 (m, 3H) | 5.85, 94%; 7.00, 93% |
| 32 | 2-(4-Chlorophenyl)-5-(2-(3-(methylamino)pyrrolidin-1-yl)pyrimidin-5-yl)-4,5-dihydropyrrolo[3,4-c]pyrazol-6(2H)-one | X = N TFA salt | 410 | 8.75 (s, 2H), 8.69 (s, 2H), 7.97 (d, J = 11.92 Hz, 2H), 7.65 (d, J = 11.92 Hz, 2H), 4.90 (s, 2H), 3.84 (m, 4H), 2.65 (s, 3H), 2.37 (m, 2H), 2.17 (m, 2H) | 6.10, 91%; 6.93, 92% |

TABLE-continued

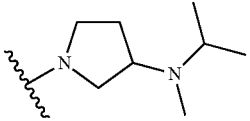

| Ex. No. | Name | R | LC-MS, [M + H]+ | 1H NMR (DMSO-d6, 400 MHz): δ | HPLC-1: Rt min, purity; HPLC-2: Rt min, purity |
|---|---|---|---|---|---|
| 33 | 2-(4-Chlorophenyl)-5-(6-(3-(isopropyl(methyl)amino)pyrrolidin-1-yl)pyridin-3-yl)-4,5-dihydropyrrolo[3,4-c]pyrazol-6(2H)-one | X = CH HCl salt | 451 | 11.04 (s, 1H), 8.71 (s, 1H), 8.51 (d, J = 2.00 Hz, 1H), 8.22 (d, J = 7.60 Hz, 1H), 7.99 (d, J = 9.20 Hz, 2H), 7.66 (d, J = 9.20 Hz, 2H), 6.95 (d, J = 7.60 Hz, 1H), 4.96 (s, 2H), 4.04 (m, 2H), 3.81 (m, 3H), 3.47 (m, 3H), 2.69 (m, 3H), 1.39 (t, J = 6.80 Hz, 3H), 1.25 (t, J = 6.80 Hz, 3H) | 5.58, 96%; 6.68, 96% |

Example 34 tert-Butyl 5-(5-(2-(4-chlorophenyl)-6-oxopyrrolo[3,4-c]pyrazol-5(2H,4H,6H)-yl)pyridin-2-yl)hexahydropyrrolo [3,4-c]pyrrole-2(1H)-carboxylate

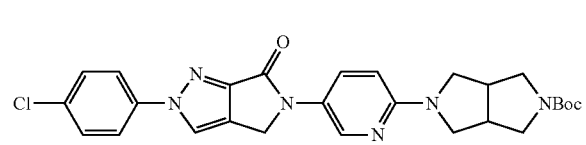 [SMILES: CC(C)(C)OC(=O)N1CC2CN(c3ccc(N4Cc5cn(-c6ccc(Cl)cc6)nc5C4=O)cn3)CC2C1]

Example 34A 2-(4-Chlorophenyl)-5-(6-fluoropridin-3-yl)-4,5-dihydropyrrolo[3,4-c]pyrazol-6(2H)-one

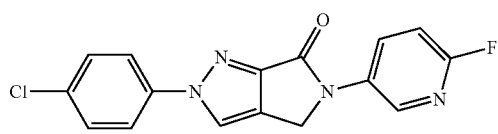 [SMILES: O=C1c2nn(-c3ccc(Cl)cc3)cc2CN1c1ccc(F)nc1]

Example 34A was prepared in a manner analogous to Example 17E except that 6-bromopyridin-3-amine was replaced by 6-fluoropyridin-3-amine. 1H NMR (DMSO-d6, 400 MHz) δ 5.01 (s, 2H), 7.28-7.32 (m, 1H), 7.60-7.67 (m, 2H), 7.92-8.00 (m. 2H), 8.45-8.53 (m, 1H), 8.66 (s, 1H), 8.73 (s, J=2.7 Hz, 1H). LCMS, [M+H]+=329.2.

Example 34 tert-Butyl 5-(5-(2-(4-chlorophenyl)-6-oxopyrrolo[3,4-c]pyrazol-5(2H,4H,6H)-yl)pyridin-2-yl)hexahydropyrrolo[3,4-c]pyrrole-2(1H)-carboxylate

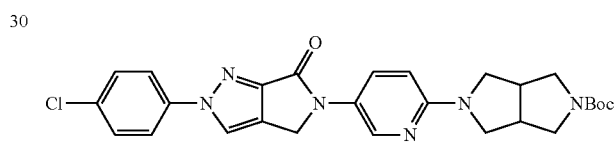

To a mixture of Example 34A (20 mg, 0.061 mmol) in DMSO (0.8 mL) was added tert-butyl hexahydropyrrolo[3,4-c]pyrrole-2(1H)-carboxylate (63 mg, 0.297 mmol). The resulting mixture was irradiated in microwave reactor at 140° C. for 30 min. The sealed tube was heated at 140° C. for 3 h and allowed to cool down to room temperature. The reaction mixture was subjected to filtration. The solid collected was further washed with MeOH (5 mL) and dried under vacuum to give product (19.5 mg) as light yellow solid. 1H NMR (CDCl3, 400 MHz) δ 1.60 (s, 9H), 2.90-3.05 (m, 2H), 3.20-3.50 (m, 4H), 3.60-3.80 (m, 4H), 4.77 (s, 2H), 6.42 (d, J=8.8 Hz, 1H), 7.43-7.50 (m, 2H), 7.72-7.76 (m, 2H), 7.89 (s, 1H), 8.07 (dd, J=8.8, 2.7 Hz, 1H), 8.28 (d, J=2.7 Hz, 1H). LCMS, [M+H]+=521.4.

Example 35

2-(4-Chlorophenyl)-5-(6-(hexahydropyrrolo[3,4-c]pyrrol-2(1H)-yl)pyridin-3-yl)-4,5-dihydropyrrolo[3,4-c]pyrazol-6(2H)one, 2 TFA

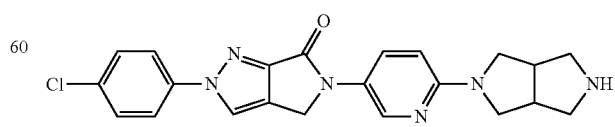

To a solution of Example 34 (17 mg, 0.033 mmol) in CH2Cl2 (1.6 mL) at room temperature was added TFA (0.4 mL). The resulting mixture was stirred at room temperature for 2 h. The solvent was evaporated to give a solid product. The product was washed with cold CH$_2$Cl$_2$ (10 mL) to afford Example 35 (22.3 mg, 99%) as a white solid. LCMS (ES): m/z 421.3 [M+H]$^+$. $^1$H NMR (CD$_3$OD, 400 MHz) δ 3.25-3.90 (m, 10H), 4.93 (s, 2H), 7.02 (d, J=9.0 Hz, 1H), 7.50-7.60 (m, 2H), 7.85-7.92 (m, 2H), 8.25-8.36 (m, 1H), 8.40 (s, 1H), 8.63 (s, 1H).

Example 36

5-(6-(5-Acetylhexahydropyrrolo[3,4-c]pyrrol-2(1H)-yl)pyridin-3-yl)-2-(4-chlorophenyl)-4,5-dihydropyrrolo[3,4-c]pyrazol-6(2H)-one, 2 TFA

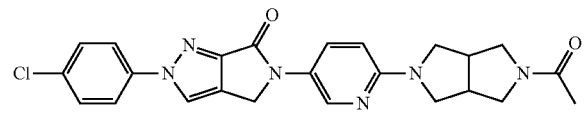 [SMILES: CC(=O)N1CC2CN(c3ccc(N4Cc5cn(-c6ccc(Cl)cc6)nc5C4=O)cn3)CC2C1]

To a solution Example 35, 2 TFA (10 mg, 0.015 mmol) in CH$_2$Cl$_2$ (1.6 mL) at room temperature was added acetic anhydride (250 μL, 2.65 mmol) and pyridine (250 μL, 3.09 mmol). The resulting mixture was stirred at room temperature for 2 h. The solvent was evaporated to give a crude product which was further purified by preparative HPLC (PHENOMENEX® Luna Axia 5μ C18 30×100 mm; 10 min gradient from 60% A: 40% B to 0% A:100% B (A=90% H$_2$O/10% MeOH+0.1% TFA); (B=90% MeOH/10% H$_2$O+0.1% TFA); detection at 220 nm). The desired fraction was collected and concentrated under SPEEDVAC® to give Example 36 as light yellow solid (5.5 mg, 49%). LCMS (ES): m/z 463.4 [M+H]$^+$. $^1$H NMR (CDCl$_3$, 400 MHz) δ 2.10 (s, 3H), 3.15-4.15 (m, 10H), 4.85 (s, 2H), 6.79 (d, J=8.8 Hz, 1H), 7.45-7.50 (m, 2H), 7.72-7.77 (m, 2H), 7.92 (s, 1H), 8.57 (d, J=2.7 Hz, 1H), 9.13 (dd, J=8.8, 2.7 Hz, 1H).

Example 37

5-(6-(5-Benzylhexahydropyrrolo[3,4-c]pyrrol-2(1H)-yl)pyridin-3-yl)-2-(4-chlorophenyl)-4,5-dihydropyrrolo[3,4-c]pyrazol-6(2H)-one, 2TFA

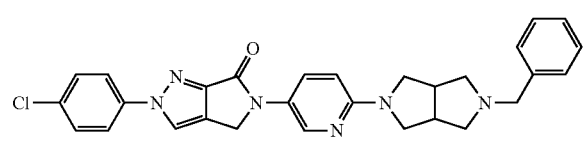 [SMILES: O=C1c2nn(-c3ccc(Cl)cc3)cc2CN1c1ccc(N2CC3CN(Cc4ccccc4)CC3C2)nc1]

To a mixture of Example 34A (20 mg, 0.061 mmol) in DMSO (0.8 mL) was added 2-benzyloctahydropyrrolo[3,4-c]pyrrole (58 mg, 0.287 mmol). The resulting mixture was irradiated in microwave reactor at 120° C. for 30 min. The sealed tube was heated at 120° C. for 3 h and allowed to cool down to room temperature. The reaction mixture was subjected to filtration. The solid collected was further washed with MeOH (8 mL) and dried under vacuum to give product (16 mg). The obtained product was diluted with CH$_2$Cl$_2$ (0.8 mL) and TFA (0.2 ml). The resulting mixture was stirred at room temperature for 15 min. The solvent was evaporated to give a crude product which was further purified by preparative HPLC (PHENOMENEX® Luna Axia 5μ C18 30×100 mm; 10 min gradient from 70% A: 30% B to 0% A:100% B (A=90% H$_2$O/10% MeOH+0.1% TFA); (13=90% MeOH/10% H$_2$O+0.1% TFA); detection at 220 nm). The desired fraction was collected and concentrated under SPEEDVAC® to give Example 37 as white solid (9.2 mg, 38%). $^1$H NMR (CD$_3$OD, 400 MHz) δ 3.02-3.90 (m, 10H), 4.47 (s, 2H), 4.94 (s, 2H), 7.09 (d, J=8.8 Hz, 1H), 7.40-7.53 (m, 7H), 7.60-7.80 (m, 2H), 8.25-8.30 (m, 1H), 8.39 (s, 1H), 8.60 (s, 1H). LCMS, [M+H]$^+$=511.4.

Example 38

(R)-5-(6-(3-Aminopyrrolidin-1-yl)pyridin-3-yl)-2-(4-chlorophenyl)-4,5-dihydropyrrolo[3,4-c]pyrazol-6(2H)-one, 2 TFA

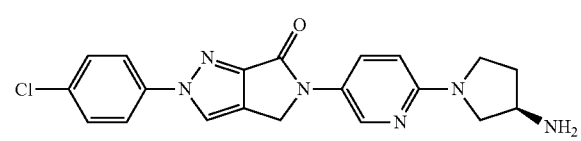 [SMILES: N[C@@H]1CCN(c2ccc(N3Cc4cn(-c5ccc(Cl)cc5)nc4C3=O)cn2)C1]

Example 38A (R)-tort-Butyl 1-(5-(2-(4-chlorophenyl)-6-oxopyrrolo[3,4-c]pyrazol-5(2H,4H,6H)-yl)pyridin-2-yl)pyrrolidin-3-ylcarbamate

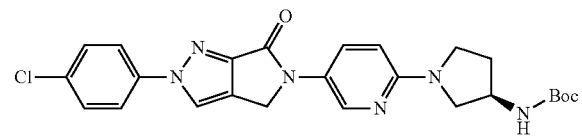 [SMILES: CC(C)(C)OC(=O)N[C@@H]1CCN(c2ccc(N3Cc4cn(-c5ccc(Cl)cc5)nc4C3=O)cn2)C1]

To a mixture of Example 34A (20 mg, 0.061 mmol) in DMSO (0.9 mL) was added (R)-tert-butyl pyrrolidin-3-ylcarbamate (88 mg, 0.472 mmol). The resulting mixture was irradiated in microwave reactor at 120° C. for 30 min. The sealed tube was heated at 140° C. for 3 h and allowed to cool down to room temperature. The reaction mixture was subjected to filtration. The solid collected was further washed with MeOH (8 mL) and dried under vacuum to give product (19.5 mg) as yellow solid.

Example 38

(R)-5-(6-(3-Aminopyrrolidin-1-yl)pyridin-3-yl)-2-(4-chlorophenyl)-4,5-dihydropyrrolo[3,4-c]pyrazol-6(2H)-one, 2 TFA

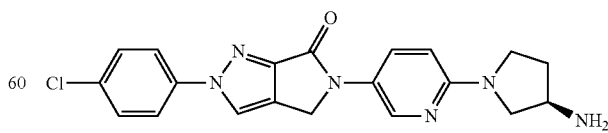

To a solution (Example 38A) (19.5 mg, 0.039 mmol) in CH$_2$Cl$_2$ (1.5 mL) at room temperature was added TFA (0.5 mL). The resulting mixture was stirred at room temperature for 2 h. The solvent was evaporated to give a solid product.

The product was washed with cold Et₂O (10 mL) to afford Example 38 (24.2 mg, 96%) as white solid. LCMS (ES): ink 395.3 [M+H]⁺. ¹H NMR (CD₃OD, 400 MHz) δ 2.25-2.30 (m, 1H), 2.50-2.60 (m, 1H), 3.65-3.82 (m, 3H), 3.85-3.90 (m, 1H), 4.15-4.21 (m, 1H), 4.96 (s, 2H), 7.10 (d, J=8.8 Hz, 1H), 7.50-7.60 (m, 2H), 7.85-7.92 (m, 2H), 8.28 (dd, J=8.8, 2.0 Hz, 1H), 8.39 (s, 1H), 8.61 (d, J=2.0 Hz, 1H).

Example 39

(S)-5-(6-(3-Aminopyrrolidin-1-yl)pyridin-3-yl)-2-(4-chlorophenyl)-4,5-dihydropyrrolo[3,4-c]pyrazol-6(2H)-one, 2 TFA

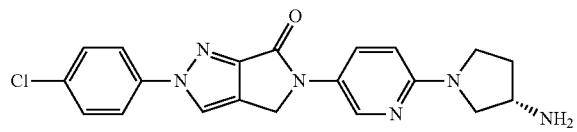

Example 39 was prepared in a manner analogous to Example 38 except that (R)-tert-butyl pyrrolidin-3-ylcarbamate was replaced by (S)-tert-butyl pyrrolidin-3-ylcarbamate. LCMS (ES): m/z 395.0 [M+H]⁺. ¹H NMR (CD₃OD, 400 MHz) δ 2.25-2.32 (m, 1H), 2.50-2.62 (m, 1H), 3.65-3.80 (m, 3H), 3.90-3.98 (m, 1H), 4.10-4.18 (m, 1H), 4.94 (s, 2H), 7.09 (d, J=8.8 Hz, 1H), 7.50-7.58 (m, 2H), 7.85-7.90 (m, 2H), 8.30 (dd, J=8.8, 2.0 Hz, 1H), 8.35 (s, 1H), 8.55 (d, J=8.8 Hz, 1H).

Example 40

(S)-2-(4-Chlorophenyl)-5-(5-methyl-6-(3-(methylamino)pyrrolidin-1-yl)pyridin-3-yl)-4,5-dihydropyrrolo[3,4-c]pyrazol-6(2H)-one, 2 TFA

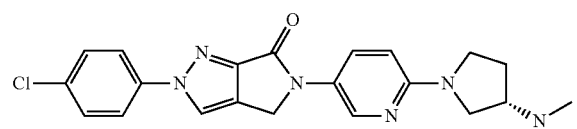

Example 40A (S)-tert-Butyl 1-(5-(1-(4-chlorophenyl)-4-(hydroxymethyl)-1H-pyrazole-3-carboxamido)-3-methylpyridin-2-yl)pyrrolidin-3-yl(methyl)carbamate

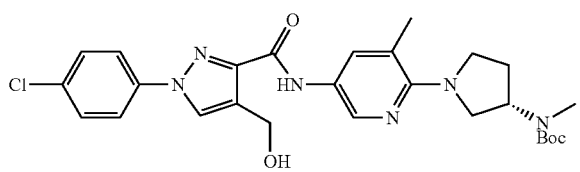

To a solution of Example 17B (49.5 mg, 0.196 mmol), (S)-tert-butyl 1-(5-amino-3-methylpyridin-2-yl)pyrrolidin-3-yl(methyl)carbamate (prepared in a similar manner to that described in *Bioorg. Med. Chem. Leu.*, 15:3701 (2005)) (60 mg, 0.196 mmol) in DCM (6 mL) at RT was added HOBT (36.0 mg, 0.235 mmol) and EDC (45.0 mg, 0.235 mmol). The reaction mixture was allowed to stir for a total of 4 h. The crude was diluted with H₂O (10 mL) and DCM (10 mL). The organic layer was separated, dried over MgSO₄ and concentrated to give a product which was further purified by ISCO automated chromatography (12 g, Hexane/EtOAc, 100:0 to 0:100 gradient) to give Example 40A (102 mg, 96%) as a brown foam.

Example 40B (S)-tert-Butyl 1-(5-(4-(chloromethyl)-1-(4-chlorophenyl)-1H-pyrazole-3-carboxamido)-3-methylpyridin-2-yl)pyrrolidin-3-yl(methyl)carbamate

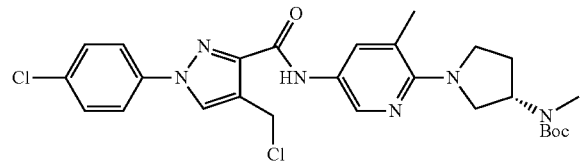 [SMILES: Cc1cc(NC(=O)c2nn(-c3ccc(Cl)cc3)cc2CCl)cnc1N1CC[C@H](N(C)C(=O)OC(C)(C)C)C1]

To a solution of Example 40B (102 mg, 0.189 mmol) and DIPEA (0.033 mL, 0.189 mmol) in DCM (2.5 mL) was added methanesulfonyl chloride (0.025 mL, 0.320 mmol) dropwise at RT and the mixture allowed to stir O.N. Evaporation followed by purification by flash chromatography (12 g silica, 0% to 70% EtOAc-Hexanes) yielded Example 40B (63 mg, 60% yield) as a brown foam. LCMS (ES): m/z 559.3 [M+H]⁺.

Example 40C (S)-tent-Butyl 1-(5-(2-(4-chlorophenyl)-6-oxopyrrolo[3,4-c]pyrazol-5(2H,4H,6H)-yl)-3-methylpyridin-2-yl)pyrrolidin-3-yl(methyl)carbamate To a solution of Example 40B (63 mg, 0.113 mmol) in DMF (1.5 mL) was added K₂CO₃ (43.6 mg, 0.315 mmol) and the mixture was stirred O.N. at R.T. After O.N. stirring, the mixture was treated with H₂O (5 mL). The mixture was filtered. The solid was further washed with water (10 mL), dried under vacuum to yield Example 40C (46.3 mg, 79% yield) as a white solid. LCMS (ES): m/z 523.4 [M+H]⁺. ¹H NMR (CDCl₃, 400 MHz) δ 1.49 (s, 9H), 1.98-2.20 (m, 2H), 2.37 (s, 1H), 2.88 (s, 3H), 3.46-3.60 (m, 4H), 4.78 (s, 2H), 6.45 (d, J=8.8 Hz, 1H), 7.45-7.50 (m, 2H), 7.73-7.79 (m, 2H), 7.89 (s, 1H), 8.01 (d, J=2.1 Hz, 1H), 8.17 (d, J=2.1 Hz, 1H).

Example 40

(S)-2-(4-Chlorophenyl)-5-(5-methyl-6-(3-(methylamino)pyrrolidin-1-yl)pyridin-3-yl)-4,5-dihydropyrrolo[3,4-c]pyrazol-6(2H)-one, 2 TFA

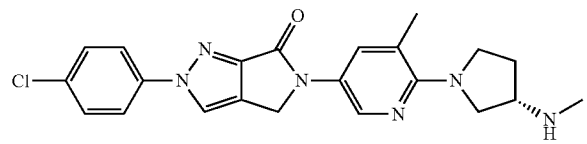 [SMILES: CN[C@H]1CCN(c2ncc(N3Cc4cn(-c5ccc(Cl)cc5)nc4C3=O)cc2C)C1]

To a solution Example 40C (16.33 mg, 0.031 mmol) in CH$_2$Cl$_2$ (1.0 mL) at room temperature was added TFA (0.5 mL). The resulting mixture was stirred at room temperature for 1.5 h. The solvent was evaporated to give a solid product. The product was washed with Et$_2$O (3 mL) to afford Example 40 (22.3 mg) as a white solid. LCMS (ES): m/z 423.3 [M+H]$^+$. $^1$H NMR (DMSO-d$_6$, 400 MHz) δ 2.01-2.10 (m, 1H), 2.22-2.32 (m, 1H), 2.35 (s, 3H), 2.65 (t, J=5.5 Hz, 3H), 3.42-3.52 (m, 1H), 3.52-3.75 (m, 3H), 3.76-3.88 (m, 1H), 4.91 (s, 2H), 7.60-7.66 (m, 2H), 7.93 (d, J=2.0 Hz, 1H), 7.94-7.98 (m, 2H), 8.41 (d, J=2.0 Hz, 1H), 8.68 (s, 1H), 8.65-8.75 (bs, 1H).

Example 41

(S)-tert-Butyl 1-(4-(2-(4-chlorophenyl)-6-oxopyrrolo[3,4-c]pyrazol-5(2H,4H,6H)-yl)-2-methoxyphenyl)pyrrolidin-3-yl(methyl)carbamate

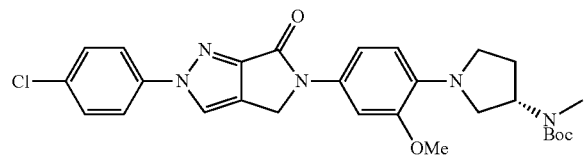 [SMILES: COc1cc(N2Cc3cn(-c4ccc(Cl)cc4)nc3C2=O)ccc1N1CC[C@H](N(C)C(=O)OC(C)(C)C)C1]

Example 41A (S)-1-(2-Methoxy-4-nitrophenyl)-N-methylpyrrolidin-3-amine

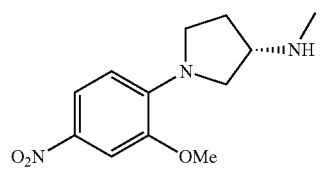 [SMILES: CN[C@H]1CCN(c2ccc([N+](=O)[O-])cc2OC)C1]

A mixture of 1-chloro-2-methoxy-4-nitrobenzene (200 mg, 1.066 mmol) and (S)—N-methylpyrrolidin-3-amine (153 mg, 1.528 mmol) was heated at 130° C. in a sealed tube for 5 h. After cooling down to room temperature, the obtained black solid product (Example 41A) was used for next step without further purification. LCMS (ES): m/z 252.3 [M+H]$^+$.

Example 41

(S)-tert-Butyl 1-(4-(2-(4-chlorophenyl)-6-oxopyrrolo[3,4-c]pyrazol-5(2H,4H,6H)-yl)-2-methoxyphenyl)pyrrolidin-3-yl(methyl)carbamate

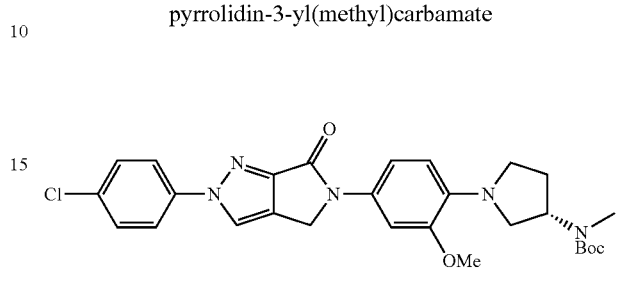

Example 41 was prepared in a manner analogous to Example 40 above, except that (S)-tert-butyl 1-(5-amino-3-methylpyridin-2-yl)pyrrolidin-3-yl(methyl)carbamate was replaced by (S)-tert-butyl 1-(4-amino-2-methoxyphenyl)pyrrolidin-3-yl(methyl)carbamate derived from Example 41A. LC-MS, [M+H]$^+$=538.4. $^1$H NMR (CDCl$_3$, 400 MHz) δ 1.48 (s, 9H), 1.90-2.02 (m, 1H), 2.15-2.25 (m, 1H), 2.89 (s, 3H), 3.20-3.50 (m, 4H), 3.90 (s, 3H), 4.80 (s, 2H), 4.80-5.00 (bs, 1H), 6.78 (d, J=8.8 Hz, 1H), 6.97 (dd, J=8.8, 2.2 Hz, 1H) 7.44-7.48 (m, 2H), 7.64 (d, J=2.1 Hz, 1H), 7.72-7.77 (m, 2H), 7.89 (s, 1H).

Example 42

(S)-2-(4-Chlorophenyl)-5-(3-methoxy-4-(3-(methylamino)pyrrolidin-1-yl)phenyl)-4,5-dihydropyrrolo[3,4-c]pyrazol-6(2H)-one, 2 TFA

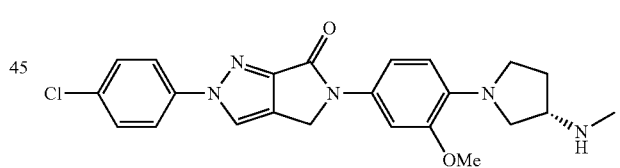

To a solution of Example 41 (25.8 mg, 0.048 mmol) in CH$_2$Cl$_2$ (1.5 mL) at room temperature was added TFA (0.5 mL). The resulting mixture was stirred at room temperature for 3 h. The solvent was evaporated to give a solid product which was further purified by preparative HPLC (PHENOMENEX® Luna Axia 5μ C18 30×100 mm; 10 min gradient from 50% A: 50% B to 0% A:100% B (A=90% H$_2$O/10% MeOH+0.1% TFA); (B=90% MeOH/10% H$_2$O+0.1% TFA); detection at 220 nm). The desired fraction was collected and concentrated under SPEEDVAC® to give Example 42 as light yellow solid (18 mg, 81%). LCMS (ES): m/z 438.3 [M+H]$^+$. $^1$H NMR (CD$_3$OD, 400 MHz) δ 2.02-2.15 (m, 1H), 2.38-2.45 (m, 1H), 2.75 (s, 3H), 3.05-3.30 (m, 2H), 3.50-3.90 (m, 3H), 3.93 (s, 3H), 4.90 (s, 2H), 6.80-6.95 (m, 1H), 7.10-7.20 (m, 1H), 7.45-7.60 (m, 2H), 7.63 (s, 1H), 7.80-7.90 (m, 2H), 8.37 (s, 1H).

Example 43

2-(4-Chlorophenyl)-5-(4-(3-(methylamino)pyrrolidin-1-yl)phenyl)-4,5-dihydropyrrolo[3,4-c]pyrazol-6(2H)-one, 2 HCl

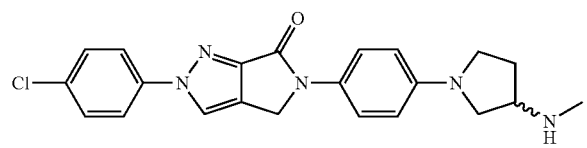 [SMILES: CNC1CCN(c2ccc(N3Cc4cn(-c5ccc(Cl)cc5)nc4C3=O)cc2)C1]

Example 43A

N-Methyl-1-(4-nitrophenyl)pyrrolidin-3-amine

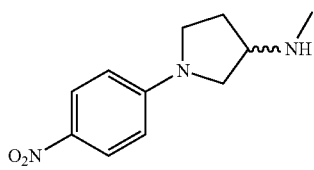 [SMILES: CNC1CCN(c2ccc([N+](=O)[O-])cc2)C1]

N-methylpyrrolidin-3-amine (0.788 g, 7.87 mmol) was added to 1-fluoro-4-nitrobenzene (1.11 g, 7.87 mmol) slowly (CAUTION: extreme exotherm!!!). The resulting mixture was heated at 110° C. for 10 min. After cooling down to room temperature, another portion of amine (0.156 g) was added to the reaction mixture. The resulting mixture was heated at 110° C. for 1 h. After cooling down to room temperature, the obtained black solid product (Example 43A) was used for next step without further purification. LCMS (ES): m/z 252.3 [M+H]$^+$.

Example 43B tert-Butyl 1-(4-(2-(4-chlorophenyl)-6-oxopyrrolo[3,4-c]pyrazol-5(2H,4H,6H)-yl)phenyl)pyrrolidin-3-yl(methyl)carbamate

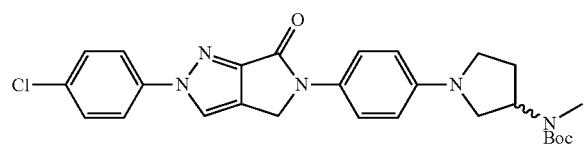 [SMILES: CN(C(=O)OC(C)(C)C)C1CCN(c2ccc(N3Cc4cn(-c5ccc(Cl)cc5)nc4C3=O)cc2)C1]

Example 43B was prepared in a manner analogous to Example 40 above, except that (S)-tert-butyl 1-(5-amino-3-methylpyridin-2-yl)pyrrolidin-3-yl(methyl)carbamate was replaced by tert-butyl 1-(4-aminophenyl)pyrrolidin-3-yl(methyl)carbamate derived from Example 43A. LC-MS, [M+H]$^+$=508.3. $^1$H NMR (CDCl$_3$, 400 MHz) δ 1.48 (s, 9H), 2.05-2.28 (m, 2H), 2.81 (s, 3H), 3.20-3.32 (m, 2H), 3.40-3.52 (m, 2H), 4.75 (s, 2H), 4.80-4.95 (bs, 1H), 6.56-6.64 (m, 2H), 7.43-7.48 (m, 2H), 7.53-7.60 (m, 2H), 7.72-7.77 (m, 2H), 7.87 (s, 1H).

Example 43

2-(4-Chlorophenyl)-5-(4-(3-(methylamino)pyrrolidin-1-yl)phenyl)-4,5-dihydropyrrolo[3,4-c]pyrazol-6(2H)-one, 2 HCl

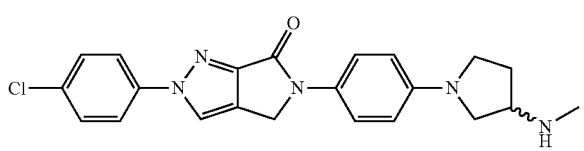

A mixture of Example 43B (38 mg, 0.075 mmol) and 4M HCl in dioxane (2 mL) was stirred at RT for 2 h. MeOH (0.6 mL) was added. The resulting mixture was sonicated for 3 min and stirred at RT for 0.5 h. The solvent was evaporated to give the product as white powder. The product was dissolved in H$_2$O (10 mL) and subjected to lyophilization to give Example 43 (37 mg) as a yellow powder. LC-MS, [M+H]$^+$= 408.3. $^1$H NMR (DMSO-d$_6$, 400 MHz) δ 2.10-2.40 (m, 2H), 2.60 (t, 5.5 Hz, 3H), 3.20-3.58 (m, 4H), 3.85-3.94 (m, 1H), 4.87 (s, 2H), 6.62-6.68 (m, 2H), 7.60-7.68 (m, 4H), 7.93-7.98 (m, 2H), 8.66 (s, 1H), 9.12 (bs, 1H).

Example 44

(S)-Methyl 1-(5-(2-(4-chlorophenyl)-6-oxopyrrolo[3,4-c]pyrazol-5(2H,4H,6H)-yl)pyridin-2-yl)pyrrolidin-3-yl(methyl)carbamate, TFA

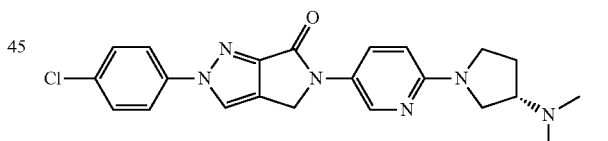

To a mixture of Example 20, 2 TFA (21 mg, 0.038 mmol) in THF (2.5 ml) and H$_2$O (0.2 mL) was added satu aq NaHCO$_3$ solution (0.2 ml) and added methyl carbonochloridate (80 μL, 1.035 mmol). The resulting mixture was stirred at room temperature for 2 h. Organic solvent was evaporated. The mixture was subjected to filtration and the solid product was washed with MeOH (5 mL) to afford desired product (17 mg) as a white solid. The product was diluted with CH$_2$Cl$_2$ (2 mL) and TFA (0.5 mL) was added. The resulting mixture was stirred at room temperature for 5 min. The solvent was evaporated to give the product as white solid. The product was further dried under vacuum to give the product as white solid (22.5 mg). LCMS (ES): ink 467.3 [M+H]$^+$. $^1$H NMR (CD$_3$OD, 400 MHz) δ 2.30-2.40 (m, 2H), 2.94 (s, 3H), 3.55-3.66 (m, 2H), 3.73 (s, 3H), 3.79-3.85 (m, 2H), 4.94 (s, 2H), 7.19 (d, J=8.8 Hz, 1H), 7.52-7.58 (m, 2H), 7.85-7.92 (m, 2H), 8.35-8.42 (m, 2H), 8.68 (d, J=2.2 Hz, 1H).

Example 45

(S)-Methyl 1-(4-(2-(4-chlorophenyl)-6-oxopyrrolo[3,4-c]pyrazol-5(2H,4H,6H)-yl)-2-methoxyphenyl)pyrrolidin-3-yl(methyl)carbamate

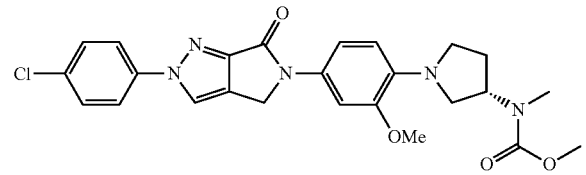

To a mixture of Example 42, 2 HCl (34.5 mg, 0.062 mmol) in THF (4.2 ml) and H$_2$O (0.33 mL) was added satu. act NaHCO$_3$ solution (0.33 ml) and then methyl carbonochloridate (130 μL, 1.682 mmol). The resulting mixture was stirred at room temperature for 2 h. Organic solvent was evaporated. The mixture was subjected to filtration and the solid product was washed with H$_2$O (5 mL) and MeOH (3 mL) to afford the desired product (30 mg) as a yellow solid. LCMS (ES): m/z 496.4 [M+H]$^+$. $^1$H NMR (CDCl$_3$, 400 MHz) δ 1.90-2.05 (m, 1H), 2.15-2.26 (m, 1H), 2.93 (s, 3H), 3.18-3.50 (m, 4H), 3.72 (s, 3H), 3.90 (s, 3H), 4.79 (s, 2H), 4.90-5.02 (bs, 1H), 6.75 (d, J=8.8 Hz, 1H), 6.97 (dd, J=8.8, 2.2 Hz, 1H), 7.43-7.49 (m, 2H), 7.64 (d, J=2.2 Hz, 1H), 7.72-7.76 (m, 2H), 7.88 (s, 1H).

Example 46

(S)—N-(1-(5-(2-(4-Chlorophenyl)-6-oxopyrrolo[3,4-c]pyrazol-5(2H,4H,6H)-yl)pyridin-2-yl)pyrrolidin-3-yl)-N-methylacetamide, TFA

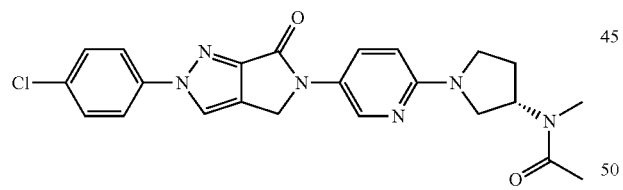 [SMILES: COC(=O)N(C)[C@H]1CCN(c2ccc(N3Cc4cn(-c5ccc(Cl)cc5)nc4C3=O)cn2)C1]

To a mixture of Example 20 (13.9 mg, 0.030 mmol) in CH$_2$Cl$_2$ (1.0 mL) at room temperature was added acetic anhydride (42 μL, 0.445 mmol) and pyridine (48 μL, 0.593 mmol). The resulting mixture was stirred at room temperature for 0.5 h. Another portion of acetic anhydride (200 μL) and pyridine (200 μL) was added. The mixture was heated to reflux for 5 min and then stirred at RT for 18 h. The solvent was evaporated to give a crude product. The product was diluted with cold MeOH (3 mL), stirred for 2 min and subjected to filtration to give Example 46 as light beige solid (8.6 mg). LCMS (ES): m/z 451.3 [M+H]$^+$. $^1$H NMR (CDCl$_3$, 400 MHz) δ 2.05-2.62 (m, 2H), 2.14 (s, 2H), 2.22 (s, 1H), 2.91 (s, 1H), 2.95 (s, 2H), 3.35-3.52 (m, 2H), 3.65-3.75 (m, 2H), 4.62 (m, 0.33H), 4.77 (s, 2H), 5.44 (m, 0.66H), 6.44 (d, J=8.8 Hz, 0.66H), 6.46 (d, J=8.8 Hz, 0.33H), 7.44-7.48 (m, 2H), 7.71-7.76 (m, 2H), 7.89 (s, 1H), 8.08 (dd, J=8.8, 2.2 Hz, 0.66H), 8.12 (dd, J=8.8, 2.2 Hz, 0.33H), 8.28 (d, J=2.2 Hz, 0.66H), 8.29 (d, J=2.2 Hz, 0.33H).

Example 47

(S)-2-(4-Chlorophenyl)-5-(2-(3-(methylamino)pyrrolidin-1-yl)pyrimidin-5-yl)-4,5-dihydropyrrolo[3,4-c]pyrazol-6(2H)-one

Example 47A (S)—N-Methyl-1-(5-nitropyrimidin-2-yl)pyrrolidin-3-amine (S)—N-Methylpyrrolidin-3-amine (286 mg, 2.86 mmol) was added to 2-chloro-5-nitropyrimidine (415 mg, 2.60 mmol) slowly (CAUTION: extreme exotherm!!!). The resulting mixture was heated at 110° C. for 10 min. After cooling down to room temperature, another portion of amine (0.100 g) was added to the reaction mixture. The resulting mixture was heated at 110° C. for 10 min. After cooling down to room temperature, the obtained black solid product (Example 47A) was used for next step without further purification. LCMS (ES): m/z 252.3 [M+H]$^+$.

Example 47

(S)-2-(4-Chlorophenyl)-5-(2-(3-(methylamino)pyrrolidin-1-yl)pyrimidin-5-yl)-4,5-dihydropyrrolo[3,4-c]pyrazol-6(2H)-one, TEA Example 47 was prepared in a manner analogous to Example 40 above, except that (S)-text-butyl 1-(5-amino-3-methylpyridin-2-yl)pyrrolidin-3-yl(methyl)carbamate was replaced by (S)-tert-butyl 1-(5-aminopyrimidin-2-yl)pyrrolidin-3-yl(methyl)carbamate derived from Example 47A. LC-MS, [M+H]$^+$=409.9. $^1$H NMR (DMSO-d$_6$, 400 MHz) δ 2.10-2.20 (m, 1H), 2.28-2.40 (m, 1H), 2.65 (bt, 3H), 3.30-3.90 (m, 5H), 4.90 (s, 2H), 7.62-7.66 (m, 2H), 7.93-7.99 (m, 2H), 8.69 (s, 1H), 8.76 (s, 2H), 8.60-8.80 (bs, 1H).

Example 48

2-(4-Chlorophenyl)-5-(4((3,3-difluoro-1-hydroxycyclobutyl)methoxy)-3-methoxyphenyl)-4,5-dihydropyrrolo[3,4-c]pyrazol-6(2H)-one

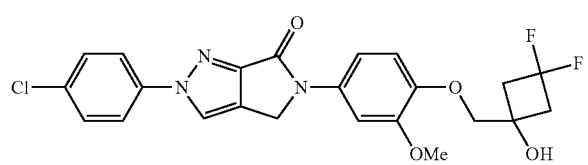 [SMILES: COc1cc(N2Cc3cn(-c4ccc(Cl)cc4)nc3C2=O)ccc1OCC1(O)CC(F)(F)C1]

Example 48A 3,3-Difluoro-N,N-dimethylcyclobutanecarboxamide

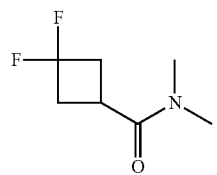

Oxalyl chloride (21.74 mL, 248 mmol) was added dropwise to a stirred solution of 3,3-difluorocyclobutanecarboxylic acid (26 g, 191 mmol; prepared as described in ref: Elend, D. et al., *Syn. Comm.*, 35:657 (2005)) in CH$_2$Cl$_2$ (500 mL) and DMF (0.5 mL) at 0° C. The reaction mixture was allowed to come to RT and stirred at RT for 1 h prior to being concentrated at RT using a rotary evaporator at ca. 50 mm Hg vacuum. After adding THF (300 mL) to the resulting residue, the stirred solution was cooled 0° C. prior to addition of a 2M solution of Me$_2$NH (478 mL, 955 mmol) in THF. After stirring the reaction mixture at RT for 0.5 h, the mixture was partitioned between ether and 5% aq. Na$_2$CO$_3$. The organic layer was dried over MgSO$_4$ and concentrated in vacuo at RT. After portioning the residue between CH$_2$Cl$_2$ and water, the organic layer was dried over MgSO$_4$ and concentrated in vacuo at RT to give 3,3-difluoro-N,N-dimethylcyclobutanecarboxamide (24 g, 147 mmol, 77% yield) as a brown semi solid, used as such in the next step. $^1$H NMR (400 MHz, CDCl$_3$) δ ppm 2.82-3.13 (9H, m), 2.62-2.79 (2 H, m).

Example 48B 1-(3,3-Difluorocyclobutyl)-N,N-dimethylmethanamine

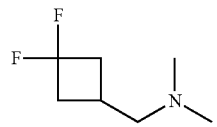

A solution of 3,3-difluoro-N,N-dimethylcyclobutanecarboxamide (24 g, 147 mmol) prepared in Part A in THF (500 mL) was added to a stirred suspension of lithium aluminum hydride (7.5 g, 198 mmol) in 500 mL THF at 0° C. The mixture was allowed to come to RT. After stirring the reaction mixture at RT for 18 h, it was quenched by slowly adding 10 mL 6 N NaOH and 5 mL water at 5° C. with stirring. The mixture was stirred at RT for 0.5 h, dried over Na$_2$SO$_4$ and filtered. The filtrate was concentrated to ca. 30 mL by a careful distillation of most of the THF using a Vigreux column. The remaining material was distilled under slightly reduced pressure (ca. 100-200 mm Hg); the fraction (20 mL, by 70-90° C.) contained the title compound contaminated with THF. The residual THF was carefully purged with a gentle stream of nitrogen to yield 1-(3,3-difluorocyclobutyl)-N,N-dimethylmethanamine (12 g, 80 mmol, 54.7% yield). $^1$H NMR (400 MHz, CDCl$_3$) δ ppm 2.46-2.94 (2 H, m), 2.38 (2 H, d, J=6.55 Hz), 2.16-2.28 (9H, m).

Example 48C 1-(3,3-Difluorocyclobutyl)-N,N-dimethylmethanamine oxide hydrate

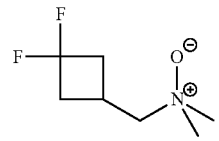

Ref. Cope, A. C. et al., *Org. Syn. Coll.*, IV:612-615; Doering et al., *J. Am. Chem. Soc.*, 89(17):4534 (1967).

30% Aqueous H$_2$O$_2$ (18 mL) was added dropwise to a stirred solution of 1-(3,3-difluorocyclobutyl)-N,N-dimethylmethanamine (12 g, 80 mmol) prepared in Part B in methanol (100 mL) at 5 to 22° C. over 2 h. After stirring at RT for 20 h, additional 30% H$_2$O$_2$ (18 mL) was added. After 3 h, Pd black slurry (150 mg) in water (3 mL) was added to the stirred reaction mixture in small portions such that the temperature could be maintained between 5 to 25° C. with a cooling bath. The reaction mixture was stirred at RT for 1 h until the O$_2$ evolution ceased. After filtration, the filtrate was concentrated in vacuo to give 1-(3,3-difluorocyclobutyl)-N,N-dimethylmethanamine oxide hydrate as a thick colorless oil (15 g, semisolid). $^1$H NMR (400 MHz, CD$_3$OD) δ ppm 3.47 (2 H, d, J=5.29 Hz), 3.16 (6 H, s), 2.75-2.92 H, m), 2.42-2.58 (2 H, Example 48D 1,1-Difluoro-3-methylenecyclobutane

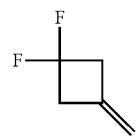

In order to remove most of the water from the sample, 1-(3,3-difluorocyclobutyl)-N,N-dimethylmethanamine oxide hydrate (15 g, 91 mmol) prepared in Part C was heated under vacuum (10 mm) at 100° C. using a distillation setup with the receiving flask cooled to −78° C. Once the water had been removed, the temperature was gradually increased to 165° C. After ca. 1 h most of the starting material had been pyrolized (a small amount of dark brown material remained in the distillation flask). Contents of the receiving flask were then washed sequentially with 5% aq. HCl (3×3 mL) and sat. NaHCO$_3$ (5 mL). The organic layer (olefin) was filtered through Na$_2$SO$_4$ giving 1,1-difluoro-3-methylenecyclobutane (5.5 g, 52.8 mmol, 58.2% yield) as a colorless oil. $^1$H NMR (400 MHz, CDCl$_3$) δ ppm 5.10 (2 H, quin, J=2.52 Hz), 2.77-3.57 (4 H, m).

Example 48E 5,5-Difluoro-1-oxaspiro[2.3]hexane

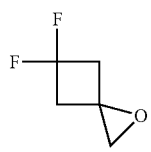

Meta chloroperbenzoic acid (74.6 g, 303 mmol) was added in small portions to a stirred solution of 1,1-difluoro-3-methylenecyclobutane (21.0 g, 202 mmol) prepared in Part D in CH$_2$Cl$_2$ (600 mL) at RT. The reaction mixture cooled with a water bath during the addition. After ca. 1 h the onset of a slight exotherm prompted further cooling using ice-water mixture. The reaction mixture was allowed to come to RT over 3 h. After stirring at RT for 16 h, additional m-CPBA (10 g) was added. The reaction mixture was stirred at RT for 24 h prior to being stored overnight in a refrigerator at 4° C. to precipitate out some of the acids. After filtration, the filtrate was washed with 10% Na$_2$CO$_3$. The organic layer was dried (Na$_2$SO$_4$), concentrated to ca. 170 mL using a Vigreux column. This material was flash distilled at ca. 10 mm to −78° C. traps (two traps in series were employed to minimize loss). The distillate was concentrated using a Vigreux column to a volume of approximately 50 mL affording a 3:1 mixture of CH$_2$Cl$_2$: 5,5-difluoro-1-oxaspiro[2.3]hexane (80 g, 200 mmol, 99% yield) by NMR. This material was used without further purification in the next step. $^1$H NMR (400 MHz, CDCl$_3$ δ ppm 2.91-3.16 (4 H, m), 2.88 (2 H, s).

Example 48F 3,3-Difluoro-1-((2-methoxy-4-nitrophenoxy)methyl)cyclobutanol

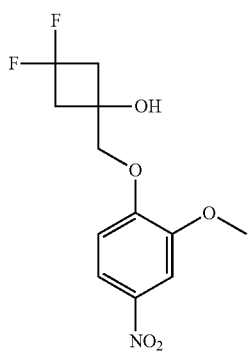

A mixture of 5,5-difluoro-1-oxaspiro[2.3]hexane+3 eq. CH$_2$Cl$_2$ (22.52 g, 0.06 mol), potassium 2-methoxy-4-nitrophenolate (12.43 g, 0.060 mol) prepared in Part E and NaH$_2$PO$_4$.H$_2$O (7.45 g, 0.054 mol) in 50 mL MeCN-water (85:15) was heated at 130° C. in a steel bomb for 3.5 h. The reaction mixture was diluted with EtOAc, washed with 5% Na$_2$CO$_3$, dried (MgSO$_4$) and concentrated. The crude product was recrystallized from ca. 150 mL MTBE giving 3,3-difluoro-1-((2-methoxy-4-nitrophenoxy)methyl)cyclobutanol (11.2 g, 0.039 mol, 64.5% yield) as a light yellow solid. An additional 1.2 g of a slightly less pure desired product was obtained upon concentration of the mother liquor to ca. 50 mL. $^1$H NMR (400 MHz, CDCl$_3$) δ ppm 7.89 (1H, dd, J=8.94, 2.64 Hz), 7.76 (1H, d, J=2.77 Hz), 6.95 (1H, d, J=9.06 Hz), 4.16 (2 H, s), 3.94 (3 H, s), 3.36 (1H, s), 2.73-2.92 (4 H, m).

Example 48G 1-((4-Amino-2-methoxyphenoxy)methyl)-3,3-difluorocyclobutanol

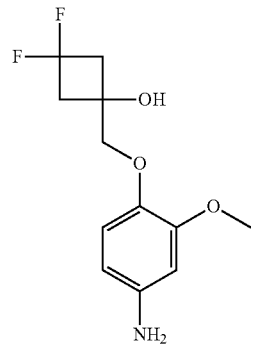 [SMILES: COc1cc(N)ccc1OCC1(O)CC(F)(F)C1]

A mixture of 3,3-difluoro-1-((2-methoxy-4-nitrophenoxy)methyl)cyclobutanol (32.0 g, 111 mmol) prepared in Part F and 10% Pd/C (2.0 g, 1.879 mmol) in 700 mL MeOH was stirred under H$_2$ at 50 psi for 1.5 h. After filtration, the filtrate was concentrated to give 1-((4-amino-2-methoxyphenoxy)methyl)-3,3-difluorocyclobutanol (28.9 g, 111 mmol, quantitative yield) as a light purple solid. $^1$H NMR (400 MHz, CD$_3$OD) δ ppm 6.68 (1H, d, J=8.56 Hz), 6.35 (1 H, d, J=2.52 Hz), 6.16 (1 H, dd, J=8.31, 2.52 Hz), 4.77 (3 H, br. s.), 3.78 (2 H, s), 3.68 (3 H, s), 2.68-2.82 (2 H, m), 2.38-2.56 (2 H, m).

Example 48H

Ethyl 1-(4-chlorophenyl)-3-(4-((3,3-difluoro-1-hydroxycyclobutyl)methoxy)-3-methoxyphenylcarbamoyl)-1H-pyrazole-4-carboxylate

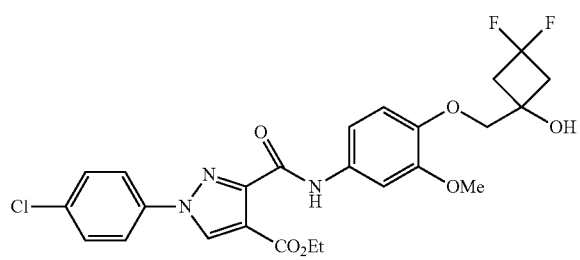 [SMILES: CCOC(=O)c1cn(-c2ccc(Cl)cc2)nc1C(=O)Nc1ccc(OCC2(O)CC(F)(F)C2)c(OC)c1]

To a solution of Example 5A (0.15 g, 0.509 mmol), 1-((4-amino-2-methoxyphenoxy)methyl)-3,3-difluorocyclobutanol (Example 48G, 0.132 g, 0.509 mmol) in DCM (17 mL) at RT was added HOBT (0.101 g, 0.662 mmol) and EDC (0.127 g, 0.662 mmol). The reaction mixture was allowed to stir for a total of 6 h. The crude was diluted with H$_2$O (10 mL) and DCM (10 mL). The organic layer was separated, dried over MgSO$_4$ and concentrated to give a product which was further purified by ISCO automated chromatography (12 g, Hexane/EtOAc, 100:0 to 0:100 gradient) to give Example 48H (206 mg, 76%) as a white solid. LCMS (ES): m/z 536.0 [M+H].

Example 48I

Ethyl 1-(4-chlorophenyl)-3-(4((3,3-difluoro-1-((2-(trimethylsilyl)ethoxy)methoxy)cyclobutyl)methoxy)-3-methoxyphenylcarbamoyl)-1H-pyrazole-4-carboxylate

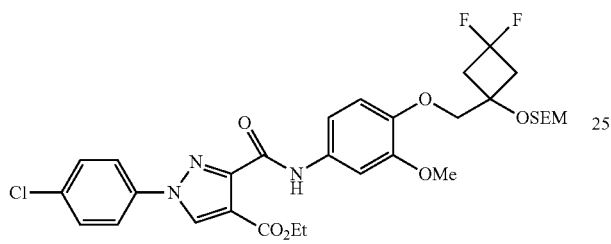

To a mixture of Example 48H (206 mg, 0.384 mmol) in CH$_2$Cl$_2$ (1.5 mL) at 0° C. was added SEM-Cl (0.102 mL, 0.577 mmol) and diisopropylethylamine (0.134 mL, 0.769 mmol). The resulting mixture was stirred at this temperature for 10 min then allowed to warm to room temperature for 0.5 h. Another portion of SEM-Cl (0.102 mL, 0.577 mmol) and diisopropylethylamine (0.134 mL, 0.769 mmol) was added. After stirring at room temperature overnight, the solvent was evaporated. The crude residue was diluted with EtOAc (30 mL) and washed with H$_2$O (8 mL). The organic layer was separated, dried over MgSO$_4$ and concentrated to give the crude product which was further purified by ISCO automated chromatography (12 g, Hexane/EtOAc, 100:0 to 66:33 gradient) to give Example 48I (202 mg, 79% yield) as a white solid.

Example 48J 1-(4-Chlorophenyl)-N-(4-3,3-difluoro-1-((2-(trimethylsilyl)ethoxy)methoxy)cyclobutyl)methoxy)-3-methoxyphenyl)-4-(hydroxymethyl)-1H-pyrazole-3-carboxamide

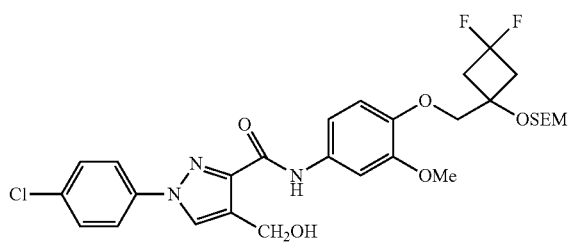

To a solution of Example 48I (202 mg, 0.303 mmol) in THF (10 mL) was added 2M LiBH$_4$ in THF (0.394 mL, 0.788 mmol) dropwise and the resulting mixture was allowed to stir for 4 h. The mixture was quenched with sat aq. NaHCO$_3$, extracted into EtOAc, and the organic layer was washed with brine, dried (Na$_2$SO$_4$), filtered, and evaporated to yield the crude alcohol, which was purified by flash chromatography (12 g silica, 0% to 100% EtOAc-Hexanes) to yield Example 48J (170 mg, 90% yield) as a yellow foam. LCMS (ES): m/z 624.6 [M+H]$^+$. $^1$H NMR (CDCl$_3$, 400 MHz) δ 0.00 (s, 9H), 0.85-0.93 (m, 2H), 2.83-2.93 (m, 4H), 3.65-3.72 (m, 2H), 3.88 (s, 3H), 4.15 (s, 2H), 4.73-4.78 (m, 2H), 4.88 (s, 2H), 6.92 (d, J=8.8 Hz, 1H), 7.02 (dd, J=8.8, 2.0 Hz, 1H), 7.45-7.49 (m, 3H), 7.59 (d, J=2.0 Hz, 1H), 7.67-7.71 (m, 2H), 7.85 (s, 1H), 8.80 (s, 1H).

Example 48K 4-(Chloromethyl)-1-(4-chlorophenyl)-N-(4-((3,3-difluoro-1-((2-(trimethylsilyl)ethoxy)methoxy)cyclobutyl)methoxy)-3-methoxyphenyl)-1H-pyrazole-3-carboxamide

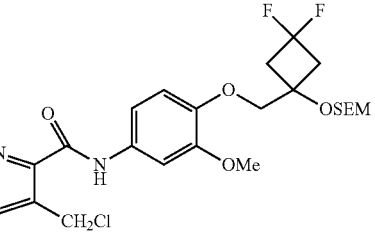

To a solution of Example 48J (170 mg, 0.272 mmol) and DIPEA (0.085 mL, 0.487 mmol) in DCM (8 mL) was added methanesulfonyl chloride (34 μL, 0.436 mmol) dropwise at RT and the mixture allowed to stir O.N. Evaporation followed by purification by flash chromatography (12 g silica, 0% to 40% EtOAc-Hexanes) yielded Example 48K (131 mg, 75% yield) as a white foam. $^1$H NMR (CDCl$_3$, 400 MHz) δ 0.00 (s, 9H), 0.85-0.93 (m, 2H), 2.83-2.93 (m, 4H), 3.66-3.72 (m, 2H), 3.88 (s, 3H), 4.12 (s, 2H), 4.88 (s, 2H), 5.01 (s, 2H), 6.90 (d, J=8.8 Hz, 1H), 7.04 (dd, J=8.8, 2.0 Hz, 1H), 7.45-7.53 (m, 2H), 7.62 (d, J=2.0 Hz, 1H), 7.65-7.70 (m, 2H), 8.03 (s, 1H), 8.68 (s, 1H).

Example 48L 2-(4-Chlorophenyl)-5-(4-((3,3-difluoro-1-((2-(trimethylsilyl)ethoxy)methoxy)cyclobutyl)methoxy)-3-methoxyphenyl)-4,5-dihydropyrrolo[3,4-c]pyrazol-6(2H)-one

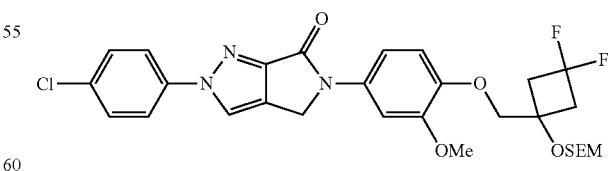

To a solution of Example 48K (131 mg, 0.204 mmol) in DMF (2.5 mL) was added K$_2$CO$_3$ (7 mg, 0.57 mmol) and the mixture was stirred O.N. at R.T. After O.N. stirring, the mixture was treated with H$_2$O (6 mL). The mixture was filtered. The solid was further washed with water (20 mL), dried under vacuum to yield Example 48L (111 mg, 90% yield) as a white solid. LC-MS, [M+H]$^+$=606.0. $^1$H NMR (CDCl$_3$, 400 MHz)

δ 0.00 (s, 9H), 0.87-0.92 (m, 2H), 2.85-2.93 (m, 4H), 3.65-3.72 (m, 2H), 3.89 (s, 3H), 4.15 (s, 2H), 4.80 (s, 2H), 4.88 (s, 2H), 6.90-7.03 (m, 2H), 7.44-7.49 (m, 2H), 7.68-7.76 (m, 3H), 7.89 (s, 1H).

Example 48

2-(4-Chlorophenyl)-5-(4((3,3-difluoro-1-hydroxycyclobutyl)methoxy)-3-methoxyphenyl)-4,5-dihydropyrrolo[3,4-c]pyrazol-6(2H)-one

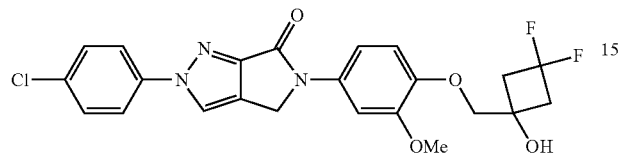

To a solution of Example 48L (111 mg, 0.183 mmol) in DCM (5 mL) at 0° C. was added TPA (125 µL) dropwise. The mixture was stirred O.N. at R.T. Solvent was evaporated and the crude product was purified by flash chromatography (12 g silica, 0% to 100% EtOAc-Hexanes) to yield Example 48 (55 mg, 60% yield) as white solid. LC-MS, [M+H]+=475.9. ¹H NMR (CDCl₃, 400 MHz) δ 2.70-2.83 (m, 4H), 3.73 (s, 1H), 3.92 (s, 3H), 4.07 (s, 2H), 4.80 (s, 2H), 6.99 (s, 2H), 7.45-7.50 (m, 2H), 7.70-7.76 (m, 2H), 7.78 (s, 1H), 7.89 (s, 1H).

Example 49

1-((4-(2-(4-Chlorophenyl)-6-oxopyrrolo[3,4-c]pyrazol-5(2H,4H,6H)-yl)-2-methoxyphenoxy)methyl)-3,3-difluorocyclobutyl 2-aminoacetate, HCl salt

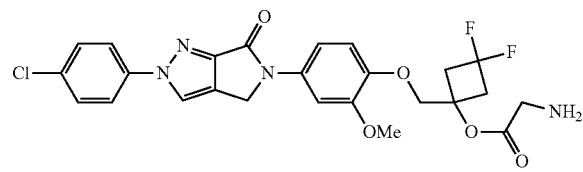 [SMILES: COc1cc(N2Cc3cn(-c4ccc(Cl)cc4)nc3C2=O)ccc1OCC1(OC(=O)CN)CC(F)(F)C1]

Example 49A 1-((4-(2-(4-Chlorophenyl)-6-oxopyrrolo[3,4-c]pyrazol-5(2H,4H,6H)-yl)-2-methoxyphenoxy)methyl)-3,3-difluorocyclobutyl 2-(tert-butoxycarbonylamino)acetate

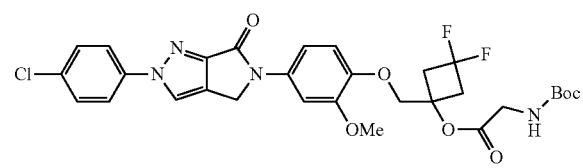 [SMILES: COc1cc(N2Cc3cn(-c4ccc(Cl)cc4)nc3C2=O)ccc1OCC1(OC(=O)CNC(=O)OC(C)(C)C)CC(F)(F)C1]

To a solution of Example 48 (50 mg, 0.105 mmol) and 2-(tert-butoxycarbonylamino)acetic acid (92 mg, 0.525 mmol) in DCM (1.5 mL) was added 4-(pyrrolidin-1-yl)pyridine (78 mg, 0.525 mmol) and EDC (0.101 g, 0.525 mmol) at RT. The resulting mixture was heated to reflux for 15 min. Solvent was evaporated. The crude residue was diluted with EtOAc (30 mL) and washed with 0.5 N HCl (3 mL) and H₂O (3 mL). The organic layer was separated, dried over MgSO₄ and concentrated to give the crude product which was further purified by ISCO automated chromatography (12 g silica, 0% to 60% EtOAc-Hexanes) to yield Example 49A (46 mg, 69% yield) as a white solid. ¹H NMR (CDCl₃, 400 MHz) δ 1.44 (s, 9H), 2.88-3.01 (m, 2H), 3.10-3.20 (m, 2H), 3.85 (d, J=5.5 Hz, 2H), 3.90 (s, 3H), 4.37 (s, 2H), 4.80 (s, 2H), 4.95-5.01 (bt, 1H), 6.93-6.98 (m, 2H), 7.44-7.49 (m, 2H), 7.70-7.78 (m, 3H), 7.89 (s, 1H).

Example 49

1-((4-(2-(4-Chlorophenyl)-6-oxopyrrolo[3,4-c]pyrazol-5(2H,4H,6H)-yl)-2-methoxyphenoxy)methyl)-3,3-difluorocyclobutyl 2-aminoacetate, HCl

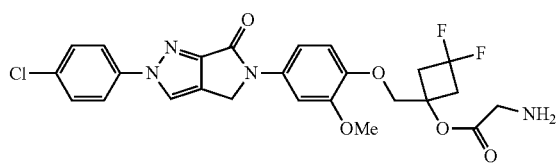 [SMILES: COc1cc(N2Cc3cn(-c4ccc(Cl)cc4)nc3C2=O)ccc1OCC1(OC(=O)CN)CC(F)(F)C1]

A mixture of Example 49A (46 mg, 0.073 mmol) in 4N HCl in dioxane (1.5 mL) was stirred at RT for 1 h. Most of the solvent was evaporated. The resulting slurry was diluted with Et₂O (20 mL). The mixture was stirred for 5 min and subjected to filtration. The solid was washed with Et₂O (2×10 ml), dried under vacuum to give Example 49 as white solid (32 mg, 73%). LC-MS, [M+H]+=539.1.

¹H NMR (DMSO-d₆, 400 MHz): δ 3.00-3.25 (m, 4H), 3.81 (s, 3H), 4.33 (s, 2H), 4.95 (s, 2H), 7.06 (d, J=8.8 Hz, 1H), 7.27 (dd, J=8.8, 2.0 Hz, 1H), 7.59 (d, J=2.0 Hz, 1H), 7.62-7.66 (m, 2H), 7.94-7.98 (m, 2H), 8.10-8.20 (bs, 2H), 8.69 (s, 1H).

Example 50

1-((4-(2-(4-Chlorophenyl)-6-oxopyrrolo[3,4-c]pyrazol-5(2H,4H,6H)-yl)-2-methoxyphenoxy)methyl)-3,3-difluorocyclobutyl dihydrogen phosphate

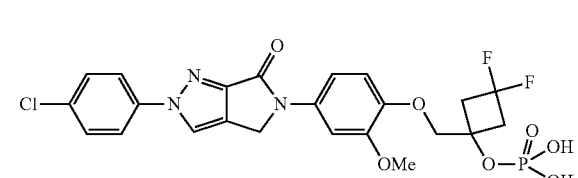

Example 50A

Dibenzyl 1-((4-(2-(4-chlorophenyl)-6-oxopyrrolo[3,4-c]pyrazol-5(2H,4H,6H)-yl)-2-methoxyphenoxy)methyl)-3,3-difluorocyclobutyl phosphate

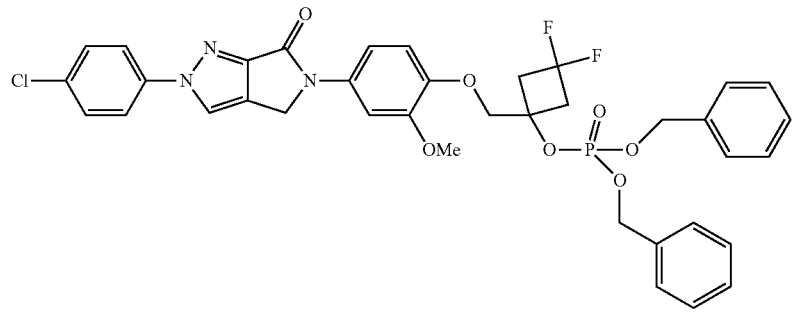 [SMILES: COc1cc(N2Cc3cn(-c4ccc(Cl)cc4)nc3C2=O)ccc1OCC1(OP(=O)(OCc2ccccc2)OCc2ccccc2)CC(F)(F)C1]

A mixture of Example 48 (33 mg, 0.069 mmol), dibenzyl diisopropylphosphoramidite (71.9 mg, 0.208 mmol) and 1H-1,2,4-triazole (14.37 mg, 0.208 mmol) in DCE (1 mL) was heated at reflux temperature for 1 h. The above mixture was allowed to come to RT, added hydrogen peroxide (0.07 mL, 0.685 mmol, 30% wt) and stirred for 15 minutes at RT. The mixture was diluted with CH$_2$Cl$_2$ (10 mL), washed sequentially with water, 5% aq. sodium thiosulfate and water. The organic layer was dried over MgSO$_4$ and concentrated to give the crude product which was further purified by ISCO automated chromatography (12 g, Hexane/EtOAc, 100:0 to 0:100 gradient) to give Example 50A (47 mg, 92% yield) as a white solid. LC-MS, [M+H]$^+$=736.5. $^1$H NMR (CDCl$_3$, 400 MHz) δ 3.01-3.20 (m, 4H), 3.80 (s, 3H), 4.28 (s, 2H), 4.75 (s, 2H), 5.06 (d, J=12.5 Hz, 1H), 5.08 (d, J=12.5 Hz, 1H), 6.85-6.92 (m, 2H), 7.28-7.3 (m, 10H), 7.44-7.50 (m, 2H), 7.70-7.78 (m, 3H), 7.89 (s, 1H).

Example 50

1-((4-(2-(4-Chlorophenyl)-6-oxopyrrolo[3,4-c]pyrazol-5(2H,4H,6H)-yl)-2-methoxyphenoxy)methyl)-3,3-difluorocyclobutyl dihydrogen phosphate

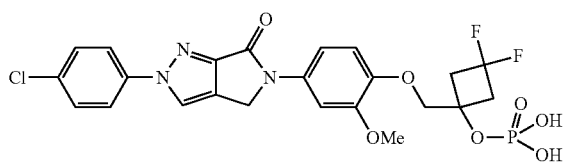 [SMILES: COc1cc(N2Cc3cn(-c4ccc(Cl)cc4)nc3C2=O)ccc1OCC1(OP(=O)(O)O)CC(F)(F)C1]

To a solid of Example 50A (39 mg, 0.053 mmol) was added TFA (0.7 mL). The resulting yellow mixture was allowed to stir at RT for 3 h. Solvent was evaporated. The crude was dissolved in MeOH (2 mL) and purification by Preparative HPLC (PHENOMENEX® Luna Axia 5μ C18 30×100 mm; 10 min gradient from 70% A: 30% B to 0% A:100% B (A=90% H$_2$O/10% ACN+0.1% TFA); (B=90% ACN/10% H$_2$O+0.1% TFA); detection at 220 nm) yielded Example 50 (20 mg, 65% yield) as a white solid. LC-MS, [M+H]$^+$=556.4. $^1$H NMR (DMSO-d$_6$, 400 MHz): δ 2.93-3.25 (m, 4H), 3.28-3.40 (bs, 2H), 3.81 (s, 3H), 4.19 (s, 2H), 4.94 (s, 2H), 7.06 (d, J=8.8 Hz, 1H), 7.27 (dd, J=8.8, 2.0 Hz, 1H), 7.59 (d, J=2.0 Hz, 1H), 7.60-7.65 (m, 2H), 7.93-7.98 (m, 2H), 8.68 (s, 1H).

Example 51

1-(4-(2-(4-Chlorophenyl)-6-oxopyrrolo[3,4-c]pyrazol-5(2H,4H,6H)-yl)-2-methoxyphenoxy)-2-methylpropan-2-yl 2-aminoacetate, HCl

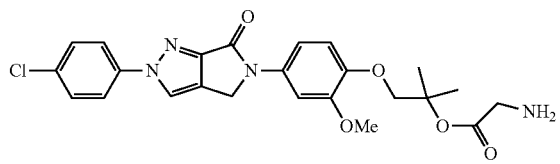 [SMILES: COc1cc(N2Cc3cn(-c4ccc(Cl)cc4)nc3C2=O)ccc1OCC(C)(C)OC(=O)CN]

Example 51A 1-((4-(2-(4-Chlorophenyl)-6-oxopyrrolo[3,4-c]pyrazol-5(2H,4H,6H)-yl)-2-methoxyphenoxy)methyl)-3,3-difluorocyclobutyl 2-(tert-butoxycarbonylamino)acetate

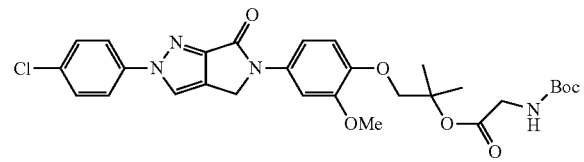 [SMILES: COc1cc(N2Cc3cn(-c4ccc(Cl)cc4)nc3C2=O)ccc1OCC(C)(C)OC(=O)CNC(=O)OC(C)(C)C]

Example 51A was prepared in a manner analogous to Example 40 above, except that (S)-tert-butyl 1-(5-amino-3-methylpyridin-2-yl)pyrrolidin-3-yl(methyl)carbamate was replaced by 1-(4-amino-2-methoxyphenoxy)-2-methylpropan-2-yl 2-(tert-butoxycarbonylamino)acetate. LC-MS, [M+H]$^+$=603.4. $^1$H NMR (CDCl$_3$, 400 MHz) δ 1.44 (s, 9H), 1.61 (s, 3H), 1.62 (s, 3H), 3.81 (d, J=5.2 Hz, 2H), 3.90 (s, 3H), 4.16 (s, 2H), 4.79 (s, 2H), 4.99 (bt, 1H), 6.92 (d, J=8.8 Hz, 1H), 6.99 (dd, J=8.8, 2.0 Hz, 1H), 7.43-7.50 (m, 2H), 7.67 (d, J=2.0 Hz, 1H), 7.72-7.75 (m, 2H), 7.88 (s, 1H).

Example 51

1-(4-(2-(4-Chlorophenyl)-6-oxopyrrolo[3,4-c]pyrazol-5(2H,4H,6H)-yl)-2-methoxyphenoxy)-2-methylpropan-2-yl 2-aminoacetate

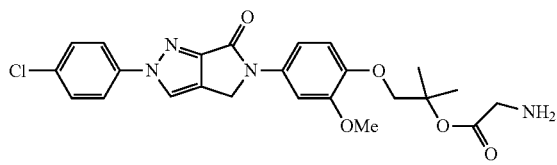 [SMILES: COc1cc(N2Cc3cn(-c4ccc(Cl)cc4)nc3C2=O)ccc1OCC(C)(C)OC(=O)CN]

A mixture of Example 51A (2.23 g, 3.81 mmol) in 4N HCl in dioxane (180 mL) was stirred at RT for 2.5 h. Most of the solvent was evaporated. The resulting slurry was diluted with Et$_2$O (200 ml). The mixture was stirred for 5 min and subjected to filtration. The solid was washed with Et$_2$O (2×100 ml), dried under vacuum to give Example 51 as white solid (2.38 g). LC-MS, [M+H]$^+$=485.0. $^1$H NMR (CD$_3$OD, 400 MHz): δ 1.64 (s, 6H), 3.74 (s, 2H), 3.89 (s, 3H), 4.23 (s, 2H), 4.93 (s, 2H), 7.03 (d, J=8.8 Hz, 1H), 7.15 (dd, J=8.8, 2.0 Hz, 1H), 7.52-7.57 (m, 2H), 7.58 (d, J=2.0 Hz, 1H), 7.85-7.90 (m, 2H), 8.34 (s, 1H).

Example 52

2-(4-Chlorophenyl)-5-(4-((3S,4S)-3,4-dihydroxypyrrolidin-1-yl)-3-methoxyphenyl)-4,5-dihydropyrrolo[3,4-c]pyrazol-6(2H)-one, TFA

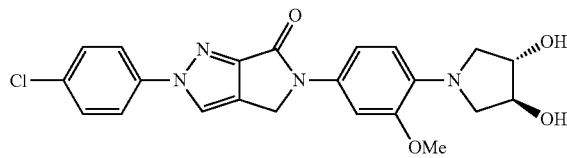 [SMILES: COc1cc(N2Cc3cn(-c4ccc(Cl)cc4)nc3C2=O)ccc1N1C[C@H](O)[C@@H](O)C1]

Example 52A (3S,4S)-1-(2-Methoxy-4-nitrophenyl)pyrrolidine-3,4-diol

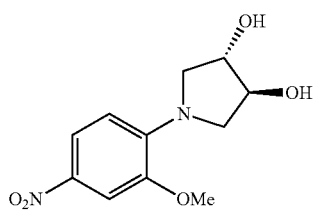 [SMILES: COc1cc([N+](=O)[O-])ccc1N1C[C@H](O)[C@@H](O)C1]

A mixture of 1-chloro-2-methoxy-4-nitrobenzene (488 mg, 2.60 mmol) and (3S,4S)-pyrrolidine-3,4-diol (268 mg, 2.60 mmol) and DIEA (0.454 ml, 2.60 mmol) in acetonitrile (1 mL) was heated at 110° C. in a sealed tube for 4 h. After cooling down to room temperature, the obtained crude product was further purified by ISCO automated chromatography (12 g, CH$_2$Cl$_2$/MeOH, 100:0 to 92:8 gradient) to give Example 52A (250 mg, 38%) as a solid yellow foam. LCMS (ES): m/z 255.3 [M+H]$^+$.

Example 52B (3S,4S)-1-(2-Methoxy-4-nitrophenyl)-3,4-bis((2-(trimethylsilyl)ethoxy)methoxy)pyrrolidine

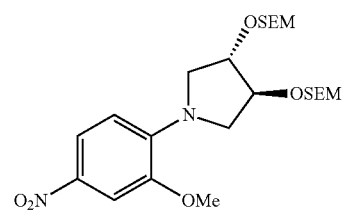

To a mixture of Example 52A (250 mg, 0.983 mmol) in CH$_2$Cl$_2$ (1 mL) at 0° C. was added SEM-Cl (0.523 mL, 2.95 mmol) and diisopropylethylamine (0.687 mL, 3.93 mmol). The resulting mixture was stirred at this temperature for 10 min then allowed to warm to room temperature for 0.5 h. After stirring at room temperature overnight, another portion of SEM-Cl (0.2 mL) and diisopropylethylamine (0.3 mL) were added. The resulting mixture was stirred at RT for 2 days. Solvent was evaporated. The crude residue was diluted with EtOAc (30 mL) and washed with H$_2$O (8 mL). The organic layer was separated, dried over MgSO$_4$ and concentrated to give the crude product which was further purified by ISCO automated chromatography (40 g, Hexane/EtOAc, 100:0 to 60:40 gradient) to give Example 52B (248 mg, 49% yield) as a yellow oil. LCMS (ES): m/z 515.5 [M+H]$^+$.

Example 52

(2-(4-Chlorophenyl)-5-(4-((3S,4S)-3,4-dihydroxypyrrolidin-1-yl)-3-methoxyphenyl)-4,5-dihydropyrrolo[3,4-c]pyrazol-6(2H)-one, TFA

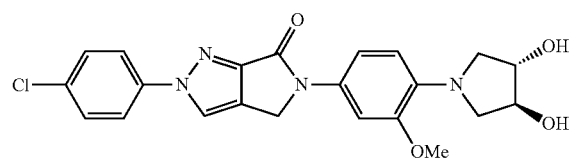 [SMILES: COc1cc(N2Cc3cn(-c4ccc(Cl)cc4)nc3C2=O)ccc1N1C[C@H](O)[C@@H](O)C1]

Example 52 was prepared in a manner analogous to Example 40 above, except that (S)-tert-butyl 1-(5-amino-3-methylpyridin-2-yl)pyrrolidin-3-yl(methyl)carbamate was replaced by 4-((3S,4S)-3,4-bis((2-(trimethylsilyl)ethoxy)methoxy)pyrrolidin-1-yl)-3-methoxyaniline derived from Example 52B. LCMS (ES): m/z 441.5 [M+H]$^+$. $^1$H NMR (DMSO-d$_6$, 400 MHz) δ 3.03-3.09 (m, 2H), 3.55-3.62 (m, 2H), 3.76 (s, 3H), 3.93-3.96 (m, 2H), 4.89 (s, 2H), 4.90 (bs, 2H), 6.60 (d, J=8.8 Hz, 1H), 7.15 (dd, J=8.8, 2.0 Hz, 1H), 7.44 (d, J=2.0 Hz, 1H), 7.60-7.65 (m, 2H), 7.94-7.99 (m, 2H), 8.65 (s, 1H).

Example 53

(R)-2-(4-Chlorophenyl)-5-(4-(3-hydroxypyrrolidin-1-yl)-3-methoxyphenyl)-4,5-dihydropyrrolo[3,4-c]pyrazol-6(2H)-one, TFA

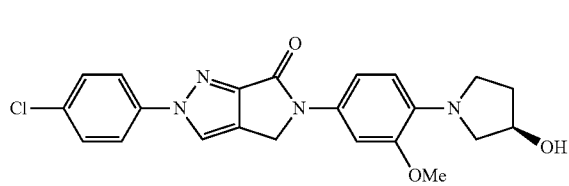 [SMILES: COc1cc(N2Cc3cn(-c4ccc(Cl)cc4)nc3C2=O)ccc1N1CC[C@@H](O)C1]

Example 53A (R)-1-(2-Methoxy-4-nitrophenyl)pyrrolidin-3-ol

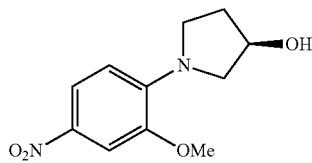

A mixture of 1-chloro-2-methoxy-4-nitrobenzene (500 mg, 2.67 mmol) and (R)-pyrrolidin-3-ol (325 mg, 3.73 mmol), and DIEA (0.454 ml, 2.60 mmol) in acetonitrile (1 mL) was heated at 130° C. in a sealed tube for 3 h. After cooling down to room temperature, the obtained crude product was further purified by ISCO automated chromatography (12 g, CH$_2$Cl$_2$/MeOH, 100:0 to 92:8 gradient) to give Example 52A (236 mg, 37.2%) as an orange foam. LCMS (ES): m/z 239.4 [M+H].

Example 53

(R)-2-(4-Chlorophenyl)-5-(4-(3-hydroxypyrrolidin-1-yl)-3-methoxyphenyl)-4,5-dihydropyrrolo[3,4-c]pyrazol-6(2H)-one, TFA

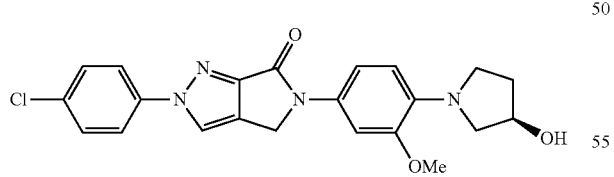

Example 53 was prepared in a manner analogous to Example 40 above, except that (S)-tert-butyl 1-(5-amino-3-methylpyridin-2-yl)pyrrolidin-3-yl(methyl)carbamate was replaced by (R)-3-methoxy-4-(3-((2-(trimethylsilyl)ethoxy)methoxy)pyrrolidin-1-yl)aniline derived from Example 53A. LCMS (ES): m/z 425.4 [M+H]$^+$. $^1$H NMR (CD$_3$OD, 400 MHz) δ 2.00-2.15 (m, 1H), 2.25-2.38 (m, 1H), 3.35-3.65 (m, 2H), 3.70-3.85 (m, 2H), 3.98 (s, 3H), 4.55-4.60 (m, 1H), 4.94 (s, 2H), 7.27 (s, 2H), 7.52-7.57 (m, 2H), 7.86 (s, 1H), 7.87-7.99 (m, 2H), 8.35 (s, 1H).

Example 54

2-(4-Chlorophenyl)-5-(6-(3-hydroxyazetidin-1-yl)pyridin-3-yl)-4,5-dihydropyrrolo[3,4-c]pyrazol-6(2H)-one

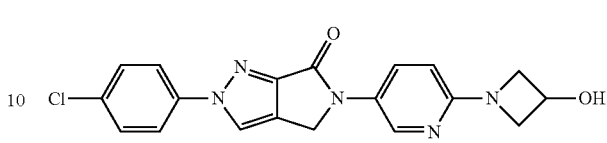

A mixture of Example 34A (20 mg, 0.061 mmol) and 3-hydroxyazetidine, HCl salt (27 mg, 0.47 mmol) in DMSO (1 mL) was irradiated in a microwave reactor at 140° C. for 30 min. The mixture was diluted with water (50 mL), flask cooled in a refrigerator overnight, filtered, washed with water, MeOH, and ether to yield 47 mg of a pale brown solid. The mixture was treated with 4N HCl/dioxane, sonicated for 5 min, and evaporated to yield the HCl salt. The residue was dissolved in minimum dmso-methanol-DMF mixture and purified by Preparative HPLC (PHENOMENEX® Luna Axia 5µ, C18 30×100 mm; 10 min gradient from 40% A: 60% B to 0% A:100% B (A=90% H$_2$O/10% MeOH+0.1% TFA); (B=90% MeOH/10% H$_2$O+0.1% TFA); detection at 220 nm) to yield Example 1, TFA (1.6 mg, 3.19 µmol, 5.3% yield) as a white solid. LC-MS, [M+H]$^+$=382.2. $^1$H NMR (CD$_3$OD, 400 MHz): δ 8.53 (d, J=2.6 Hz, 1H), 8.39 (s, 1H), 8.31 (dd, J=9.5, 2.0 Hz, 1H), 7.88 (d, J=9.2 Hz, 2H), 7.55 (d, J=9.2 Hz, 2H), 7.55 (d, J=9.2 Hz, 2H), 6.93 (d, J=9.7 Hz, 1H), 4.86 (s, 1H), 4.77-4.84 (m, 1H), 4.52 (m, 2H), 4.1 (dd, J=9.9, 4.2 Hz, 2H). HPLC-1: Rt 5.85 min, purity >99%. HPLC-2: Rt=4.82 min, purity >99%.

Example 55

(S)-2-(5-Chloropyridin-2-yl)-5-(6-(3-(methylamino)pyrrolidin-1-yl)pyridin-3-yl)-4,5-dihydropyrrolo[3,4-c]pyrazol-6(2H)-one

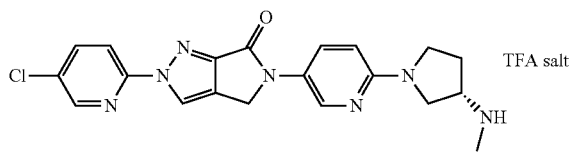 [SMILES: CN[C@H]1CCN(c2ccc(N3Cc4cn(-c5ccc(Cl)cn5)nc4C3=O)cn2)C1]

Example 55A (E)-Ethyl 2-(2-carbamoylhydrazono)propanoate

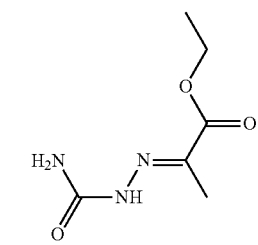

To a solution of semicarbazide hydrochloride (2.0 g, 17.9 mmol) in water (15 mL) was added ethyl pyruvate (2.1 g, 17.9 mmol) and sodium acetate (2.9 g, 35.9 mmol). The resulting mixture was stirred at RT overnight when a white solid precipitated out of solution. The solid was filtered, washed with 200 ml water and dried to yield. Example 55A (2.8 g, 90% yield). ¹H NMR (DMSO-d₆, 400 MHz): δ9.85 (s, 1 H), 6.47 (br. s, 2 H), 4.18 (q, J=7.1 Hz, 2 H), 1.99 (s, 3 H), 1.25 (t, J=7.1 Hz, 3 H).

Example 55B

Ethyl 4-formyl-1H-pyrazole-3-carboxylate

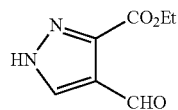

To dry DMF (15 mL) at 0° C. was added phosphorus oxychloride (14.6 g, 95 mmol) dropwise under Ar and the mixture stirred for 30 min at 0° C. Example 55A (2.8 g, 16 mmol) was added portion-wise at 0° C. The resulting orange solution was allowed to warm up to RT and stirred at 60° C. for 4 hours. After cooling to RT, the mixture was poured onto crushed ice. 3 N NaOH was added to adjust the pH to ~6. The mixture was heated at 60° C. for 5 min, and cooled to RT. After sitting at RT O/N, the solid was collected by filtration to yield Example 55B (1.5 g, 55% yield). LC-MS, [M+H]⁺= 169. ¹H NMR (DMSO-d₆, 400 MHz) δ 14.19 (br. s, 1 H), 10.26 (s, 1 H), 8.43 (br. s, 1 H), 4.37 (q, J=7.2 Hz, 2 H), 1.34 (t, J=7.2 Hz, 3 H).

Example 55C

Ethyl 1-(5-chloropyridin-2-yl)-4-formyl-1H-pyrazole-3-carboxylate

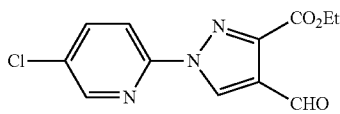

To a solution Example 55B (0.96 g, 5.7 mmol) in DMF (4 mL) was added potassium carbonate (2.10 g, 16.0 mmol), followed by 2-bromo-5-chloropyridine (1.00 g, 5.2 mmol). The mixture was stirred at 100° C. for 2 h. After cooling to rt, 300 mL CH₂Cl₂ was added. The solid was filtered. The filtrate was concentrated to yield a residue which was purified by flash chromatography (0 to 20% ethyl acetate:hexanes) to afford Example 55C (1.3 g, 90% yield). LC-MS, [M+H]⁺= 280. ¹H NMR (CDCl₃, 400 MHz) δ 10.46 (s, 1 H), 9.09 (s, 1 H), 8.44 (d, J=2.5 Hz, 1 H), 8.12 (d, J=8.8 Hz, 1 H), 7.87 (dd, J=8.8, 2.5 Hz, 1 H), 4.53 (q, J=7.2 Hz, 2 H), 1.48 (t, J=7.2 Hz, 3 H).

Example 55D

Ethyl 1-(5-chloropyridin-2-yl)-4-(hydroxymethyl)-1H-pyrazole-3-carboxylate

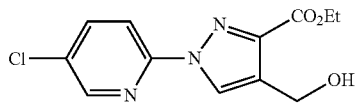 [SMILES: CCOC(=O)c1nn(-c2ccc(Cl)cn2)cc1CO]

To a solution of Example 55C (290 mg, 0.76 mmol) in THF (15 mL) at 0° C. was added NaBH₄ (14 mg, 0.38 mmol). The mixture was stirred at 0° C. for 1.5 h.

The reaction was quenched with 5 ml sat. aq. NaHCO₃ solution, and filtered. The filtrate was extracted with EtOAc. The organic layer was washed with brine, dried over anhydrous Na₂SO₄, and concentrated. The residue was purified by flash chromatography (5 to 50% ethyl acetate:hexanes) to afford Example 55D (150 mg, 70% yield). LC-MS, [M–H₂O+H]⁺=264. ¹H NMR (CDCl₃, 400 MHz) δ 8.51 (s, 1 H), 8.38 (d, J=2.5 Hz, 1 H), 8.06 (d, J=8.6 Hz, 1 H), 7.81 (dd, J=8.6, 2.5 Hz, 1 H), 4.77 (d, J=6.9 Hz, 2 H), 4.49 (q, J=7.2 Hz, 2 H), 3.48 (t, J=6.9 Hz, 1 H), 1.47 (t, J=7.2 Hz, 3 H).

Example 55E 1-(5-Chloropyridin-2-yl)-4-(hydroxymethyl)-1H-pyrazole-3-carboxylic acid

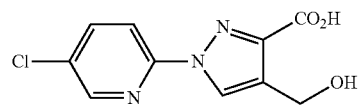 [SMILES: O=C(O)c1nn(-c2ccc(Cl)cn2)cc1CO]

A mixture of Example 55D (150 mg, 0.50 mmol) and NaOH (2 mL, 2.00 mmol, 1 N solution) in MeOH (10 mL) was stirred at RT for 2 h. After concentration, the mixture was acidified to pH 4-5. The solid was filtered to afford Example 55E (135 mg, 100% yield). LC-MS, [M–H₂O+H]⁺=236. ¹H NMR (DMSO-d₆, 400 MHz) δ 8.60 (d, J=2.5 Hz, 1 H), 8.51 (s, 1 H), 8.16 (dd, J=8.8, 2.5 Hz, 1 H), 7.98 (d, J=8.8 Hz, 1 H), 4.67 (s, 2 H).

Example 55F (S)-tert-Butyl 1-(5-(1-(5-chloropyridin-2-yl)-4-(hydroxymethyl)-1H-pyrazole-3-carboxamido)pyridin-2-yl)pyrrolidin-3-yl(methyl)carbamate

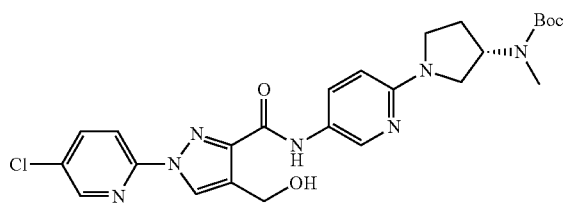 [SMILES: CN(C(=O)OC(C)(C)C)[C@H]1CCN(c2ccc(NC(=O)c3nn(-c4ccc(Cl)cn4)cc3CO)cn2)C1]

To a mixture of Example 55E (50 mg, 0.20 mmol) and (S)-tert-butyl 1-(5-aminopyridin-2-yl)pyrrolidin-3-yl(methyl)carbamate (58 mg, 0.20 mmol) in dichloromethane (10 mL) was added HOBT (36 mg, 0.24 mmol) and EDC (45 mg, 0.24 mmol). The resulting mixture was stirred at RT for 2 hours. The reaction was diluted with CH₂Cl₂ (30 ml) and washed with water (10 mL), followed by brine. The organic solution was dried over anhydrous Na₂SO₄ and concentrated to afford Example 55F (104 mg, 100% yield), which was carried on to the next step without purification. LC-MS, [M+H]⁺=528.

Example 55G (S)-tert-Butyl 1-(5-(4-(chloromethyl)-1-(5-chloropyridin-2-yl)-1H-pyrazole-3-carboxamido)pyridin-2-yl)pyrrolidin-3-yl(methyl)carbamate

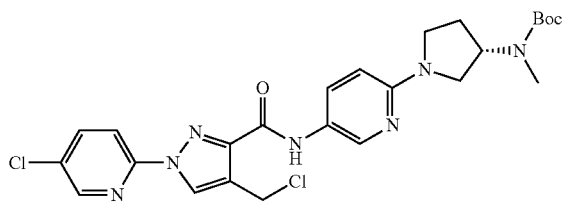 [SMILES: CN(C(=O)OC(C)(C)C)[C@H]1CCN(c2ccc(NC(=O)c3nn(-c4ccc(Cl)cn4)cc3CCl)cn2)C1]

To a solution of Example 55F (104 mg, 0.20 mmol) in DCM (5 mL) at RT under Ar was added N,N-diisopropylethylamine (76 mg, 0.60 mmol) and methanesulfonyl chloride (34 mg, 0.30 mmol). The resulting solution was stirred at RT for 4 h. The mixture was diluted with DCM, washed with sat. aq. NaHCO$_3$, brine, dried over anhydrous Na$_2$SO$_4$ and concentrated. The residue was purified by flash chromatography (5 to 100% ethyl acetate:hexanes) to afford Example 55G (58 mg, 54% yield). LC-MS, [M+H]$^+$=546.

Example 55H (S)-tert-Butyl 1-(5-(2-(5-chloropyridin-2-yl)-6-oxopyrrolo[3,4-c]pyrazol-5(2H,4H,6 H)-yl)pyridin-2-yl)pyrrolidin-3-yl(methyl)carbamate

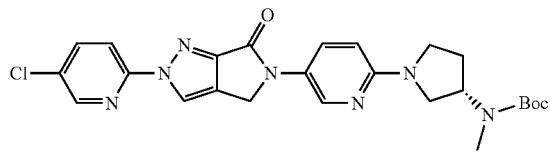 [SMILES: CN(C(=O)OC(C)(C)C)[C@H]1CCN(c2ccc(N3Cc4cn(-c5ccc(Cl)cn5)nc4C3=O)cn2)C1]

To a solution of Example 55G (58 mg, 0.11 mmol) in DMF (1 mL) was added potassium carbonate (70 mg, 0.51 mmol) was stirred at 95° C. for 2 h. After cooling to RT, 10 mL water was added. The solid was filtered and dried to yield Example 55H (55 mg, 100% yield). LC-MS, [M+H]$^+$=510.

Example 55

(S)-2-(5-Chloropyridin-2-yl)-5-(6-(3-(methylamino)pyrrolidin-1-yl)pyridin-3-yl)-4,5-dihydropyrrolo[3,4-c]pyrazol-6(2 H)-one

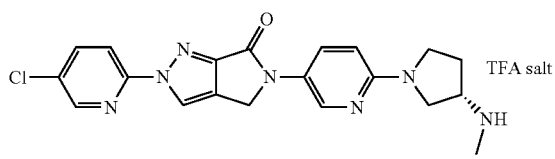 [SMILES: CN[C@H]1CCN(c2ccc(N3Cc4cn(-c5ccc(Cl)cn5)nc4C3=O)cn2)C1]

To a mixture of Example 55H (50 mg, 0.10 mmol) in DCM (2 mL) was added TFA (296 mg, 2.60 mmol). The reaction was stirred at RT overnight. The mixture was concentrated. The residue was purified by prep. HPLC (20~100% MeOH: H$_2$O with 0.1% TFA, column: PHENOMENEX® Luna Axia 5μ 30×100) to afford Example 55 (37 mg, 57% yield). LC-MS, [M+H]$^+$=410. $^1$H NMR (DMSO-d$_6$, 400 MHz) δ 8.75 (s, 1 H), 8.63 (d, J=2.5 Hz, 1 H), 8.49 (d, J=2.5 Hz, 1 H), 8.19 (dd, J=8.8, 2.5 Hz, 1 H), 8.09 (dd, J=9.2, 2.5 Hz, 1 H), 8.05 (d, J=8.8 Hz, 1 H), 6.77 (d, J=9.2 Hz, 1 H), 4.93 (s, 2 H), 3.86-4.00 (m, 1 H), 3.73-3.85 (m, 1 H), 3.56-3.72 (m, 2 H), 3.44-3.57 (m, 1 H), 2.68 (t, J=5.1 Hz, 3 H), 2.41 (m, 1 H), 2.16-2.30 (m, 1 H). HPLC-1: Rt 4.6 min, purity=98%; HPLC-2: Rt 4.1 min, purity=98%.

Example 56

2-(5-Chloropyridin-2-yl)-5-(4-(2-hydroxy-2-methylpropoxy)-3-methoxyphenyl)-4,5-dihydropyrrolo[3,4-c]pyrazol-6(2H)-one

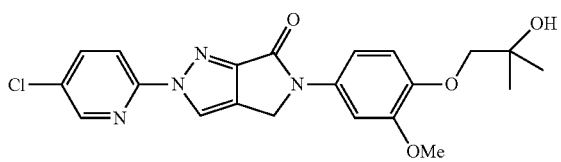 [SMILES: COc1cc(N2Cc3cn(-c4ccc(Cl)cn4)nc3C2=O)ccc1OCC(C)(C)O]

Example 56 was prepared using a procedure analogous to Example 55 except that (S)-tert-butyl 1-(5-aminopridin-2-yl)pyrrolidin-3-yl(methyl)carbamate was replaced by 3-methoxy-4-(2-methyl-2-((2-(trimethylsilyl)ethoxy)methoxy)propoxy)aniline. LC-MS, [M+H]$^+$=429. $^1$H NMR (CDCl$_3$, 400 MHz) δ 8.55 (s, 1 H), 8.39 (d, J=2.5 Hz, 1 H), 8.11 (d, J=8.8 Hz, 1 H), 7.83 (dd, J=8.8, 2.5 Hz, 1 H), 7.67 (d, J=2.5 Hz, 1 H), 7.03 (dd, J 8.6, 2.5 Hz, 1 H), 6.94 (d, J=8.6 Hz, 1 H), 4.81 (s, 2 H), 3.92 (s, 3 H), 3.84 (s, 2 H), 2.76 (s, 1 H), 1.35 (s, 6 H). HPLC-1: Rt 7.4 min, purity=98%; HPLC-2: Rt 8.5 min, purity=98%.

Example 57

(R)-2-(5-Chloropridin-2-yl)-5-(4-(2-cyclopropyl-2-hydroxyethoxy)-3-methoxyphenyl)-4,5-dihydropyrrolo[3,4-c]pyrazol-6(2H)-one

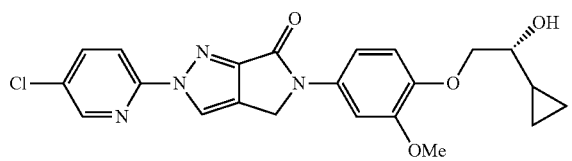 [SMILES: COc1cc(N2Cc3cn(-c4ccc(Cl)cn4)nc3C2=O)ccc1OC[C@H](O)C1CC1]

Example 57 was prepared using a procedure analogous to Example 55 except that (S)-tert-butyl 1-(5-aminopyridin-2-yl)pyrrolidin-3-yl(methyl)carbamate was replaced by (R)-4-(2-(tert-butyldimethylsilyloxy)-2-cyclopropylethoxy)-3-methoxyaniline. LC-MS, [M+H]$^+$=441. $^1$H NMR (CDCl$_3$, 400 MHz) δ 8.55 (s, 1 H), 8.39 (d, J=2.5 Hz, 1 H), 8.12 (d, J=8.8 Hz, 1 H), 7.84 (dd, J=8.8, 2.5 Hz, 1 H), 7.69 (d, J=2.3 Hz, 1 H), 7.04 (dd, J=8.6, 2.3 Hz, 1 H), 6.98 (d, J=8.6 Hz, 1 H), 4.81 (s, 2 H), 4.19 (dd, J=9.9, 2.8 Hz, 1 H), 3.99 (dd, J=9.9, 8.3 Hz, 1 H), 3.92 (s, 3 H), 3.33 (td, J=8.3, 2.8 Hz, 1 H), 0.92-1.00

Example 58

2-(4-Chlorophenyl)-5-(6-((3R,4R)-3-hydroxy-4-(methylamino)pyrrolidin-1-yl)pyridin-3-yl)-4,5-dihydropyrrolo[3,4-c]pyrazol-6(2H)-one

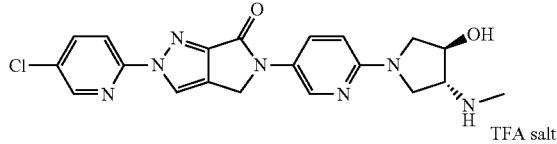 [SMILES: CN[C@@H]1CN(c2ccc(N3Cc4cn(-c5ccc(Cl)cn5)nc4C3=O)cn2)C[C@H]1O]

TFA salt

Example 58A

Benzyl 6-oxa-3-azabicyclo[3.1.0]hexane-3-carboxylate

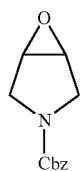

A solution of benzyl 2,5-dihydro-1H-pyrrole-1-carboxylate (2 g, 9.8 mmol) in dichloromethane (50 mL) was cooled to 0° C. and m-CPBA (2.7 g, 11.8 mmol) was added over a period of 20 min. The reaction was stirred at room temperature for 2 days while a solid precipitated out of the solution. The solid was filtered off and the filtrate was successively washed with sat. aq. NaHSO$_3$, 5% aq. K$_2$CO$_3$, and brine, dried over anhydrous Na$_2$SO$_4$ and then concentrated in vacuo. The residue was purified by flash chromatography (5 to 60% ethyl acetate:hexanes) to afford Example 58A (1.5 g, 70% yield). LC-MS, [M+H]$^+$=220. $^1$H NMR (CDCl$_3$, 400 MHz) δ 7.28-7.41 (m, 5 H), 5.12 (2d, J=3.5 Hz, 2 H), 3.81-3.93 (m, 2 H), 3.66-3.71 (m, 2 H), 3.39 (m, 2 H).

Example 58B (3R,4R)-Benzyl 3-hydroxy-4-(methylamino)pyrrolidine-1-carboxylate

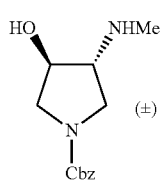

A mixture of Example 58A (1.5 g, 6.8 mmol) and 40% w/w methylamine (13.5 g, 174 mmol) in water solution was stirred at room temperature O/N. The solvent was evaporated to afford Example 58B as an oil (1.7 g, 100% yield), which was carried on to the next step without purification. LC-MS, [M+H]$^+$=251.

Example 58C (3R,4R)-Benzyl 3-(tert-butoxycarbonyl(methyl)amino)-4-hydroxypyrrolidine-1-carboxylate

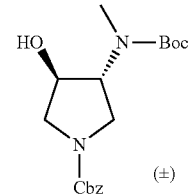

Di-tert-butyl dicarbonate (2.2 g, 10.2 mmol) was added to a solution of Example 58B (1.7 g, 6.8 mmol) in methanol (30 mL) at 0° C. and the reaction mixture was stirred at room temperature O/N. After removing the solvent, the residue was purified by flash chromatography (5 to 50% ethyl acetate:hexanes) to afford Example 58C (2.4 g, 100% yield). LC-MS, [M+H]$^+$=351. $^1$H NMR (CDCl$_3$, 400 MHz) δ 7.30-7.43 (m, 5 H), 5.14 (s, 2 H), 4.26-4.47 (m, 2 H), 3.66-3.86 (m, 2 H), 3.23-3.51 (m, 2 H), 2.79 (s, 3 H), 1.64 (br. s, 1 H), 1.47 (s, 9 H).

Example 58D tert-Butyl (3R,4R)-4-hydroxypyrrolidin-3-yl(methyl)carbamate

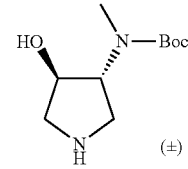

A mixture of Example 58C (2.36 g, 6.73 mmol) and Pd/C (0.36 g, 0.34 mmol) in methanol (20 mL) was purged with N$_2$, and then charged with a H$_2$ balloon. The reaction was stirred at room temperature for 2 h. The mixture was filtered through CELITE® and the filtrate concentrated to yield Example 58D (1.46 g, 100% yield). $^1$H NMR (CDCl$_3$, 400 MHz) δ 4.23-4.29 (m, 1 H), 4.15 (td, J=7.7, 4.0 Hz, 1 H), 3.29 (dd, J=12.0, 8.2 Hz, 1 H), 3.13 (dd, J=12.0, 6.2 Hz, 1 H), 2.84-2.94 (m, 2 H), 2.83 (s, 3 H), 1.47 (s, 9 H).

Example 58E tert-Butyl (3R,4R)-4-hydroxy-1-(5-nitropridin-2-yl)pyrrolidin-3-yl(methyl)carbamate

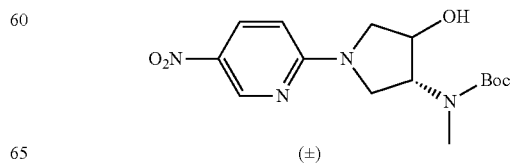

A microwave vial containing Example 58D (400 mg, 1.8 mmol) and 2-chloro-5-nitropyridine (293 mg, 1.8 mmol) in 2-propanol (6 mL) was heated at 150° C. in a microwave reactor for 30 min. After removing the solvent, the residue was purified by flash chromatography (5 to 60% ethyl acetate: hexanes) to afford Example 58E (393 mg, 63% yield). LC-MS, [M+H]⁺=339. ¹H NMR (CDCl₃, 400 MHz) δ 9.07 (d, J=2.5 Hz, 1 H), 8.24 (dd, J=9.3, 2.5 Hz, 1 H), 6.35 (d, J=9.3 Hz, 1 H), 4.46-4.60 (m, 2 H), 3.95 (br. s, 2 H), 3.63 (br. s, 1 H), 3.49 (br. s, 1 H), 2.84 (s, 3 H), 1.48 (s, 9 H).

Example 58F tert-Butyl (3R,4R)-4-(tert-butyldimethylsilyloxy)-1-(5-nitropyridin-2-yl)pyrrolidin-3-yl(methyl)carbamate

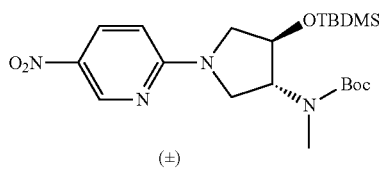 [SMILES: CN(C(=O)OC(C)(C)C)[C@@H]1CN(c2ccc([N+](=O)[O-])cn2)C[C@H]1O[Si](C)(C)C(C)(C)C]

(±)

To a solution of Example 58E (370 mg, 1.09 mmol) in DCM (15 mL) at 0° C. was added 2,6-lutidine (234 mg, 2.19 mmol) and tert-butyldimethylsilyl trifluoromethanesulfonate (434 mg, 1.64 mmol). The resulting mixture was stirred at this temperature for 10 min and then stirred at RT for 1/2 h. The reaction was quenched with sat. aq. NaHCO₃. The organic layer was separated and washed with brine, dried over anhydrous Na₂SO₄, and concentrated. The residue was purified by flash chromatography (0 to 20% ethyl acetate:hexanes) to afford Example 58F (295 mg, 60% yield). LC-MS, [M+H]⁺=453.

Example 58G tert-Butyl (3R,4R)-1-(5-aminopyridin-2-yl)-4-(tert-butyldimethylsilyloxy)pyrrolidin-3-yl(methyl)carbamate

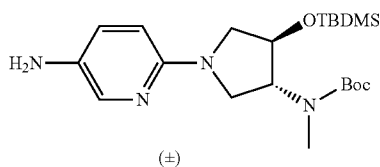

(±)

A mixture of Example 58F (295 mg, 0.65 mmol) and Pd/C (35 mg, 0.03 mmol) in MeOH (10 mL) and ethyl acetate (15 mL) was purged with N₂, and then charged with a H₂ balloon. The reaction was stirred at room temperature for 2 h. The mixture was filtered through CELITE® and the filtrate concentrated to yield Example 58G (275 mg, 100% yield). LC-MS, [M+H]⁺=423.

Example 58

2-(4-Chlorophenyl)-5-(6-((3R,4R)-3-hydroxy-4-(methylamino)pyrrolidin-1-yl)pyridin-3-yl)-4,5-dihydropyrrolo[3,4-c]pyrazol-6(2H)-one

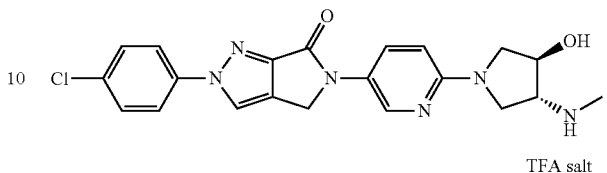

TFA salt

Example 58 was prepared using a procedure analogous to Example 55 except that Example 55E was replaced by 1-(4-chlorophenyl)-4-(hydroxymethyl)-1H-pyrazole-3-carboxylic acid and (S)-tert-butyl 1-(5-aminopyridin-2-yl)pyrrolidin-3-yl(methyl)carbamate was replaced by Example 58G. LC-MS, [M+H]⁺=425. ¹H NMR (CD₃OD, 400 MHz) δ 8.56 (d, J=2.5 Hz, 1 H), 8.36 (s, 1 H), 8.17 (dd, J=9.3, 2.5 Hz, 1 H), 7.87 (d, J=8.8 Hz, 2 H), 7.55 (d, J=8.8 Hz, 2 H), 6.89 (d, J=9.3 Hz, 1 H), 4.92 (s, 2 H), 4.63 (br. s, 1 H), 4.07 (dd, J=10.9, 6.1 Hz, 1 H), 3.98 (dd, J=10.9, 6.3 Hz, 1 H), 3.72-3.82 (m, 2 H), 3.49 (dd, J=10.9, 4.9 Hz, 1 H), 2.88 (s, 3 H). HPLC-1: Rt 4.9 min, purity=98%; HPLC-2: Rt 4.3 min, purity=98%.

Example 59

4-(2-((1-(5-(2-(4-Chlorophenyl)-6-oxopyrrolo[3,4-c]pyrazol-5(2H,4H,6 H)-yl)pyridin-2-yl)pyrrolidin-3-yl)(methyl)amino)ethyl)tetrahydro-2H-pyran-4-carboxylic acid,

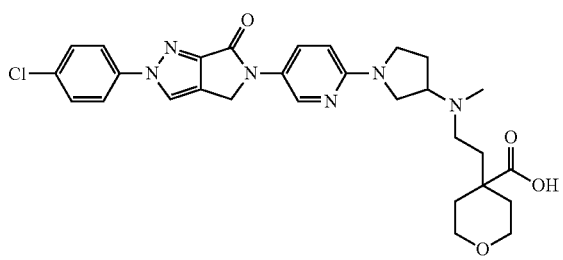

2TFA

Example 59A tert-Butyl 4-(2-((1-(5-bromopyridin-2-yl)pyrrolidin-3-yl)(methyl)amino)ethyl)tetrahydro-2H-pyran-4-carboxylate

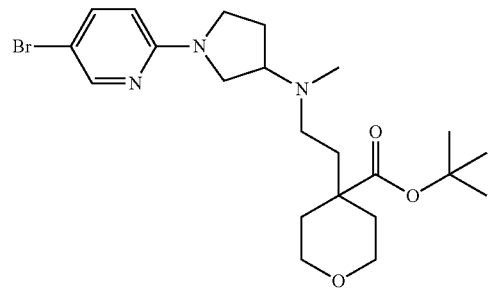 [SMILES: CN(CCC1(C(=O)OC(C)(C)C)CCOCC1)C1CCN(c2ccc(Br)cn2)C1]

Example 59A was prepared using a procedure adapted from WO 2004/043958.

Example 59

4-(2-((1-(5-(2-(4-Chlorophenyl)-6-oxopyrrolo[3,4-c]pyrazol-5(2H,4H,6H)-yl)pyridin-2-yl)pyrrolidin-3-yl)(methyl)amino)ethyl)tetrahydro-2H-pyran-4-carboxylic acid, 2TFA

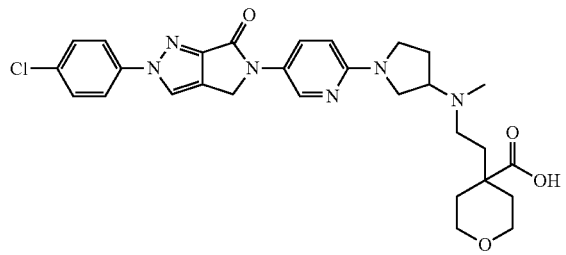 [SMILES: CN(CCC1(C(=O)O)CCOCC1)C1CCN(c2ccc(N3Cc4cn(-c5ccc(Cl)cc5)nc4C3=O)cn2)C1]

Example 59 was prepared using a procedure analogous to one used to prepare Example 11 above except that Example 11A was replaced by Example 59A and the coupled product deprotected in the presence of TFA to afford Example 59. LC-MS, [M+H]=565. $^1$H NMR (400 MHz, CD$_3$OD) δ 8.52 (d, J=2.51 Hz, 1H), 8.05-8.41 (m, 2H), 7.73 (d, J=8.78 Hz, 2H), 7.41 (d, J=8.78 Hz, 2H), 7.00 (d, J=9.79 Hz, 1H), 4.79 (s, 2H), 4.11-4.48 (m, J=7.65, 7.65, 7.53, 7.28 Hz, 1H), 4.03 (dd, J=10.92, 7.65 Hz, H), 3.66-3.93 (m, 4H), 3.51-3.66 (m, 1H), 3.34-3.51 (m, 2H), 3.15-3.29 (m, 2H), 2.90 (s, 3H), 2.45-2.76 (m, 1H), 2.36 (dq, J=13.02, 8.79 Hz, 1H), 1.61-2.20 (m, 3H), 0.97-1.80 (m, 2H).

Example 60

1-(2-((1-(5-(2-(4-Chlorophenyl)-6-oxopyrrolo [3,4-c]pyrazol-5(2H,4H,6H)-yl)pyridin-2-yl)pyrrolidin-3-yl)(methyl)amino)ethyl)cyclohexanecarboxylic acid, 2HCl

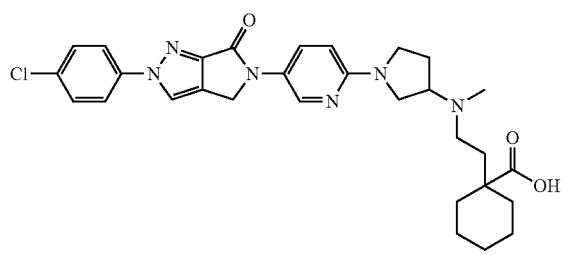 [SMILES: CN(CCC1(C(=O)O)CCCCC1)C1CCN(c2ccc(N3Cc4cn(-c5ccc(Cl)cc5)nc4C3=O)cn2)C1]

Example 60A tert-Butyl 1-(2-((1-(5-bromopyridin-2-yl)pyrrolidin-3-yl)(methyl)amino)ethyl)cyclohexanecarboxylate

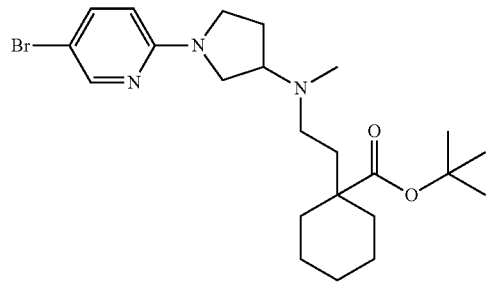 [SMILES: CN(CCC1(C(=O)OC(C)(C)C)CCCCC1)C1CCN(c2ccc(Br)cn2)C1]

Example 60A was prepared using a procedure adapted from *J. Org. Chem.*, 72(25):9648-9655 (2007).

Example 60

1-(2-((1-(5-(2-(4-Chlorophenyl)-6-oxopyrrolo[3,4-c]pyrazol-5(2H,4H,6H)-yl)pyridin-2-yl)pyrrolidin-3-yl)(methyl)amino)ethyl)cyclohexanecarboxylic acid, 2 HCl

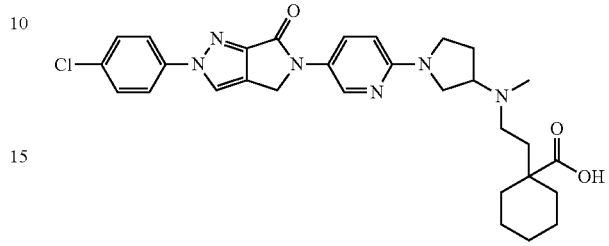

Example 60 was prepared using a procedure analogous to one used to prepare Example 11 above except that Example 11A was replaced by Example 60A and the coupled product deprotected in the presence of TFA to afford the crude TFA salt. This TFA salt was redissolved in methylene chloride, and 1N HCl in ether (1 mL) added to it. The precipitated solid was isolated by filtration and dried under vacuum to afford a brown solid which was triturated with MeOH, and then EtOH, to afford Example 60, HCl salt as an off-white solid. LC-MS, [M+H]$^+$=563. $^1$H NMR (400 MHz, DMSO-d$_6$) δ 10.85 (br. s., 1H), 8.71 (s, 1H), 8.50 (d, J=2.51 Hz, 1H), 8.13 (d, J=8.03 Hz, 1H), 7.98 (d, J=9.04 Hz, 2H), 7.65 (d, J=9.03 Hz, 2H), 6.84 (br. s., 1H), 4.94 (s, 2H), 4.14 (dd, J=15.43, 7.65 Hz, 2H), 3.53-3.83 (m, 2H), 3.25-3.61 (m, 1H), 2.92-3.29 (m, 2H), 2.81 (dd, J=7.40, 4.64 Hz, 3H), 2.30-2.56 (m, 2H), 1.68-2.17 (m, 4H), 1.43-1.77 (m, 3H), 1.12-1.43 (m, 5H).

Biological Evaluation

Radioligand Binding Assay for Assessment of MCHR1 Activity

Membranes from stably transfected HEK-293 cells expressing a mutated (E4Q, A5T) hMCHR1 receptor were prepared by dounce homogenization and differential centrifugation. Binding experiments were carried out with 0.5-1.0 ug of membrane protein incubated in a total of 0.2 ml in 25 mM HEPES (pH 7.4) with 10 mM MgCl$_2$, 2 mM EGTA, and 0.1% BSA (Binding Buffer) for 90 min. For competition binding assays, reactions were carried out in the presence of with 0.06-0.1 nM [Phe[13], [$^{125}$I]Tyr[19]]-MCH and increasing concentrations of unlabeled test molecules. Reactions were terminated by rapid vacuum filtration over 96 well-GFC UNIFILTER® plates pre-coated with 0.075 ml binding buffer containing 1% BSA, and washed 3 times with 0.4 ml of Phospho-buffered Saline (pH 7.4) containing 0.01% TX-100. Filters were dried, 0.05 ml microscint 20 was added to each well and radioactivity was subsequently quantified by scintillation counting on a TOPCOUNT® microplate scintillation counter (Packard). Inhibitory constants were determined by nonlinear least squares analysis using a four parameter logistic equation.

| Example | MCHR1 Human Binding (Ki, nM) |
|---|---|
| 1 | 41.4 |
| 2 | 333.6 |
| 3 | 106.5 |
| 4 | 41.1 |
| 5 | 13.7 |
| 6 | 13.2 |
| 7 | 49.4 |
| 8 | 12.5 |
| 9 | 8.6 |
| 10 | 2.7 |
| 11 | 81.0 |
| 12 | 2.3 |
| 13 | 34.3 |
| 14 | 112.6 |
| 14B | 304.4 |
| 15 | 0.7 |
| 16 | 2.5 |
| 16G | 3.6 |
| 17 | 0.9 |
| 18 | 0.7 |
| 19 | 1.3 |
| 19A | 184.0 |
| 20 | 0.9 |
| 20A | 784.4 |
| 24 | 2.7 |
| 28 | 0.9 |
| 29 | 17.1 |
| 42 | 0.5 |
| 47 | 32.7 |

It should be understood that while this application has been described herein in terms of specific embodiments set forth in detail, such embodiments are presented by way of illustration of the general principles of the application, and the application is not necessarily limited thereto. Certain modifications and variations in any given material, process step or chemical formula will be readily apparent to those skilled in the art without departing from the true spirit and scope of the present application, and all such modifications and variations should be considered within the scope of the claims that follow.

What is claimed is:

1. A compound of Formula I

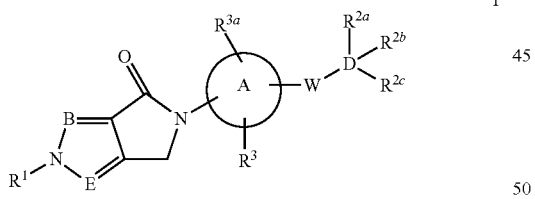

or a pharmaceutically acceptable salt or a stereoisomer thereof:
wherein

is a monocyclic aryl or monocyclic heteroaryl;

W is a direct bond, —O—, or —N($R^6$)—, provided that if W is a direct bond, D must be a cyclic amine that is attached to A via the nitrogen atom of said cyclic amine;

D is a direct bond, substituted or unsubstituted $C_1$ to $C_4$ alkyl, substituted or unsubstituted $C_3$ to $C_7$ cycloalkyl, cycloalkylalkyl, or a 4 to 6 membered cyclic amine;

B and E are independently N or CH provided that both are not CH;

$R^1$ is substituted or unsubstituted phenyl, substituted or unsubstituted pyridyl, or substituted or unsubstituted thienyl;

$R^{2a}$, $R^{2b}$, and $R^{2c}$ are independently selected from the group consisting of hydrogen, halo, cyano, hydroxyl, —$NR^5R^{5a}$, —$OSO_2R^{34}$, —$NR^5CO_2R^{21}$, —$NR^5COR^{21}$, —$CO_2R^{35}$, substituted or unsubstituted $C_1$ to $C_4$ alkyl, substituted or unsubstituted $C_3$ to $C_7$ cycloalkyl, a substituted or unsubstituted 4 to 6 membered cyclic amine wherein said cyclic amine is optionally substituted with —OH; carbonylamino, alkoxycarbonylamino; a prodrug moiety selected from amino acid esters or phosphoric acid esters wherein said amino acid ester is of the formula —OC(O)CH($NH_2$)$R^{31}$; or any two of $R^{2a}$, $R^{2b}$, or $R^{2c}$, may be taken together to form a cycloalkyl or a cyclic amine; provided that if D is a direct bond, $R^{2a}$, $R^{2b}$ and $R^{2c}$ are each independently H, alkyl, or cycloalkyl;

$R^3$ and $R^{3a}$ are each independently selected from the group consisting of hydrogen, hydroxyl, lower alkoxy, halo, CN, substituted or unsubstituted $C_1$ to $C_4$ alkyl, perfluoroalkyl, substituted or unsubstituted $C_3$ to $C_7$ cycloalkyl, and cycloalkoxy; or $R^3$ and D or $R^{3a}$ and D may optionally be taken together with the atoms to which they are attached to form a 5- to 7membered ring;

$R^5$ and $R^5$a are the same or different and are independently selected from the group consisting of hydrogen, substituted or unsubstituted lower alkyl, hydroxyalkyl, hydroxyalkylcycloalkyl, substituted or unsubstituted heterocycloalkyl, acyl, alkoxycarbonyl, carboxyalkyl, substituted or unsubstituted cycloalkyl, substituted or unsubstituted cycloalkylalkyl, and substituted or unsubstituted cycloalkoxyalkyl wherein the $R^5$ and $R^{5a}$ groups and the N atom to which they are attached may form a ring;

$R^{31}$ is H or $C_1$ to $C_4$ alkyl;
$R^{21}$ and $R^{34}$ are alkyl;
$R^{35}$ is H or alkyl; and
$R^6$ is selected from the group consisting of H, $C_1$ to $C_4$ alkyl and $C_3$ to $C_7$ cycloalkyl, provided that
(1) when $R^1$ is

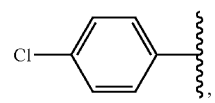

B is CH, E is N,

is

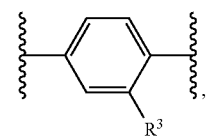

is $R^3$ is $OCH_3$, and W is O, then

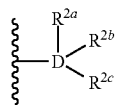

is other than $CH_3$;
(2) when $R^1$ is

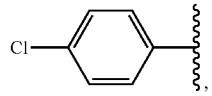

B is N, E is CH, is

$R^3$ is H, and W is O, then

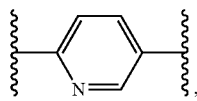

is other than

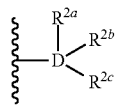

2. The compound according to claim 1 wherein
W is a direct bond;
D is a cyclic amine selected from the group consisting of pyrrolidinyl, piperidinyl, and azetidinyl; and
$R^{2a}$, $R^{2b}$, and $R^{2c}$ are each independently, H, —OH, halo, —N($R^5 R^{5a}$),—$NR^5CO_2R^{21}$, —$NR^5COR^{21}$, halo, pyrrolidinyl, azetidinyl, or —OC(O)CH(NH_2)R^{31}, or $R^{2a}$ and $R^{2b}$ are taken together to form a cyclic amine optionally substituted with F, hydroxyalkyl, —C(O)alkyl, or benzyl; and
$R^5$ and $R^{5a}$ are independently selected from the group consisting of H, $C_1$ to $C_4$ alkyl, hydroxyalkyl, and cycloalkoxyalkyl.

3. The compound according to claim 1 wherein W is O and D is methyl, ethyl, or propyl and $R^{2a}$, $R^{2b}$, and $R^{2c}$ are, independently, H, —OH, —OC(O)C(NH_2)R^{31}, hydroxyalkyl, cyclopropyl, pyrrolidinyl, —$OSO_2R^{34}$, —$CO_2H$, or —OP(O)(OH)(OH), or $R^{2a}$ and $R^{2b}$ are joined together to form a cycloalkyl substituted with halo or hydroxyl; or D is a direct bond and $R^{2a}$, $R^{2b}$, and $R^{2c}$ are each H, alkyl, or cycloalkyl.

4. The compound according to claim 1 wherein

is phenyl, pyridinyl, or pyrimidinyl.

5. The compound according claim 1 wherein

is phenyl, pyridinyl, or pyrimidinyl; $R^1$ is phenyl or pyridyl substituted with Cl; $R^3$ and $R^{3a}$ are H or $C_1$ to $C_4$ alkyl, or methoxy; W is O or a bond; D is a bond, $C_1$ to $C_4$ alkyl, pyrrolidinyl, piperidinyl, or azetidinyl;
and $R^{2a}$, $R^{2b}$, and $R^{2c}$a are independently H, OH, alkyl, cycloalkyl, —$OSO_2R^{34}$ wherein $R^{34}$ is alkyl; —OC(O)CH(NH_2)R^{31}; —$NR^5R^{5a}$; —$NR^5CO_2R^{21}$; —$NR^5COR^{21}$; halo; or —OP(O)(OH)_2, or any two of $R^{2a}$, $R^{2b}$, and $R^c$ join together to form a cyclic amine or a cycloalkyl.

6. A compound according to claim 1 selected from the group consisting of the following, or a stereoisomer or a pharmaceutically acceptable salt thereof:

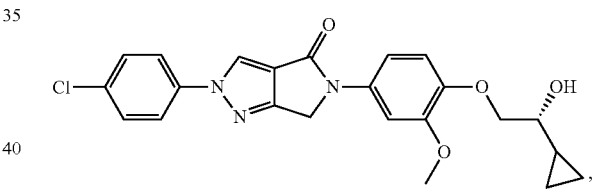

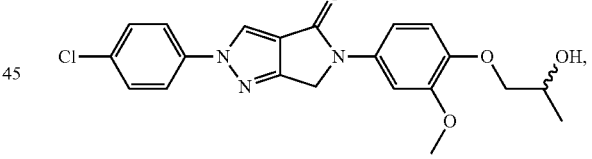

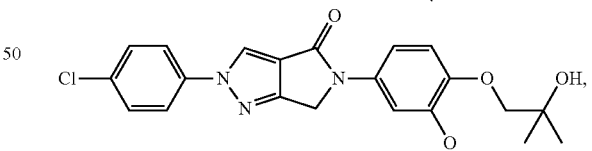

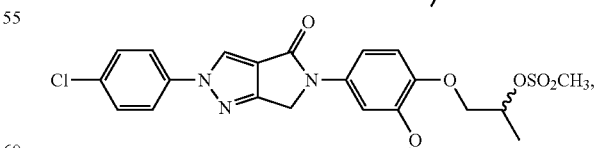

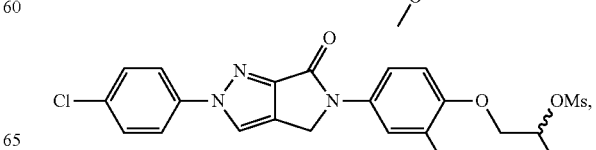

-continued
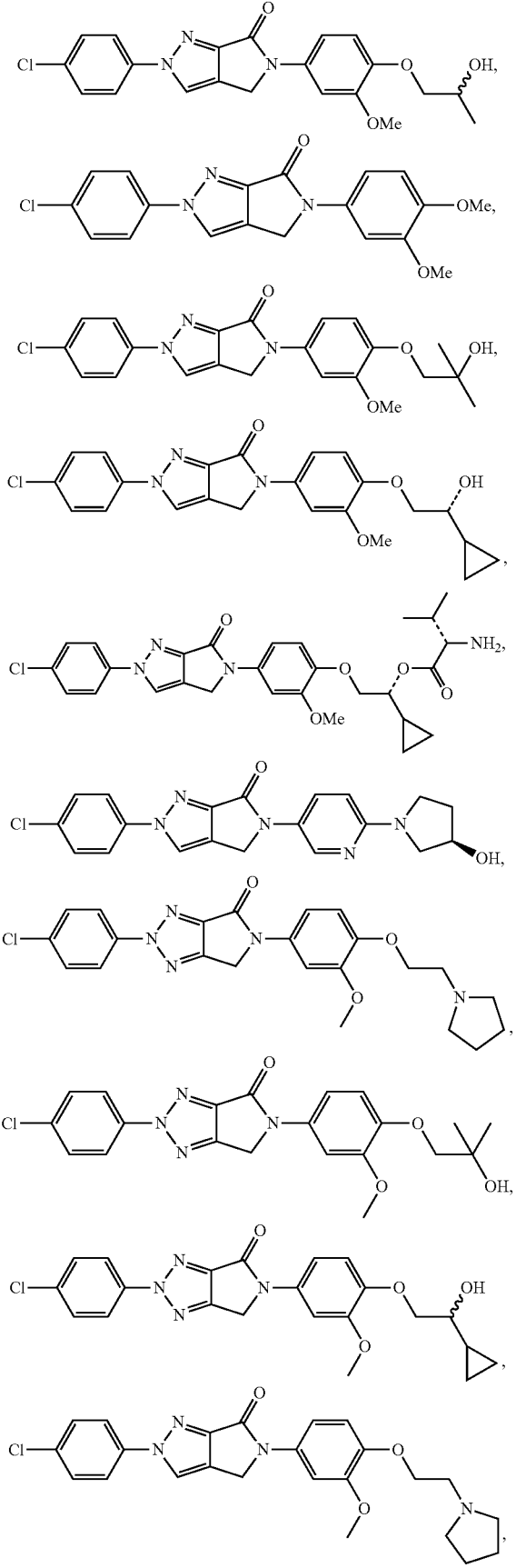
-continued
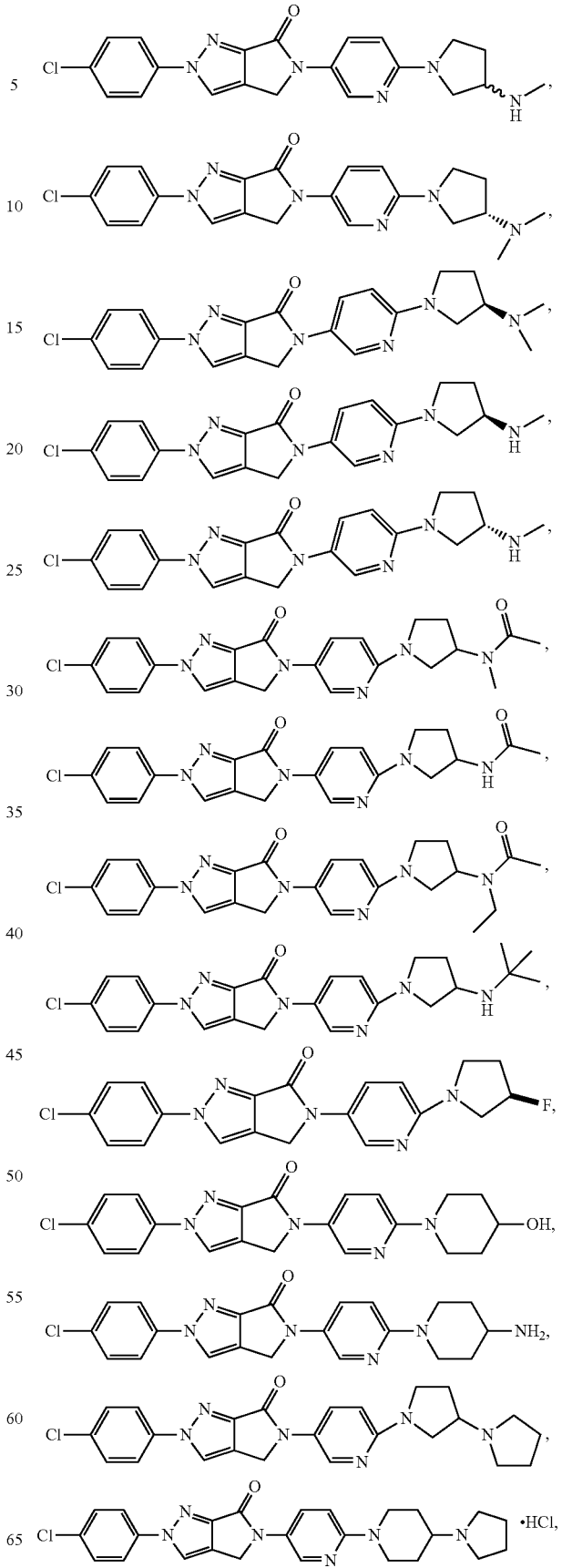

-continued
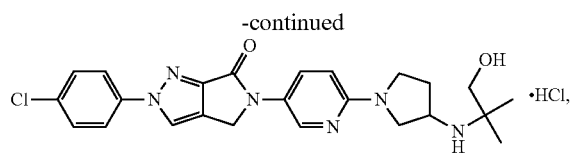
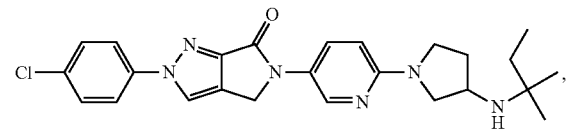
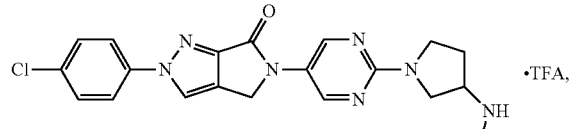 •TFA,
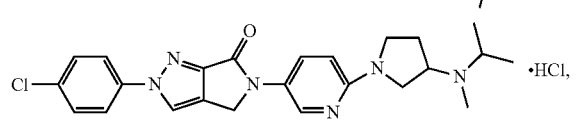 •HCl,
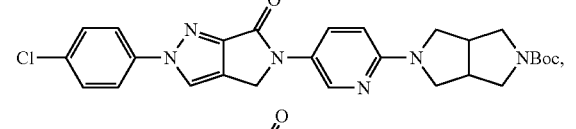
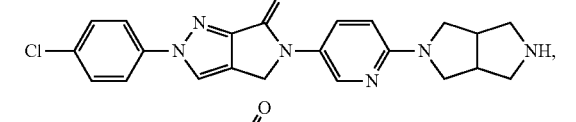
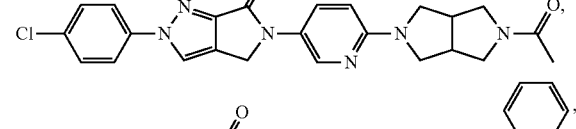
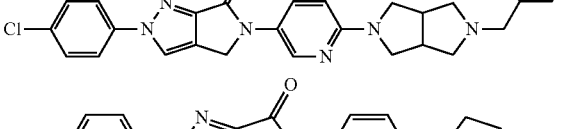
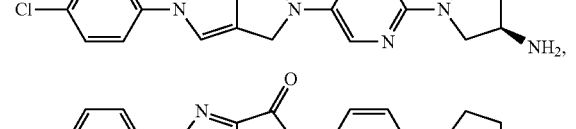
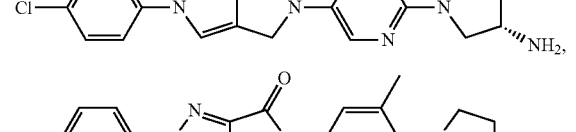
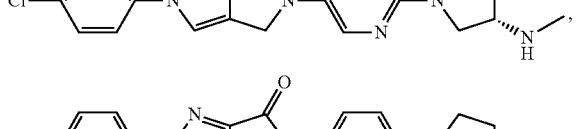
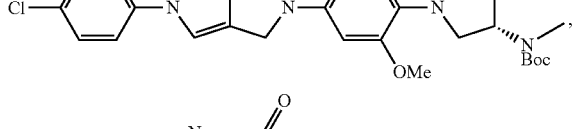
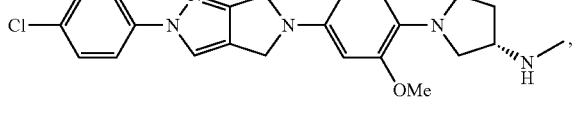
-continued
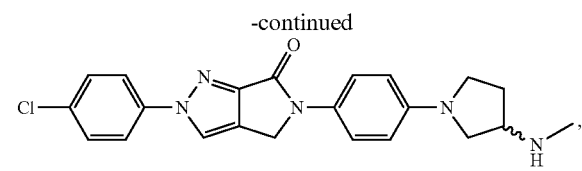
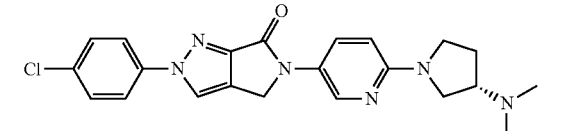
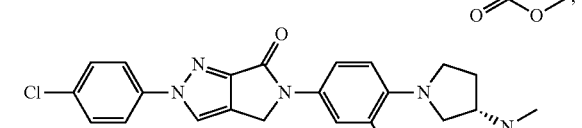
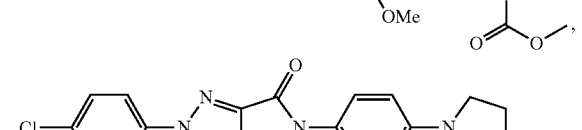
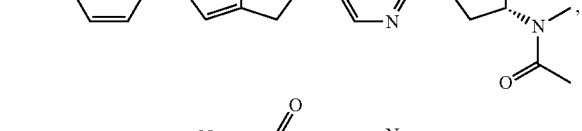
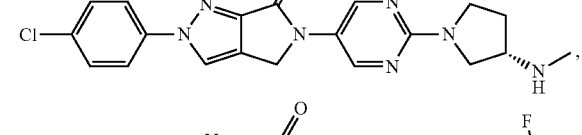
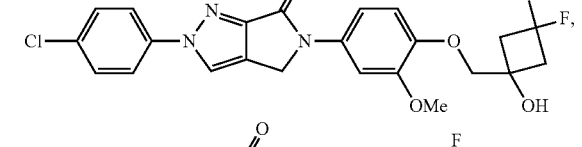
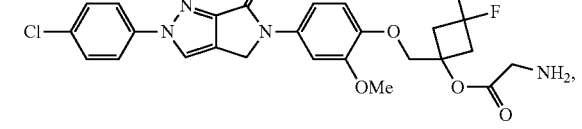
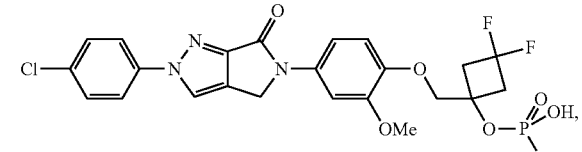
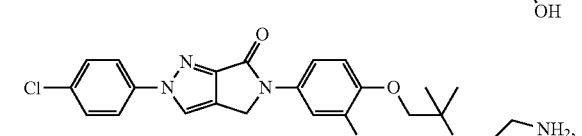
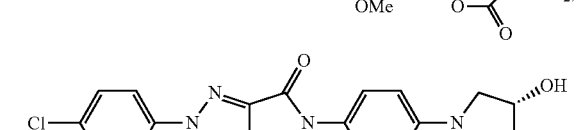
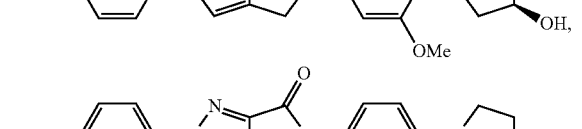
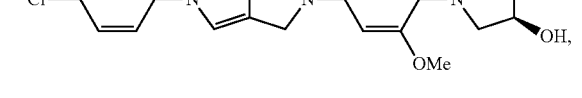

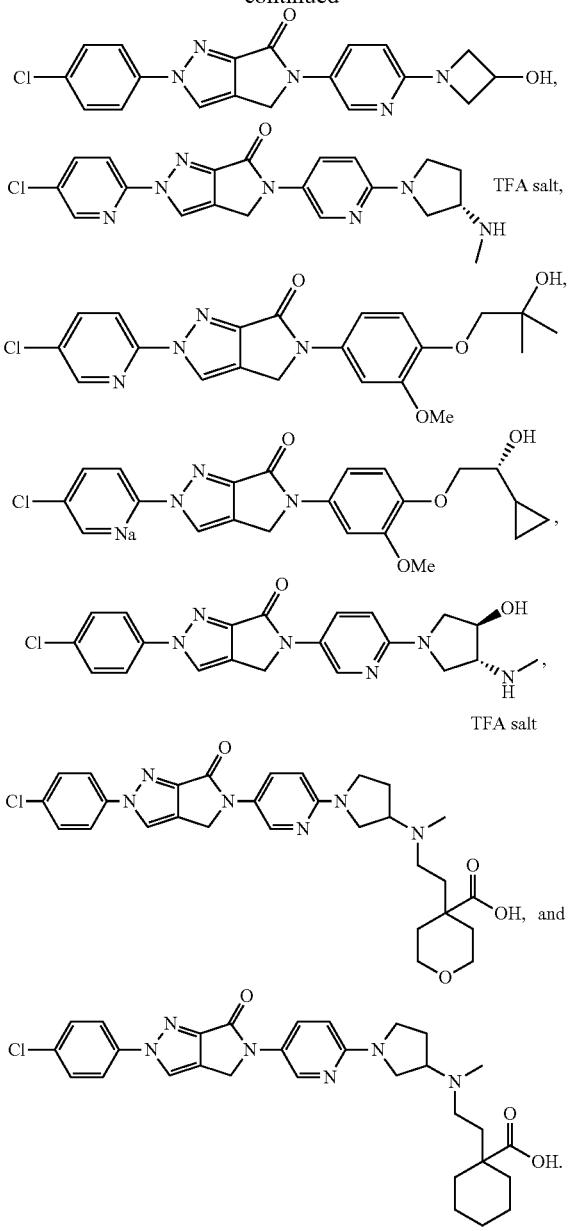

7. A pharmaceutical composition comprising at least one compound according to claim 1 and a pharmaceutically acceptable carrier.

8. The pharmaceutical composition according to claim 7 comprising at least one additional antiobesity agent.

9. The pharmaceutical composition according to claim 7 comprising at least one additional antidiabetic agent.

10. A method for treating obesity comprising administering to a patient in need of such treatment a therapeutically effective amount of a compound according to claim 1.

11. A method for treating type II diabetes comprising administering to a patient in need of such treatment a therapeutically effective amount of a compound according to claim 1.

12. A pharmaceutical composition comprising at least one compound according to claim 2 and a pharmaceutically acceptable carrier.

13. A pharmaceutical composition comprising at least one compound according to claim 3 and a pharmaceutically acceptable carrier.

14. A pharmaceutical composition comprising at least one compound according to claim 4 and a pharmaceutically acceptable carrier.

15. A pharmaceutical composition comprising at least one compound according to claim 5 and a pharmaceutically acceptable carrier.

16. A pharmaceutical composition comprising at least one compound according to claim 6 and a pharmaceutically acceptable carrier.

17. The pharmaceutical composition according to claim 16 comprising at least one additional antiobesity agent.

18. The pharmaceutical composition according to claim 16 comprising at least one additional antidiabetic agent.

19. A method for treating obesity comprising administering to a patient in need of such treatment a therapeutically effective amount of a compound according to claim 6.

20. A method for treating type II diabetes comprising administering to a patient in need of such treatment a therapeutically effective amount of a compound according to claim 6.

* * * * *

UNITED STATES PATENT AND TRADEMARK OFFICE
CERTIFICATE OF CORRECTION

PATENT NO. : 8,415,386 B2  
APPLICATION NO. : 13/122995  
DATED : April 9, 2013  
INVENTOR(S) : Devasthale et al.

Page 1 of 1

It is certified that error appears in the above-identified patent and that said Letters Patent is hereby corrected as shown below:

In the Claims:

Column 130, Claim 1  
Line 6, "$R^{2c}$are" should read -- $R^{2c}$ are --; and  
Line 26, "7membered" should read -- 7- membered --.

Column 131, Claim 2  
Line 55, "$R^{2b, \text{ and } R2c}$" should read -- $R^{2b}$, and $R^{2c}$ --; and  
Line 58, "$R^{2b}$are" should read -- $R^{2b}$ are --.

Column 137, Claim 6

Lines 17-22, " 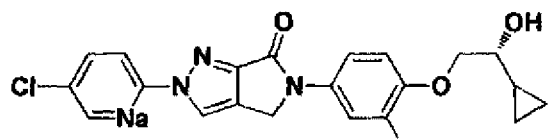 " should read

-- 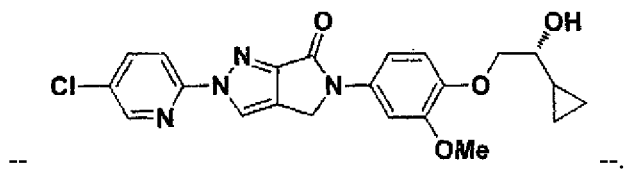 --.

Signed and Sealed this  
Tenth Day of September, 2013

Teresa Stanek Rea  
*Acting Director of the United States Patent and Trademark Office*